United States Patent
Bajji et al.

(10) Patent No.: US 11,414,442 B2
(45) Date of Patent: Aug. 16, 2022

(54) ARF6 INHIBITORS AND RELATED METHODS

(71) Applicant: Navigen, Inc., Salt Lake City, UT (US)

(72) Inventors: Ashok Bajji, Salt Lake City, UT (US); Kirill Ostanin, Salt Lake City, UT (US); Alan Mueller, Salt Lake City, UT (US); Damon Papac, Salt Lake City, UT (US)

(73) Assignee: Navigen, Inc., Salt Lake City, UT (US)

( * ) Notice: Subject to any disclaimer, the term of this patent is extended or adjusted under 35 U.S.C. 154(b) by 0 days.

(21) Appl. No.: 16/798,024

(22) Filed: Feb. 21, 2020

(65) Prior Publication Data

US 2021/0017201 A1    Jan. 21, 2021

Related U.S. Application Data

(63) Continuation of application No. PCT/US2018/047333, filed on Aug. 21, 2018.

(60) Provisional application No. 62/548,188, filed on Aug. 21, 2017.

(51) Int. Cl.
*C07F 9/09* (2006.01)
*C07D 403/04* (2006.01)

(52) U.S. Cl.
CPC ............. *C07F 9/09* (2013.01); *C07D 403/04* (2013.01)

(58) Field of Classification Search
CPC ....................................................... C07F 9/09
See application file for complete search history.

(56) References Cited

U.S. PATENT DOCUMENTS

2018/0079753 A1* 3/2018 Konteatis ................ A61P 35/00

FOREIGN PATENT DOCUMENTS

| EP | 2518070 | 10/2012 | |
| EP | 2617723 | 7/2013 | |
| EP | 3041474 | 7/2016 | |
| WO | WO-2012149157 A2 * | 11/2012 | ................ A61P 3/10 |
| WO | 2015183989 | 12/2015 | |
| WO | 2018045071 | 3/2018 | |
| WO | WO-2018039972 A1 * | 3/2018 | ........... C07D 487/04 |

OTHER PUBLICATIONS

Extended European Search Report dated Aug. 23, 2021 for EP application 18849346.4.

* cited by examiner

*Primary Examiner* — David K O'Dell
(74) *Attorney, Agent, or Firm* — Dorsey & Whitney LLP

(57) ABSTRACT

Methods of treating vascular leak, vascular inflammation, angiogenesis, ocular disorders, and/or inflammatory disorders in a patient are provided. The methods can include administering an ADP-ribosylation factor 6 (ARF6) inhibitor to the patient. The present disclosure also relates to new chemical entities and pharmaceutical compositions including ARF6 inhibitors. The ARF6 inhibitor may be a prodrug of an ARF6 inhibitor.

18 Claims, 25 Drawing Sheets

ARF6 INHIBITORS AND RELATED METHODS

CROSS-REFERENCE TO RELATED APPLICATIONS

This application is a continuation of International Patent Application No. PCT/US2018/047333, filed on Aug. 21, 2018, which claims the benefit of U.S. Provisional Application No. 62/548,188, filed on Aug. 21, 2017, the entire contents of each of which are hereby incorporated by reference in their entirety.

TECHNICAL FIELD

The present disclosure relates to methods of treating vascular leak, vascular inflammation, angiogenesis, ocular disorders, and/or inflammatory disorders in a patient. The methods can include administering an ADP-ribosylation factor 6 (ARF6) inhibitor to the patient. The present disclosure also relates to new ARF6 inhibitors (e.g., new chemical entities (NCEs)) and pharmaceutical compositions including ARF6 inhibitors. The ARF6 inhibitor may be a prodrug of an ARF6 inhibitor.

BACKGROUND

ARF6 is a small GTPase of the Ras superfamily that, by virtue of its powerful roles in endocytic trafficking and cell surface actin remodeling, represents an important player in regulation of cell-cell adhesion and cell motility (see Donaldson J G. *The Journal of biological chemistry.* 2003; 278:41573-6 and Schweitzer J K, et al. *Seminars in cell & developmental biology.* 2011; 22:39-47). ARF6 is activated by the exchange of intrinsically bound GDP for GTP that, depending on physiological context, can be catalyzed by a number of guanine nucleotide exchange factors (GEFs) (see Gillingham A K, et al. *Annual review of cell and developmental biology.* 2007; 23:579-611). Activation of ARF6 in endothelial cells is characterized by endocytosis of vascular endothelial (VE)-cadherin (see Zhu W, et al. *Nature.* 2012; 492:252-5 and Davis C T, et al. *Journal of immunology.* 2014; 192:6045-52), an essential component of interendothelial adherens junctions (see Komarova Y, et al. *Annual review of physiology.* 2010; 72:463-93; Gavard J, et al. *Nature cell biology.* 2006; 8:1223-34; London N R, et al. *Angiogenesis.* 2009; 12:149-58; and Dejana E, et al. *Journal of cell science.* 2008; 121:2115-22). This leads to vascular hyperpermeability (vascular leak), which can in turn lead to end organ failure and death. It has been demonstrated that ARF6 represents a convergence point of the signaling pathways downstream from several receptors with documented roles in inflammation: IL-1R (see Zhu W, et al. *Nature.* 2012; 492:252-5), TLR4 (see Davis C T, et al. *Journal of immunology.* 2014; 192:6045-52), IL-6R, and VEGFR. It is proposed herein that ARF6 inhibition can be an effective approach to control cytokine-induced vascular permeability irrespective of the cause (chronic inflammation, infection, etc.). Small molecule inhibitors of ARF6, therefore, are useful in prevention and treatment of conditions characterized by excessive vascular leak.

BRIEF DESCRIPTION OF THE FIGURES

The written disclosure herein describes illustrative embodiments that are non-limiting and non-exhaustive. Reference is made to certain of such illustrative embodiments that are depicted in the figures described herein.

DETAILED DESCRIPTION

Figure 1:
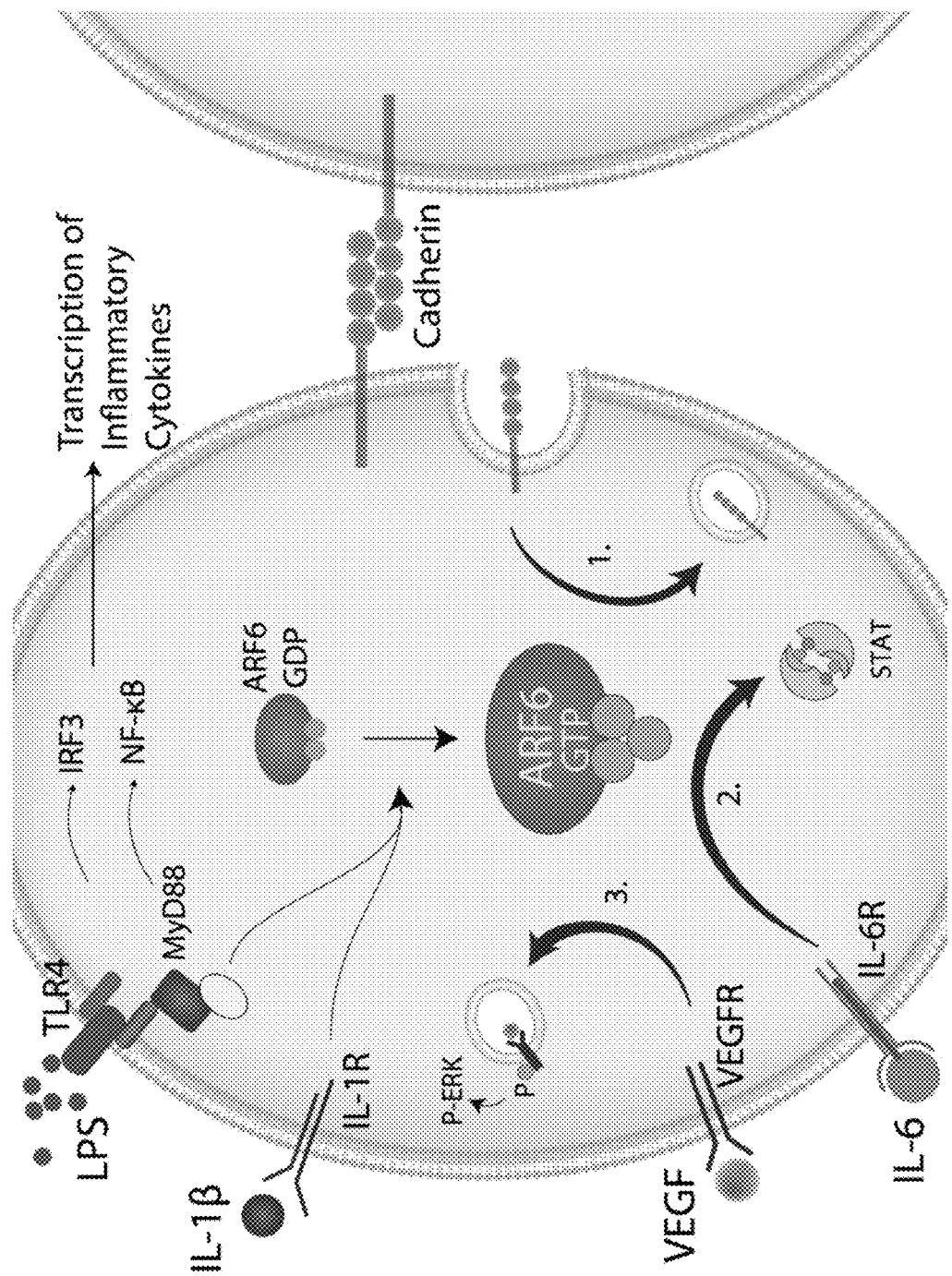
FIG. 1 illustrates that ARF6 is activated by a number of inflammatory mediators (LPS), cytokines (IL-1β, Il-6) and growth factors (VEGF). An active GTP-bound form of ARF6 mediates VE-cadherin internalization downstream of TLR4 (LPS) and IL-1β pathways (1), potentiates IL-6-induced JAK/STAT signaling (2), and leads to VEGFR internalization and p-ERK signaling (3). When ARF6 is in its inactive GDP-bound form, the adherens junctions and vasculature are stabilized.

In general, the present disclosure relates to compounds of Formulas I and II, pharmaceutically acceptable salts thereof, and pharmaceutical compositions comprising the compounds of Formulas I and II and the pharmaceutically acceptable salts thereof. Those skilled in the art will recognize that compounds of Formulas I and II are regio-isomers having identical molecular formulae and molecular weights.

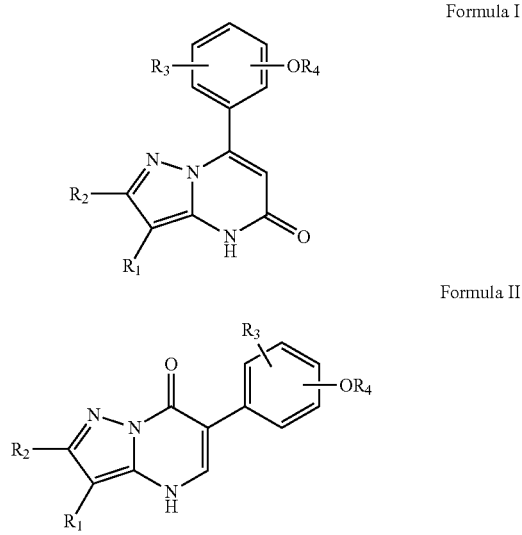

In the compounds of Formulas I and II, the group labeled $R_1$ may be independently selected from at least one of an aryl group (e.g., an optionally substituted aryl) or a cycloalkyl group. In some embodiments, the aryl group may be substituted with one or more halo groups. For example, the aryl group may be substituted with one or more chloro groups.

In the compounds of Formulas I and II, the group labeled $R_2$ may be independently selected from at least one of a morpholino group coupled through a spacer (e.g., the spacer may be a $C_1$-$C_4$ alkyl group), an aryl group, a heteroaryl group, an unstaturated cycloalkyl group, a saturated cycloalkyl group, an unsaturated heterocyclic group, a saturated heterocyclic group, a halogenated alkyl group, or a cyclopropyl group. In various embodiments, the halogenated alkyl group may be a —$CF_3$ group.

In the compounds of Formulas I and II, the group labeled $R_3$ may be independently selected from an aryl group, a heteroaryl group, a keto group, an alkyl group, a cycloalkyl group, an alkoxy group, a hydroxy group, a halo group (e.g., a fluoro group, a chloro group, etc.), a nitro group, a cyano group, an alkyne group, an alkyne amino group (e.g., a terminal amino group), and/or a phosphate group. In some embodiments, the aryl group may be substituted. In certain embodiments, the alkyne group may be coupled to the aryl ring via a spacer. For example, the spacer may be a C1-C4 alkyl group.

In the compounds of Formulas I and II, the group labeled $R_4$ may be independently selected from a hydrogen, an alkyl group, a cycloalkyl group, a carboxylic acid, and/or an ester via a spacer through the oxygen atom. For example, the spacer may be a C1-C4 alkyl In certain embodiments of the compounds having a structure according to Formulas I or II, $R_4$, together with the oxygen through which it is attached, may be independently selected from an ester, an oxygenated ester, an oxaester, a pegylated ester, a hydroxylated ester, an alkyl ester, a carboxyalkyl ester, a carboxy alkenyl ester, an aromatic ester, a hetero aromatic ester, an amino ester, an amino acid ester, an alkylamino ester, a carbonate, an alkyl carbonate, a carbamate, an alkyl carbamate, an amino carbamate, an alkylamino carbamate, a dialkylamino carbamate, and/or a glucuronate. In various embodiments of the compounds having a structure according to Formulas I or II, $R_4$ may be independently selected from a sulfonate, a phosphonate, and/or a sulfonate or a phosphonate connected through a one-, two- or, or three-carbon spacer.

In various embodiments, $R_4$ can be a promoiety linked to the remainder of the compound through an ester bond. In some embodiments, $R_4$ may be an amino acid residue linked to the remainder of the compound through an ester bond. Such embodiments may be referred to as "amino acid esters." Such amino acid esters can include esters of any of the so-called "naturally occurring amino acids" that serve as the building block of proteins.

The "naturally occurring amino acids" include glycine, and the "L-forms" of alanine, serine, threonine, cysteine, valine, leucine, isoleucine, methionine, phenylalanine, tyrosine, tryptophan, aspartic acid, glutamic acid, asparagine, glutamine, histidine, lysine, and arginine. The "amino acid esters" can also include esters of "non-naturally occurring amino acids." The "non-naturally occurring amino acids" include the alternative enantiomers of the "naturally occurring amino acids," such as D-amino acids. "Non-naturally occurring amino acids" also include amino acids having side chains attached to their alpha-carbons that are distinct from those in the "naturally occurring amino acids."

In some embodiments, $R_4$ can be a polypeptide comprising 2, 3, 4, 5, or 6 amino acid residues linked together by polypeptide bonds and linked to the remainder of the compound through an ester bond. In certain embodiments, $R_4$ may be a promoiety linked to the remainder of the compound through a carbamate bond. In various embodiments, $R_4$ can be a promoiety linked to the remainder of the compound through a carbonate bond. In some embodiments, $R_4$ can be a sulfate residue or a phosphate residue.

All chiral conformations and combinations thereof are included in the compounds of Formulas I and II. When different substituents are recited for the R groups, there is no chirality assumed or intended by the order of recitation, although all conformations are included. Some of the compounds of Formulas I and II for use in embodiments of the present disclosure may exist as single stereoisomers (i.e., essentially free of other stereoisomers), racemates, and/or mixtures of enantiomers, and/or diastereomers. All such single stereoisomers, racemates, and mixtures thereof are intended to be within the scope of the present disclosure. Furthermore, some of the compounds for use in embodiments of the present disclosure can exist as cis and trans geometric isomers, and all such isomers and mixtures thereof are intended to be within the scope of the present disclosure. Furthermore, some of the compounds for use in embodiments of the present disclosure can exist as regio-isomers, and all such regio-isomers and mixtures thereof are intended to be within the scope of the present disclosure.

Exemplary compounds of Formula I, and analogs thereof, can include the compounds shown in Table 1. The compounds of Formula I can include pharmaceutically acceptable salts thereof.

TABLE 1

Exemplary Compounds of Formula I

| | | Solubility | | ARF6 |
| --- | --- | --- | --- | --- |
| | | Water | PBS pH 7.4 | IC50 (μM) |
| NAV-A | (structure) | 35 | 8 | 2.7 |
| NAV-B | (structure) | 425 | 1.7 | 2.6 |
| NAV-C | (structure) | 9.2 | 1.4 | 7.2 |

TABLE 1-continued

Exemplary Compounds of Formula I

| | Solubility | | ARF6 |
|---|---|---|---|
| | Water | PBS pH 7.4 | IC50 (μM) |
| NAV-D | <1 | <1 | 11 |
| NAV-E | <1 | 68 | 12 |
| NAV-F | <1 | 21 | 4.9 |

TABLE 1-continued
Exemplary Compounds of Formula I
| | | Solubility | | ARF6 |
|---|---|---|---|---|
| | | Water | PBS pH 7.4 | IC50 (μM) |
| NAV-G | 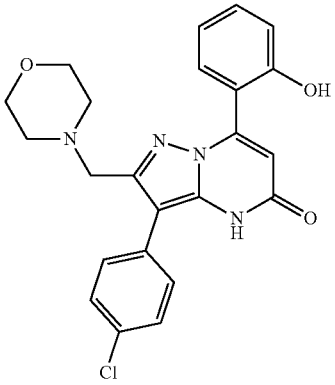 [SMILES: O=c1cc(-c2ccccc2O)n2nc(CN3CCOCC3)c(-c3ccc(Cl)cc3)c2[nH]1] | 56 | 82 | >50 |
| NAV-H | 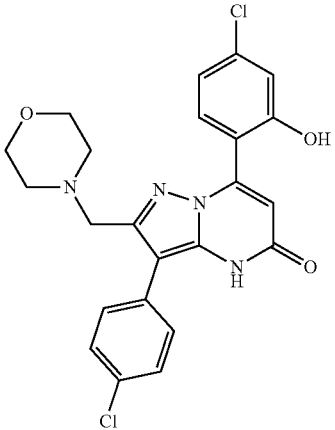 [SMILES: O=c1cc(-c2ccc(Cl)cc2O)n2nc(CN3CCOCC3)c(-c3ccc(Cl)cc3)c2[nH]1] | 7 | 13 | 30 |
| NAV-I | 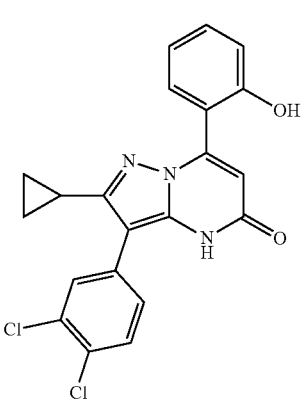 [SMILES: O=c1cc(-c2ccccc2O)n2nc(C3CC3)c(-c3ccc(Cl)c(Cl)c3)c2[nH]1] | 29 | 1.8 | 21 |

TABLE 1-continued
Exemplary Compounds of Formula I
| | | Solubility | | ARF6 |
| --- | --- | --- | --- | --- |
| | | Water | PBS pH 7.4 | IC50 (μM) |
| NAV-J | 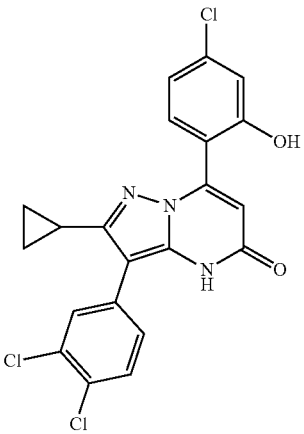 [SMILES: O=c1cc(-c2ccc(Cl)cc2O)n2nc(C3CC3)c(-c3ccc(Cl)c(Cl)c3)c2[nH]1] | <1 | <1 | 12 |
| NAV-K | 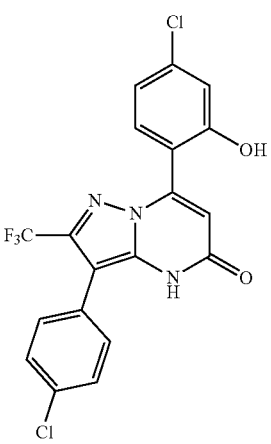 [SMILES: O=c1cc(-c2ccc(Cl)cc2O)n2nc(C(F)(F)F)c(-c3ccc(Cl)cc3)c2[nH]1] | <1 | 43 | 4.2 |
| NAV-L | 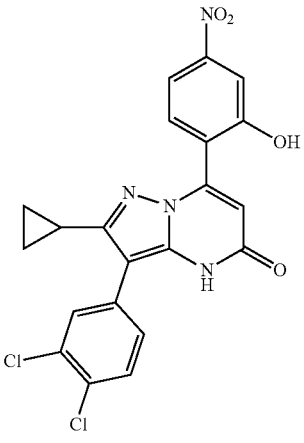 [SMILES: O=c1cc(-c2ccc([N+](=O)[O-])cc2O)n2nc(C3CC3)c(-c3ccc(Cl)c(Cl)c3)c2[nH]1] | <1 | 20 | 6.2 |

TABLE 1-continued
Exemplary Compounds of Formula I
| | Solubility | | ARF6 |
| --- | --- | --- | --- |
| | Water | PBS pH 7.4 | IC50 (μM) |
| NAV-M 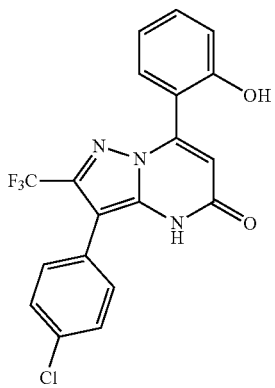 [SMILES: O=c1cc(-c2ccccc2O)n2nc(C(F)(F)F)c(-c3ccc(Cl)cc3)c2[nH]1] | 4 | 43 | 10 |
| NAV-O 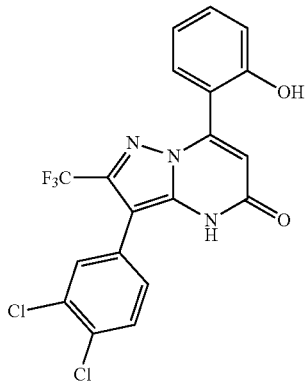 [SMILES: O=c1cc(-c2ccccc2O)n2nc(C(F)(F)F)c(-c3ccc(Cl)c(Cl)c3)c2[nH]1] | <1 | 38 | 2.8 |
| NAV-P 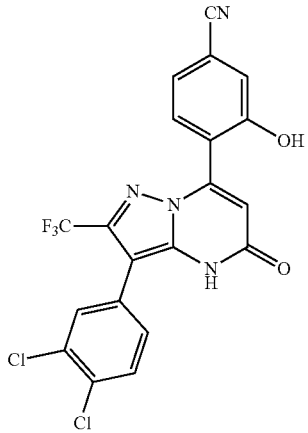 [SMILES: N#Cc1ccc(-c2cc(=O)[nH]c3c(-c4ccc(Cl)c(Cl)c4)c(C(F)(F)F)nn23)c(O)c1] | 5.75 | 19.6 | 1.4 |

TABLE 1-continued

Exemplary Compounds of Formula I

| | Solubility | | ARF6 |
| --- | --- | --- | --- |
| | Water | PBS pH 7.4 | IC50 (μM) |
| NAV-Q | <1 | 11 | 5.1 |
| NAV-R | <1 | 1.7 | 1.9 |
| NAV-S | 10.2 | 14 | 2.0 |

TABLE 1-continued

Exemplary Compounds of Formula I

| | | Solubility | | ARF6 |
|---|---|---|---|---|
| | | Water | PBS pH 7.4 | IC50 (μM) |
| NAV-T | [2-(3,4-dichlorophenyl)-3-(trifluoromethyl)-7-(2-hydroxy-4-(trifluoromethyl)phenyl)pyrazolo[1,5-a]pyrimidin-5(4H)-one] | 13 | 11 | 2.3 |
| NAV-U | [2-benzyl-3-(4-chlorophenyl)-7-(2-hydroxy-4-(trifluoromethyl)phenyl)pyrazolo[1,5-a]pyrimidin-5(4H)-one] | 20 | 14 | 6.7 |
| NAV-V | [3-(3,4-dichlorophenyl)-2-cyclopropyl-7-(2-hydroxy-4-(trifluoromethyl)phenyl)pyrazolo[1,5-a]pyrimidin-5(4H)-one] | 30 | 6 | 3.2 |

TABLE 1-continued

Exemplary Compounds of Formula I

| | Solubility | | ARF6 |
| --- | --- | --- | --- |
| | Water | PBS pH 7.4 | IC50 (μM) |
| NAV-Y | 438 | 143.5 | 30 |
| NAV-Z | 450 | 22 | 4.25 |
| NAV-AA | >500 | 19 | 1.9 |

TABLE 1-continued
Exemplary Compounds of Formula I
| | | Solubility | | ARF6 |
| --- | --- | --- | --- | --- |
| | | Water | PBS pH 7.4 | IC50 (μM) |
| NAV-AB | 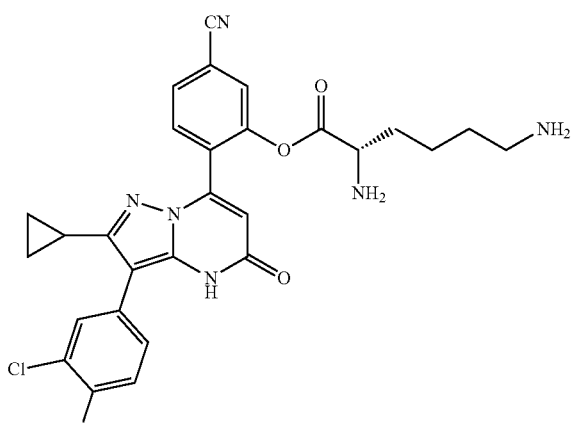 | 500 | <1 | 2.4 |
| NAV-AD | 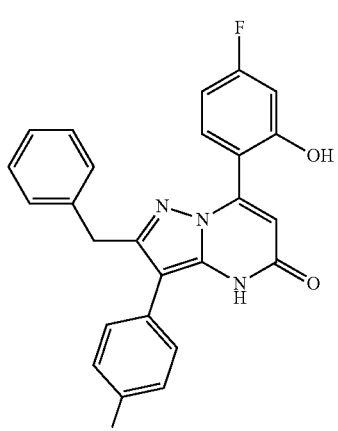 | <1 | <1 | 2.4 |
| NAV-AF | 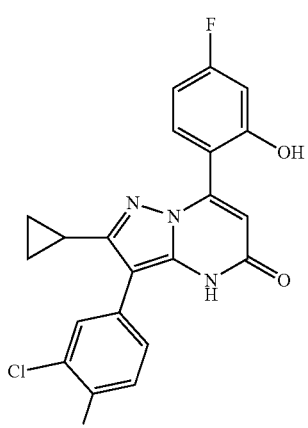 | 1.1 | <1 | 1.9 |

TABLE 1-continued

Exemplary Compounds of Formula I

| | Solubility | | ARF6 |
|---|---|---|---|
| | Water | PBS pH 7.4 | IC50 (μM) |
| NAV-AG | >500 | 435 | 26 |
| NAV-AH | ND | ND | ND |
| NAV-AI | ND | ND | ND |

TABLE 1-continued

Exemplary Compounds of Formula I

| | Solubility | | ARF6 |
| --- | --- | --- | --- |
| | Water | PBS pH 7.4 | IC50 (μM) |
| NAV-AJ | ND | ND | ND |
| NAV-AK | ND | ND | ND |

TABLE 1-continued

Exemplary Compounds of Formula I

| | | Solubility | | ARF6 |
|---|---|---|---|---|
| | | Water | PBS pH 7.4 | IC50 (μM) |
| NAV-AL | [structure: 4-ethynyl-2-hydroxyphenyl group attached to pyrazolopyrimidinone with CF₃ and 3,4-dichlorophenyl substituents] | ND | ND | ND |
| NAV-AM | [structure: 4-ethynyl-2-hydroxyphenyl group attached to pyrazolopyrimidinone with CF₃ and 3,4-dichlorophenyl substituents] | ND | ND | ND |
| NAV-AN | [structure: 4-(3-hydroxyprop-1-yn-1-yl)-2-hydroxyphenyl group attached to pyrazolopyrimidinone with CF₃ and 3,4-dichlorophenyl substituents] | ND | ND | ND |

TABLE 1-continued

Exemplary Compounds of Formula I

| | Solubility | | ARF6 |
|---|---|---|---|
| | Water | PBS pH 7.4 | IC50 (μM) |
| NAV-AO | ND | ND | ND |
| NAV-AP | ND | ND | N D |
| NAV-AQ | ND | ND | ND |

TABLE 1-continued

Exemplary Compounds of Formula I

| | Solubility | | ARF6 |
| --- | --- | --- | --- |
| | Water | PBS pH 7.4 | IC50 (μM) |
| NAV-AR | ND | ND | ND |
| NAV-AS | ND | ND | ND |
| NAV-AT | ND | ND | ND |

TABLE 1-continued

Exemplary Compounds of Formula I

| | Solubility | | ARF6 |
|---|---|---|---|
| | Water | PBS pH 7.4 | IC50 (μM) |
| NAV-AU | ND | ND | ND |
| NAV-AV | ND | ND | ND |
| NAV-AW | <1 | 30 | 1.6 |

TABLE 1-continued
Exemplary Compounds of Formula I
| | Solubility | | ARF6 |
|---|---|---|---|
| | Water | PBS pH 7.4 | IC50 (μM) |
| NAV-AX 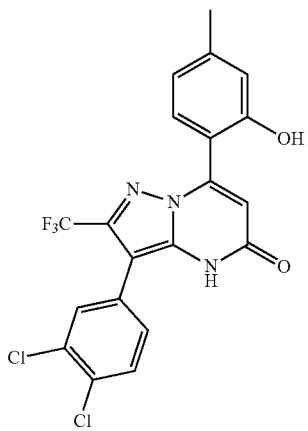 [SMILES: Cc1ccc(-c2cc(=O)[nH]c3c(-c4ccc(Cl)c(Cl)c4)c(C(F)(F)F)nn23)c(O)c1] | ND | ND | ND |
| NAV-AY 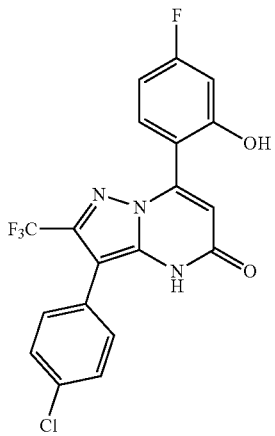 [SMILES: O=c1cc(-c2ccc(F)cc2O)n2nc(C(F)(F)F)c(-c3ccc(Cl)cc3)c2[nH]1] | 4.5 | 70 | 6.2 |
| NAV-AZ 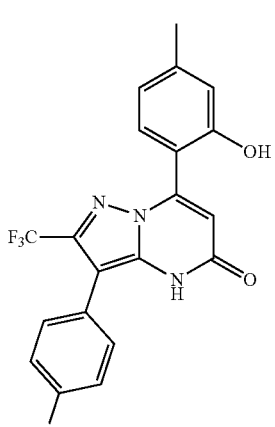 | ND | ND | ND |

TABLE 1-continued

Exemplary Compounds of Formula I

| | | Solubility | | ARF6 |
| --- | --- | --- | --- | --- |
| | | Water | PBS pH 7.4 | IC50 (μM) |
| NAV-AAA | (structure) | ND | ND | ND |
| NAV-AAB | (structure) | ND | ND | ND |
| NAV-AAC | (structure) | ND | ND | ND |

TABLE 1-continued
Exemplary Compounds of Formula I
| | | Solubility | | ARF6 |
| --- | --- | --- | --- | --- |
| | | Water | PBS pH 7.4 | IC50 (µM) |
| NAV-AAD | 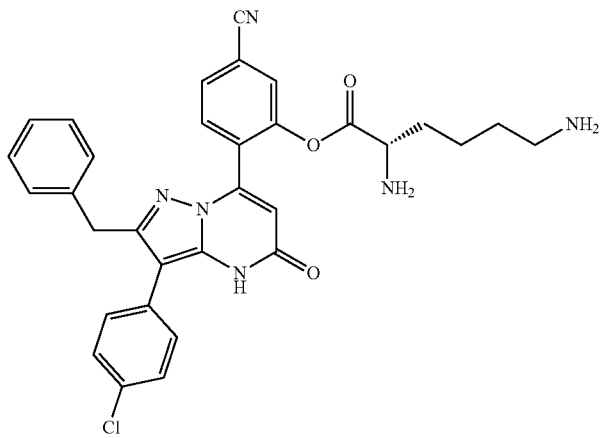 [SMILES: N#Cc1ccc(-c2cc(=O)[nH]c3c(-c4ccc(Cl)cc4)c(Cc4ccccc4)nn23)c(OC(=O)[C@@H](N)CCCCN)c1] | 300 | <1 | 2.9 |
| NAV-AAE | 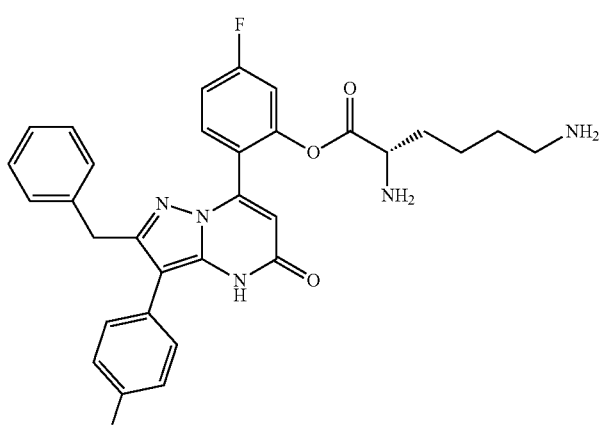 | ND | ND | 3.3 |
| NAV-AAF | 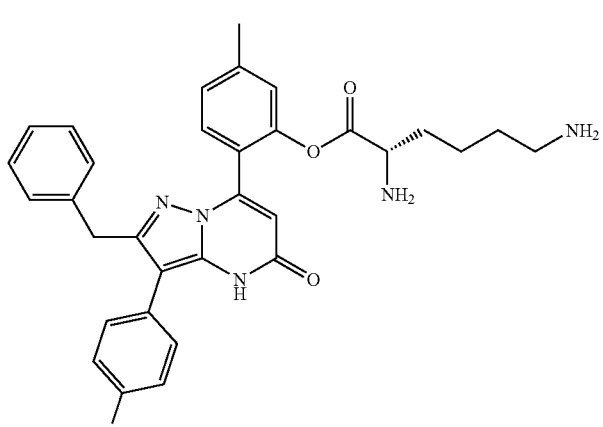 | ND | ND | >50 |

TABLE 1-continued
Exemplary Compounds of Formula I
| | | Solubility | | ARF6 |
|---|---|---|---|---|
| | | Water | PBS pH 7.4 | IC50 (μM) |
| NAV-AAG | 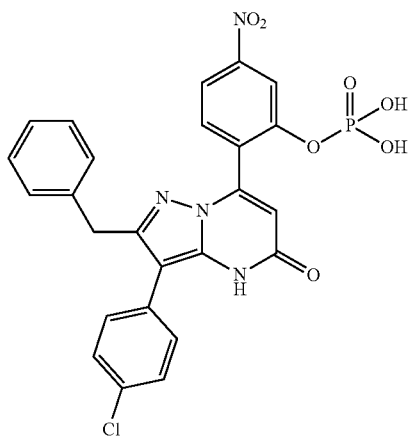 [SMILES: O=c1cc(-c2ccc([N+](=O)[O-])cc2OP(=O)(O)O)n2nc(Cc3ccccc3)c(-c3ccc(Cl)cc3)c2[nH]1] | ND | ND | ND |
| NAV-AAH | 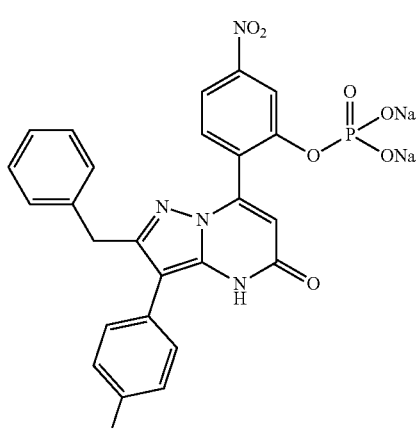 | ND | ND | ND |
| NAV-AAI | 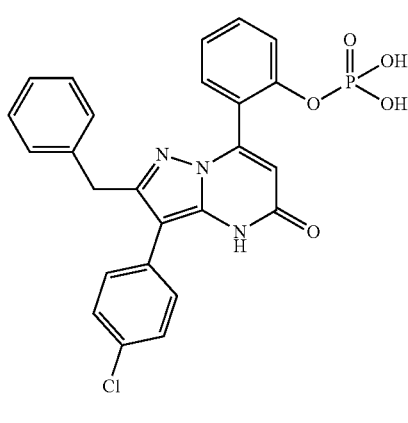 [SMILES: O=c1cc(-c2ccccc2OP(=O)(O)O)n2nc(Cc3ccccc3)c(-c3ccc(Cl)cc3)c2[nH]1] | ND | ND | ND |

TABLE 1-continued
Exemplary Compounds of Formula I
| | Solubility | | ARF6 |
|---|---|---|---|
| | Water | PBS pH 7.4 | IC50 (μM) |
| NAV-AAJ 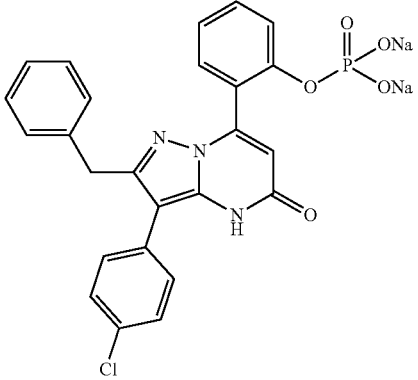 | ND | ND | ND |
| NAV-AAK 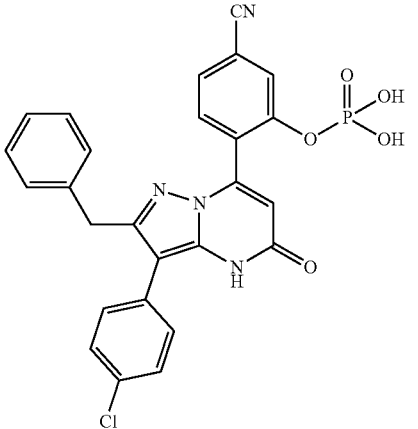 [SMILES: N#Cc1ccc(-c2cc(=O)[nH]c3c(-c4ccc(Cl)cc4)c(Cc4ccccc4)nn23)c(OP(=O)(O)O)c1] | ND | ND | ND |
| NAV-AAL 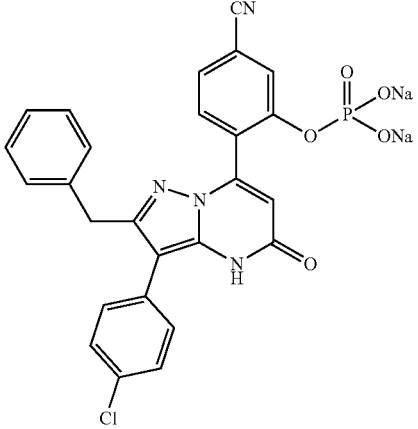 | ND | ND | ND |

TABLE 1-continued

Exemplary Compounds of Formula I

| | | Solubility | | ARF6 |
|---|---|---|---|---|
| | | Water | PBS pH 7.4 | IC50 (μM) |
| NAV-AAM | [structure: 2-benzyl-3-(4-chlorophenyl)-7-(4-(trifluoromethyl)-2-(phosphonooxy)phenyl)pyrazolo[1,5-a]pyrimidin-5(4H)-one] | ND | ND | ND |
| NAV-AAN | [structure: disodium salt of the phosphate in NAV-AAM] | ND | ND | ND |
| NAV-AAO | [structure: 2-benzyl-3-(4-chlorophenyl)-7-(4-fluoro-2-(phosphonooxy)phenyl)pyrazolo[1,5-a]pyrimidin-5(4H)-one] | ND | ND | ND |

TABLE 1-continued

Exemplary Compounds of Formula I

| | Solubility | | ARF6 |
|---|---|---|---|
| | Water | PBS pH 7.4 | IC50 (μM) |
| NAV-AAP | ND | ND | 9.2 |
| NAV-AAQ | >50 | ND | 4.6 |
| NAV-AAR | >50 | ND | 4.6 |

ND: Not determined

Exemplary compounds of Formula II, and analogs thereof, can include the compounds shown in Table 2. The compounds of Formula II can include pharmaceutically acceptable salts thereof.
TABLE 2
Exemplary Compounds of Formula II
| | | Solubility | | ARF6 |
| --- | --- | --- | --- | --- |
| | | Water | PBS pH 7.4 | IC50 (µM) |
| NAV-A' | 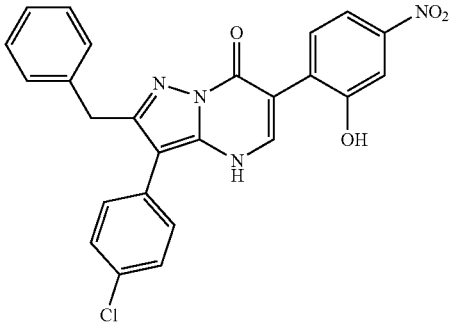 [SMILES: O=c1c(-c2ccc([N+](=O)[O-])cc2O)c[nH]c2c(-c3ccc(Cl)cc3)c(Cc3ccccc3)nn12] | ND | ND | ND |
| NAV-B' | 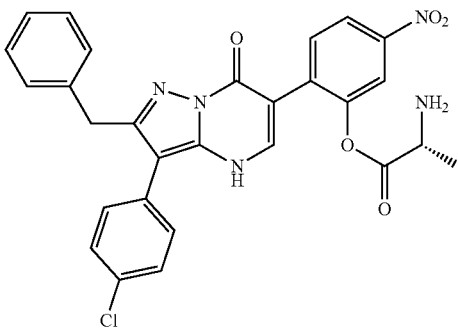 | ND | ND | ND |
| NAV-C' | 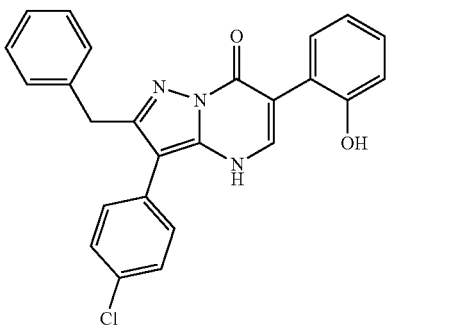 [SMILES: O=c1c(-c2ccccc2O)c[nH]c2c(-c3ccc(Cl)cc3)c(Cc3ccccc3)nn12] | ND | ND | ND |
| NAV-D' | 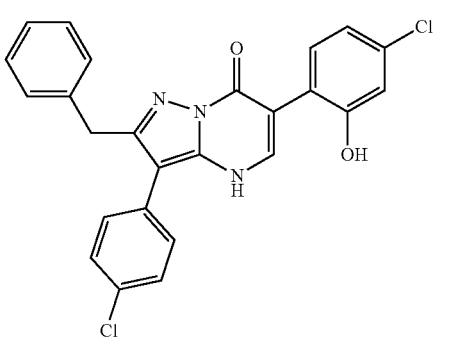 [SMILES: O=c1c(-c2ccc(Cl)cc2O)c[nH]c2c(-c3ccc(Cl)cc3)c(Cc3ccccc3)nn12] | ND | ND | ND |

TABLE 2-continued
Exemplary Compounds of Formula II
| | Solubility | | ARF6 |
|---|---|---|---|
| | Water | PBS pH 7.4 | IC50 (μM) |
| NAV-E' 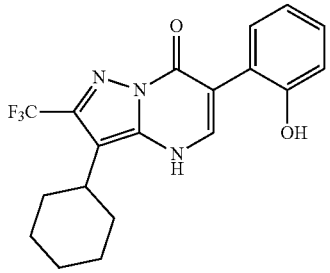 [SMILES: O=c1c(-c2ccccc2O)c[nH]c2c(C3CCCCC3)c(C(F)(F)F)nn12] | ND | ND | ND |
| NAV-F' 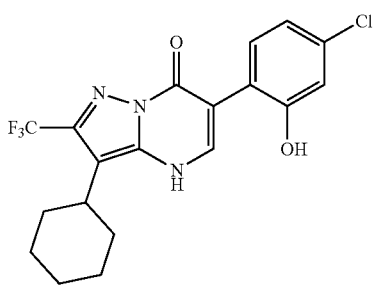 [SMILES: O=c1c(-c2ccc(Cl)cc2O)c[nH]c2c(C3CCCCC3)c(C(F)(F)F)nn12] | ND | ND | ND |
| NAV-G' 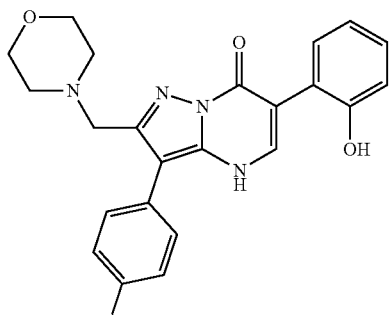 | ND | ND | ND |
| NAV-H' 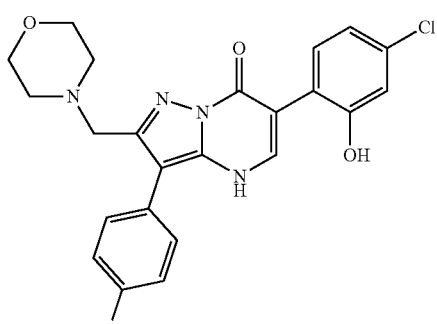 | ND | ND | ND |

TABLE 2-continued

Exemplary Compounds of Formula II

| | | Solubility | | ARF6 |
|---|---|---|---|---|
| | | Water | PBS pH 7.4 | IC50 (μM) |
| NAV-I' | (2-cyclopropyl-3-(3,4-dichlorophenyl)-6-(2-hydroxyphenyl)pyrazolo[1,5-a]pyrimidin-7(4H)-one) | ND | ND | ND |
| NAV-J' | (6-(4-chloro-2-hydroxyphenyl)-2-cyclopropyl-3-(3,4-dichlorophenyl)pyrazolo[1,5-a]pyrimidin-7(4H)-one) | ND | ND | ND |
| NAV-K' | (6-(4-chloro-2-hydroxyphenyl)-3-(4-chlorophenyl)-2-(trifluoromethyl)pyrazolo[1,5-a]pyrimidin-7(4H)-one) | ND | ND | ND |
| NAV-L' | (2-cyclopropyl-3-(3,4-dichlorophenyl)-6-(2-hydroxy-4-nitrophenyl)pyrazolo[1,5-a]pyrimidin-7(4H)-one) | ND | ND | ND |

TABLE 2-continued

Exemplary Compounds of Formula II

| | Solubility | | ARF6 |
|---|---|---|---|
| | Water | PBS pH 7.4 | IC50 (μM) |
| NAV-M' | ND | ND | ND |
| NAV-O' | ND | ND | ND |
| NAV-P' | ND | ND | ND |
| NAV-Q' | ND | ND | ND |

TABLE 2-continued

Exemplary Compounds of Formula II

| | | Solubility | | ARF6 |
|---|---|---|---|---|
| | | Water | PBS pH 7.4 | IC50 (μM) |
| NAV-R' | *[structure]* | ND | ND | ND |
| NAV-S' | *[structure]* | ND | ND | ND |
| NAV-T' | *[structure]* | ND | ND | ND |
| NAV-U' | *[structure]* | ND | ND | ND |

TABLE 2-continued

Exemplary Compounds of Formula II

| | | Solubility | | ARF6 |
|---|---|---|---|---|
| | | Water | PBS pH 7.4 | IC50 (µM) |
| NAV-V' | [structure] | ND | ND | ND |
| NAV-Y' | [structure] | ND | ND | ND |
| NAV-Z' | [structure] | ND | ND | ND |
| NAV-AA' | [structure] | ND | ND | ND |

TABLE 2-continued
Exemplary Compounds of Formula II
| | | Solubility | | ARF6 |
|---|---|---|---|---|
| | | Water | PBS pH 7.4 | IC50 (µM) |
| NAV-AB' | 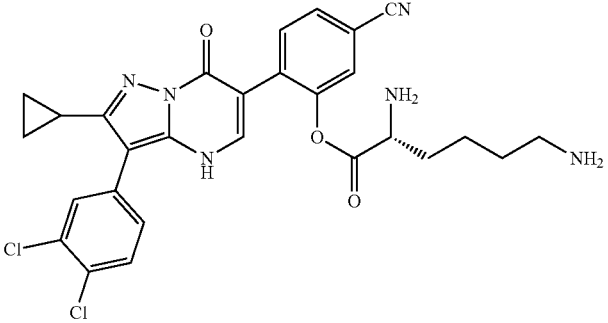 [SMILES: N#Cc1ccc(-c2c[nH]c3c(-c4ccc(Cl)c(Cl)c4)c(C4CC4)nn3c2=O)c(OC(=O)[C@H](N)CCCCN)c1] | ND | ND | ND |
| NAV-AD' | 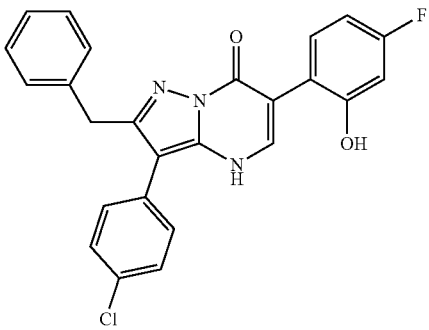 [SMILES: O=c1c(-c2ccc(F)cc2O)c[nH]c2c(-c3ccc(Cl)cc3)c(Cc3ccccc3)nn12] | ND | ND | ND |
| NAV-AF' | 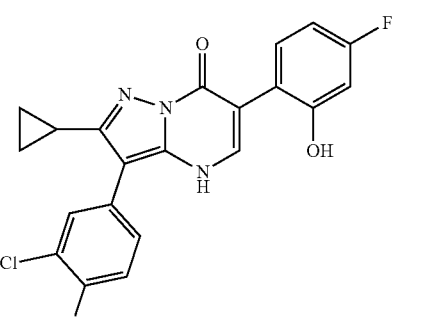 | ND | ND | ND |
| NAV-AG' | 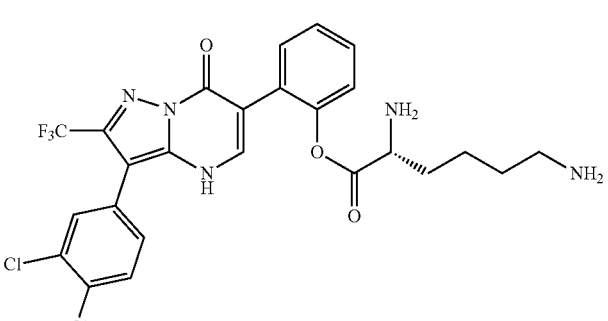 | ND | ND | ND |

TABLE 2-continued

Exemplary Compounds of Formula II

| | | Solubility | | ARF6 |
|---|---|---|---|---|
| | | Water | PBS pH 7.4 | IC50 (μM) |
| NAV-AH' | *structure* | ND | ND | ND |
| NAV-AI' | *structure* | ND | ND | ND |
| NAV-AJ' | *structure* | ND | ND | ND |
| NAV-AK' | *structure* | ND | ND | ND |

TABLE 2-continued

Exemplary Compounds of Formula II

| | Solubility | | ARF6 |
|---|---|---|---|
| | Water | PBS pH 7.4 | IC50 (μM) |
| NAV-AL' | ND | ND | ND |
| NAV-AM' | ND | ND | ND |
| NAV-AN' | ND | ND | ND |
| NAV-AO' | ND | ND | ND |

TABLE 2-continued
Exemplary Compounds of Formula II
| | | Solubility | | ARF6 |
| --- | --- | --- | --- | --- |
| | | Water | PBS pH 7.4 | IC50 (μM) |
| NAV-AP' | 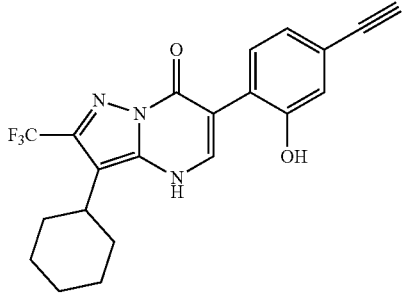 [SMILES: C#Cc1ccc(-c2c[nH]c3c(C4CCCCC4)c(C(F)(F)F)nn3c2=O)c(O)c1] | ND | ND | ND |
| NAV-AQ' | 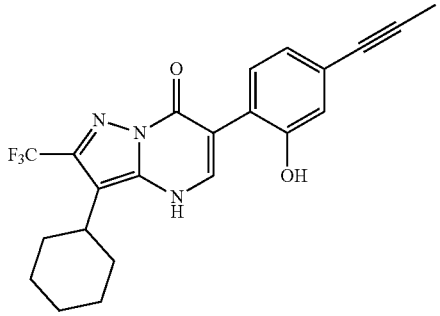 [SMILES: CC#Cc1ccc(-c2c[nH]c3c(C4CCCCC4)c(C(F)(F)F)nn3c2=O)c(O)c1] | ND | ND | ND |
| NAV-AR' | 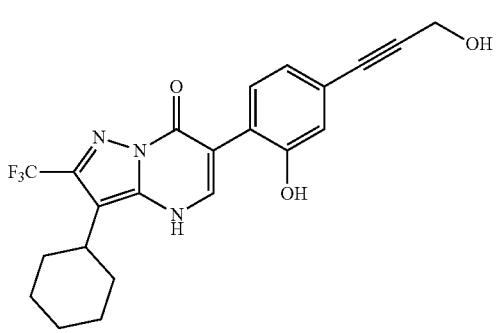 [SMILES: O=c1c(-c2ccc(C#CCO)cc2O)c[nH]c2c(C3CCCCC3)c(C(F)(F)F)nn12] | ND | ND | ND |
| NAV-AS' | 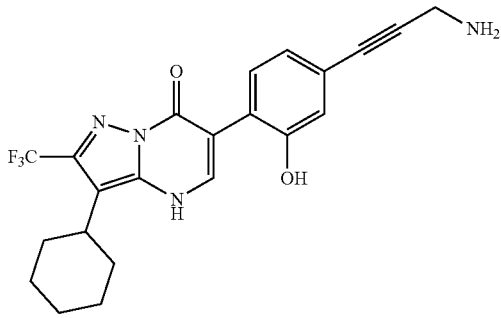 [SMILES: NCC#Cc1ccc(-c2c[nH]c3c(C4CCCCC4)c(C(F)(F)F)nn3c2=O)c(O)c1] | ND | ND | ND |

TABLE 2-continued
Exemplary Compounds of Formula II
| | | Solubility | | ARF6 |
|---|---|---|---|---|
| | | Water | PBS pH 7.4 | IC50 (μM) |
| NAV-AT' | 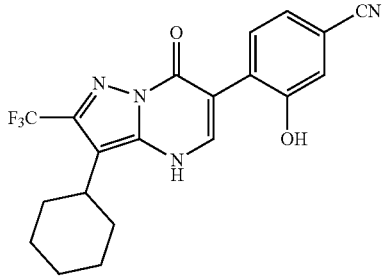 [SMILES: N#Cc1ccc(-c2c[nH]c3c(C4CCCCC4)c(C(F)(F)F)nn3c2=O)c(O)c1] | ND | ND | ND |
| NAV-AU' | 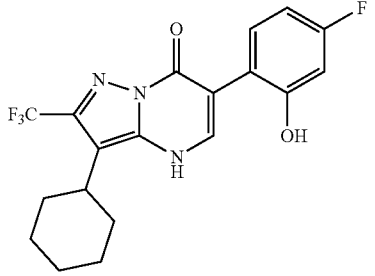 [SMILES: O=c1c(-c2ccc(F)cc2O)c[nH]c2c(C3CCCCC3)c(C(F)(F)F)nn12] | ND | ND | ND |
| NAV-AV' | 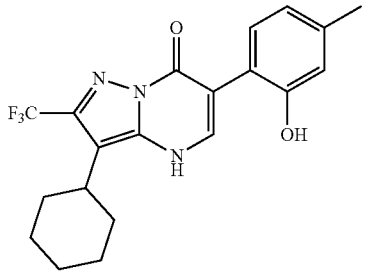 [SMILES: Cc1ccc(-c2c[nH]c3c(C4CCCCC4)c(C(F)(F)F)nn3c2=O)c(O)c1] | ND | ND | ND |
| NAV-AW' | 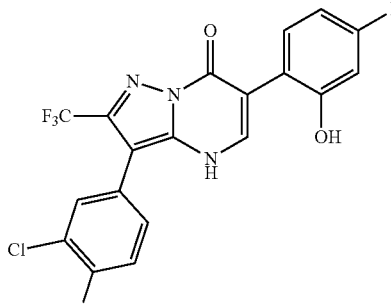 | ND | ND | ND |
| NAV-AX' | 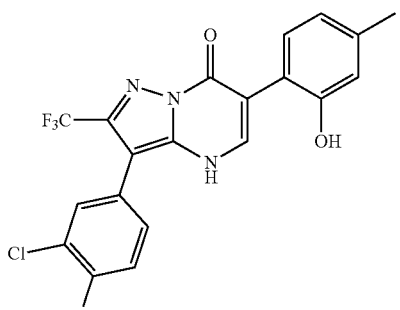 | ND | ND | ND |

TABLE 2-continued
Exemplary Compounds of Formula II
| | Solubility | | ARF6 |
|---|---|---|---|
| | Water | PBS pH 7.4 | IC50 (μM) |
| NAV-AY' 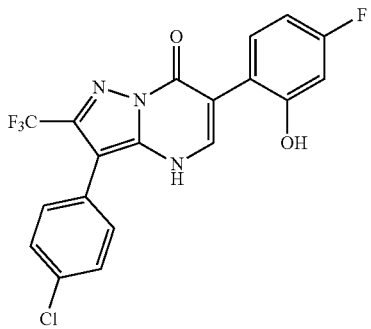 [SMILES: O=c1c(-c2ccc(F)cc2O)c[nH]c2c(-c3ccc(Cl)cc3)c(C(F)(F)F)nn12] | ND | ND | ND |
| NAV-AZ' 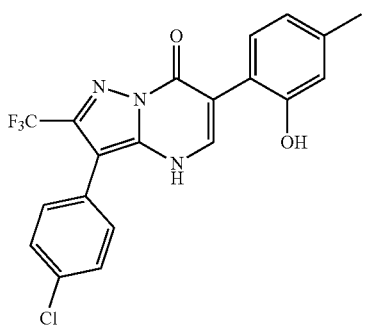 [SMILES: Cc1ccc(-c2c[nH]c3c(-c4ccc(Cl)cc4)c(C(F)(F)F)nn3c2=O)c(O)c1] | ND | ND | ND |
| NAV-AAA' 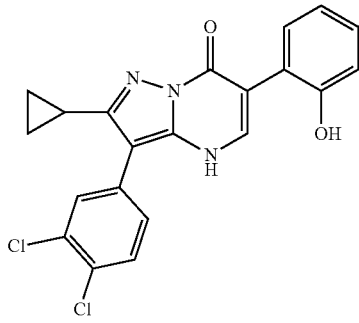 | ND | ND | ND |
| NAV-AAB' 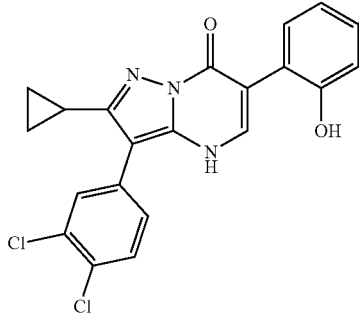 | ND | ND | ND |

TABLE 2-continued
Exemplary Compounds of Formula II
| | Solubility | | ARF6 |
| --- | --- | --- | --- |
| | Water | PBS pH 7.4 | IC50 (μM) |
| NAV-AAC' 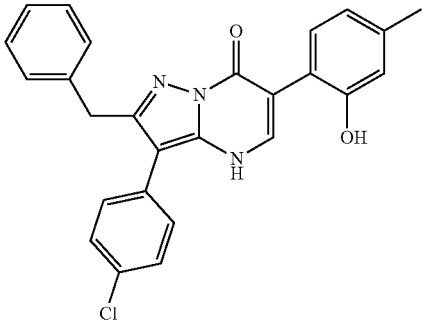 [SMILES: Cc1ccc(-c2c[nH]c3c(-c4ccc(Cl)cc4)c(Cc4ccccc4)nn3c2=O)c(O)c1] | <1 | ND | 3.3 |
| NAV-AAD' 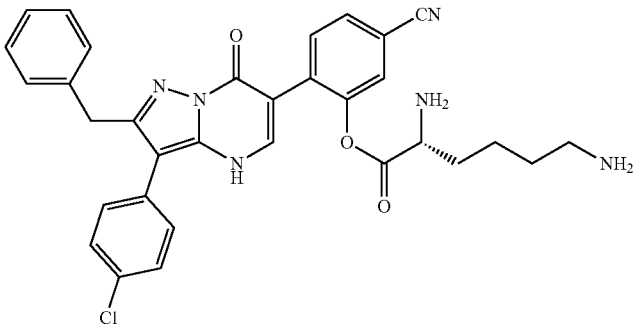 [SMILES: N#Cc1ccc(-c2c[nH]c3c(-c4ccc(Cl)cc4)c(Cc4ccccc4)nn3c2=O)c(OC(=O)[C@H](N)CCCCN)c1] | ND | ND | ND |
| NAV-AAE' 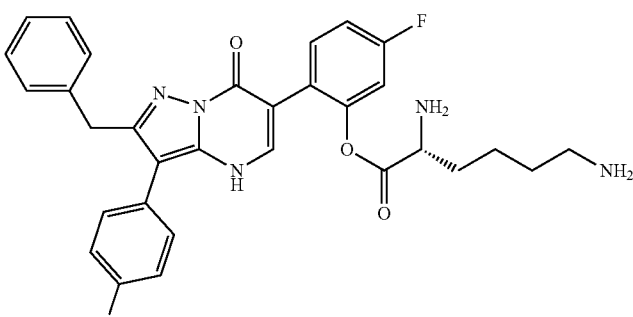 | ND | ND | ND |
| NAV-AAF' 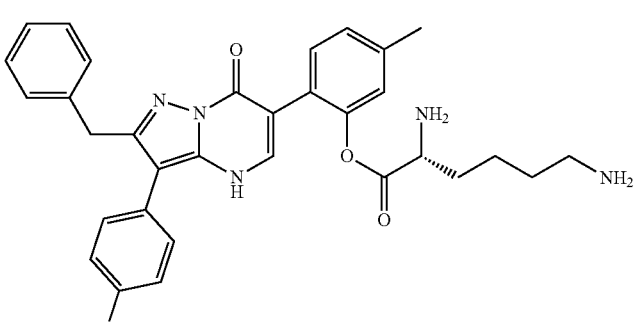 | ND | ND | ND |

TABLE 2-continued
Exemplary Compounds of Formula II
| | Solubility | | ARF6 |
|---|---|---|---|
| | Water | PBS pH 7.4 | IC50 (μM) |
| NAV-AAG' 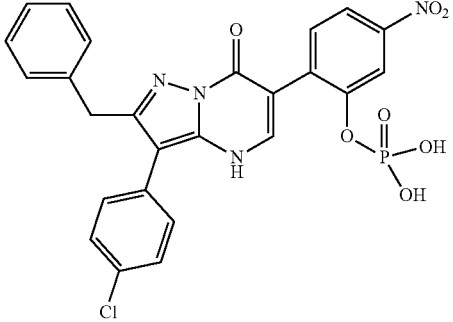 [SMILES: O=c1c(-c2ccc([N+](=O)[O-])cc2OP(=O)(O)O)c[nH]c2c(-c3ccc(Cl)cc3)c(Cc3ccccc3)nn12] | ND | ND | ND |
| NAV-AAH' 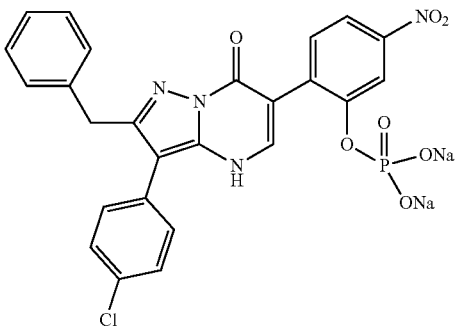 | ND | ND | ND |
| NAV-AAI' 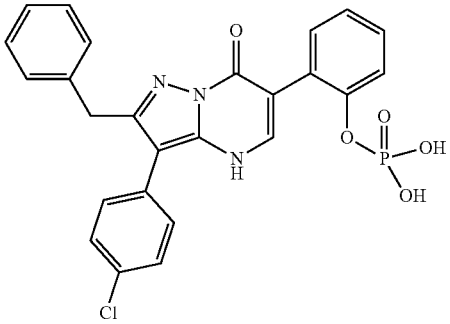 [SMILES: O=c1c(-c2ccccc2OP(=O)(O)O)c[nH]c2c(-c3ccc(Cl)cc3)c(Cc3ccccc3)nn12] | ND | ND | ND |
| NAV-AAJ' 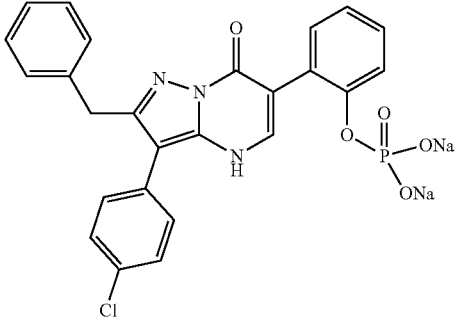 | ND | ND | ND |

TABLE 2-continued

Exemplary Compounds of Formula II

| | Solubility | | ARF6 |
|---|---|---|---|
| | Water | PBS pH 7.4 | IC50 (μM) |
| NAV-AAK' | ND | ND | ND |
| NAV-AAL' | ND | ND | ND |
| NAV-AAM' | ND | ND | ND |
| NAV-AAN' | ND | ND | ND |

TABLE 2-continued

Exemplary Compounds of Formula II

| | Solubility | | ARF6 |
|---|---|---|---|
| | Water | PBS pH 7.4 | IC50 (μM) |
| NAV-AAO' | ND | ND | ND |
| NAV-AAP' | >50 | ND | 9.2 |
| NAV-AAQ' | ND | ND | ND |
| NAV-AAR' | >50 | ND | 1-2 |

ND: Not determined

Protected derivatives of the disclosed compounds also are contemplated. A variety of suitable protecting groups for use with the compounds herein are disclosed. Other conventional protecting groups can be selected by those of skill in the art in consultation with, for example, Greene and Wuts, Protective Groups in Organic Synthesis; 3rd Ed.; John Wiley & Sons, New York, 1999.

The compounds of the present disclosure may be prepared in a variety of ways known to one skilled in the art of organic synthesis. The compounds of the present disclosure can be synthesized using the methods as described herein, together with synthetic methods known in the art of synthetic organic chemistry or variations thereof as appreciated by those skilled in the art.

The specific examples included herein are for illustrative purposes only and are not to be considered as limiting to this disclosure. Any active agents and reagents used in the following examples are either commercially available or can be prepared according to standard literature procedures by those skilled in the art of organic synthesis. In light of this disclosure, those of skill in the art will recognize that variations of these examples and other examples of the disclosed method would be possible without undue experimentation.

Some of the compounds of Formulas I and II for use in embodiments of the present disclosure may exist as single stereoisomers (i.e., essentially free of other stereoisomers), racemates, and/or mixtures of enantiomers, and/or diastereomers and/or regio-isomers. All such single stereoisomers, racemates, and mixtures thereof are intended to be within the scope of the present disclosure. Generally, the compounds that are optically active are used in a substantially optically pure form. Furthermore, some of the compounds for use in embodiments of the present disclosure can exist as cis and trans geometric isomers. All such isomers and mixtures thereof are intended to be within the scope of the present disclosure.

Additionally, the formulas are intended to cover solvated as well as unsolvated forms of the identified structures. For example, Formulas I and II include compounds of the indicated structure in both hydrated and non-hydrated forms. Other examples of solvates include the structures in combination with isopropanol, ethanol, methanol, dimethylsulfoxide (DMSO), ethyl acetate, acetic acid, or ethanolamine.

In addition to compounds of Formulas I and II, some embodiments of the present disclosure may comprise pharmaceutically acceptable prodrugs, pharmaceutically active metabolites, and pharmaceutically acceptable salts of such compounds.

Prodrugs and active metabolites of a compound may be identified using routine techniques known in the art (see, e.g., Bertolini, G et al., J. Med. Chem., 40, 2011-2016 (1997); Shan, D. et al., J. Pharm. Sci., 86 (7), 756-767; Bagshawe K., Drug Dev. Res., 34, 220-230 (1995); Bodor N.; Advance in Drug Res., 13, 224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991)).

It is to be understood that the terminology used herein is for the purpose of describing particular embodiments only and is not intended to limit the scope of the present disclosure, which will be limited only by the appended claims.

Unless defined otherwise, all technical and scientific terms used herein have the meanings that would be commonly understood by one skilled in the art. As used herein, the singular forms "a," "an," and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 50%, 30%, 20%, 10%, 5%, 1%, 0.5%, or even 0.1% of the specified amount. All publications, patent applications, patents, and other references mentioned herein are incorporated by reference in their entirety.

As used herein, the term "alkyl" refers to a saturated aliphatic hydrocarbon including straight chain and branched chain groups. In an embodiment, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms). In certain embodiments, it is a medium size alkyl having 1 to 10 carbon atoms. In some embodiments, it is a lower alkyl having 1 to 6 carbon atoms, or 1 to 4 carbon atoms. The alkyl group may be substituted or unsubstituted. When substituted, the substituent group(s) may be one or more individually selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, cyanato, isocyanato, thiocyanato, isothiocyanato, nitro, silyl, and amino.

As used herein, the term "halo" refers to chloro, fluoro, bromo, and iodo.

As used herein, the term "hydroxy" refers to an —OH group.

As used herein, the term "alkoxy" refers to both an —O-alkyl and an —O-cycloalkyl group, as defined herein, "lower alkoxy" refers to —O-lower alkyl groups.

As used herein, the term "aryloxy" refers to both an —O-aryl and an —O-heteroaryl group, as defined herein.

As used herein, the term "alkylthio" group refers to both an S-alkyl and an —S-cycloalkyl group, as defined herein.

As used herein, the term "arylthio" group refers to both an —S-aryl and an —S-heteroaryl group, as defined herein.

As used herein, the term "carbonyl" group refers to a —C(=O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "carboxy" group refers to a —C(=O)OR" group with R" as defined above.

As used herein, the term "carboxy salt" refers to a —C(=O)O— M+ group wherein M+ is selected from the group consisting of lithium, sodium, magnesium, calcium, potassium, barium, iron, zinc, and quaternary ammonium.

As used herein, the term "acetyl" group refers to a —C(=O)CH$_3$ group.

As used herein, the term "carboxylic acid" refers to a carboxy group in which R" is hydro.

As used herein, the term "haloalkyl" refers to an alkyl group substituted with 1 to 6 halo groups, and may be a haloalkyl with a —CX$_3$ group wherein X is a halo group. The halo groups can be independently selected.

As used herein, the term "cyano" refers to a —C≡N group.

As used herein, the term "sulfonyl" refers to a —S(=O)$_2$R" group, with R" being hydrogen, alkyl, or lower alkyl.

As used herein, the term "sulfonamido" refers to a —S(=O)$_2$NR"$_2$, with each R" independently selected from hydrogen, alkyl, or lower alkyl.

As used herein, the term "O-carbamyl" refers to a —OC(=O)NR"$_2$ group, with each R" independently selected from hydrogen, alkyl, or lower alkyl.

As used herein, the term "N-carbamyl" refers to a —NR"C(=O)NR"$_2$ group, with each R" independently selected from hydrogen, alkyl, or lower alkyl.

As used herein, the term "amino" refers to an —NR"$_2$ group, with each R" independently selected from the group consisting of hydrogen and alkyl.

As used herein, the term "C-amido" refers to a —C(=O)NR"$_2$ group, with each R" independently selected from hydrogen, alkyl, or lower alkyl. An "N-amido" refers to a NR"C(=O)R"— group with each R" independently selected from hydrogen, alkyl, or lower alkyl.

As used herein, the term "nitro" refers to a —NO$_2$ group.

As used herein, the term "methylene" refers to a —CH$_2$— group. A substituted methylene group is a methylene group wherein the carbon atom may be substituted with alkyl or cycloalkyl.

As used herein, the term "cycloalkyl" refers to an all-carbon monocyclic or fused alkyl ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane, and cycloheptatriene. A cycloalkyl group may be substituted or unsubstituted. When substituted, the substituent group(s) may be one or more individually selected from alkyl, aryl, heteroaryl, heterocyclic, hydroxy, alkoxy, aryloxy, mercapto, alkylthio, arylthio, cyano, halo, carbonyl, carboxy, O-carbamyl, N-carbamyl, C-amido, N-amido, nitro, and amino.

As used herein, the term "heterocycle" or "heterocyclic" refers to a saturated or partially saturated 3, 4, 5, 6, or 7-membered monocyclic, or 7, 8, 9, or 10-membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting saturated or partially saturated heterocyclic groups include tetrahydrofuranyl, pyranyl, piperidinyl, piperazinyl, pyrrolidinyl, imidazolidinyl, imidazolinyl, indolinyl, morpholinyl, pyrazolidinyl, pyrazolinyl, tetronoyl, and tetramoyl groups. Examples of "heterocycles" or "heterocyclic" rings also include, but are not limited to, morpholino, pyranyl, piperidyl, piperazinyl, pyrrolidinyl, thiomorpholino, homopiperazinyl, imidazolyl, imidazolidinyl, pyrazolidinyl, dioxanyl, and dioxolanyl. "Heterocycle" can include heteroaryls when the pi-electron system of a heterocycle is completely conjugated.

As used herein, the term "aryl" refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl, and anthracenyl. The aryl group may be substituted or unsubstituted. When substituted, the substituted group(s) may be one or more selected from halo, trihalomethyl, alkyl, hydroxy, alkoxy, aryloxy, mercapto, alkylthio, arylthio, cyano, nitro, carbonyl, C-carboxy, O-carboxy, C-amido, N-amido, N-alkyl, sulfinyl, sulfonyl, S-sulfonamido, N-sulfonamido, trihalo-methanesulfonamido, and amino.

As used herein, the term "heteroaryl" refers to groups having 5, 6, 7, 8, 9, 10, 11, 12, 13, or 14 ring atoms; 6, 10, or 14 pi electrons shared in a cyclic array; and containing carbon atoms and 1, 2, or 3 oxygen, nitrogen, or sulfur heteroatoms. Non-limiting heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthinyl, pyrrolyl, including without limitation 2H-pyrrolyl, imidazolyl, pyrazolyl, pyridyl (pyridinyl), including without limitation 2-pyridyl, 3-pyridyl, 4-pyridyl, pyrazinyl, pyrimidinyl, pyridazinyl, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2 oxobenzimidazolyl. Where the heteroaryl group contains a nitrogen atom in a ring, such nitrogen atom may be in the form of an N-oxide, e.g., a pyridyl N oxide, pyrazinyl N-oxide, and pyrimidinyl N-oxide. When substituted, the substituted group(s) may be one or more selected from alkyl, cycloalkyl, halo, trihalomethyl, hydroxy, alkoxy, aryloxy, mercapto, alkylthio, arylthio, cyano, nitro, carbonyl, sulfonamido, carboxy, sulfinyl, sulfonyl, 0-carbamyl, N-carbamyl, C-amido, N-amido, and amino.

As used herein, the term "unit dosage form" refers to a physically discrete unit, such as a capsule or tablet suitable as a unitary dosage for a human patient. Each unit contains a predetermined quantity of a compound of Formula I, which was discovered or believed to produce the desired pharmacokinetic profile which yields the desired therapeutic effect. The dosage unit is composed of a compound of Formula I in association with at least one pharmaceutically acceptable carrier, salt, excipient, or combination thereof.

As used herein, the term "dose" or "dosage" refers to the amount of active ingredient that an individual takes or is administered at one time. For example, an 800 mg dose of a compound of Formula I refers to, in the case of a twice-daily dosage regimen, a situation in which the individual takes 800 mg of a compound of Formula I or Formula II twice a day, e.g., 800 mg in the morning and 800 mg in the evening. The 800 mg of a compound of Formula I or II dose can be divided into two or more dosage units, e.g., two 400 mg dosage units of a compound of Formula I or Formula II.

As used herein, "a pharmaceutically acceptable prodrug" is a compound that may be converted under physiological conditions or by solvolysis to the specified compound or to a pharmaceutically acceptable salt of such compound.

As used herein, "a pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, "a pharmaceutically acceptable salt" is intended to mean a salt that retains the biological effectiveness of the free acids and bases of the specified compound and that is not biologically or otherwise undesirable. A compound for use in some embodiments of the present disclosure may comprise a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present disclosure with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

Pharmaceutical compositions are provided herein. Pharmaceutical compositions according to the present description include a pharmaceutically acceptable carrier and a therapeutically effective amount of an active compound according to the present description. The pharmaceutical compositions can take the form of, for example, solutions, suspensions, emulsions, tablets, pills, capsules, powders, sustained-release formulations, or suppositories. Examples of suitable pharmaceutical carriers are described in, for example, Remington's Pharmaceutical Sciences, by E. W. Martin. The pharmaceutical compositions disclosed herein may be prepared for administration by any suitable route known to the skilled artisan including, for example, intravenous, subcutaneous, intramuscular, intradermal, transdermal, intrathecal, intracerebral, intraperitoneal, intranasal, epidural, pulmonary, intravitreal, and oral routes. Administration can be immediate or rapid, such as by injection, or carried out over a period of time, such as by infusion or administration of controlled or delayed release formulations.

Where pharmaceutical formulations are prepared for treating tissues in the central nervous system, administration can be by injection or infusion into the cerebrospinal fluid (CSF). Moreover, where pharmaceutical compositions are prepared for delivery to cells or tissues in the central nervous system, the pharmaceutical composition may be formulated to include one or more carriers or components capable of promoting penetration of the active compound or a derivative of the active compound across the blood-brain barrier.

When prepared for oral administration, the pharmaceutical compositions described herein may be prepared, for example, in capsules, tablets, caplets, lozenges, and aqueous suspensions or solutions. Pharmaceutical compositions described herein prepared for oral administration can be formulated using known carriers, including known fillers, diluents, excipients, binders, surfactants, suspending agents, emulsifiers, lubricants, sweeteners, flavorants, and colorants, suited to formulation of the desired dosage form. Additionally, pharmaceutical compositions as described herein can be prepared using formulation approaches that utilize encapsulation in liposomes, microparticles, microcapsules, or receptor-mediated endocytosis (see, e.g., Wu et al. J. Biol. Chem. 262:4429-32, 1987), to facilitate delivery or uptake of the active compound.

Examples of pharmaceutically acceptable carriers include sterile liquids, such as water and oils, including those of petroleum, animal, vegetable or synthetic origin, such as peanut oil, soybean oil, mineral oil, and sesame oil. Aqueous carriers, including water, are typical carriers for pharmaceutical compositions prepared for intravenous administration. As further examples, saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, and ethanol. The composition, if desired, can also contain wetting or emulsifying agents, or pH buffering agents.

The pharmaceutical compositions described herein can be formulated using any of the active compounds described herein, including any pharmaceutically acceptable salts, esters, isomers, or solvates thereof. In certain embodiments, the pharmaceutical compositions described herein include an active compound as described herein, and in alternative embodiments, the pharmaceutical compositions include two or more active compounds according to the present description. The amount of the one or more active compounds included in the pharmaceutical composition will vary, depending upon, for example, the nature and activity of the active compound(s), the nature and composition of the dosage form, and the desired dose to be administered to a subject.

In some instances, it can be desirable to administer the compositions described herein locally to the area in need of treatment. Local administration can be achieved by, for example, and not by way of limitation, local infusion during surgery, topical application (e.g., in conjunction with a wound dressing after surgery), by injection, by means of a catheter, by means of a suppository, or by means of an implant, the implant being of a porous, non-porous, or gelatinous material, including membranes such as silastic membranes, or fibers. In one embodiment, administration can be by direct injection at the site of bacterial infection.

In another embodiment, the agent can be delivered in a vesicle, in particular a liposome. In yet another embodiment, the agent can be delivered in a controlled release system. In one such embodiment, a pump can be used. In another such embodiment, polymeric materials can be used. In yet another such embodiment, a controlled release system can be placed in proximity of the therapeutic target, thus utilizing only a fraction of the systemic dose.

In addition to one or more active compounds as described herein and a pharmaceutical carrier, pharmaceutical compositions according to the present description may include one or more additional therapeutic or prophylactic agents.

It should be understood, however, that a specific dosage and treatment regime for any particular subject or disease state will depend upon a variety of factors, including the age, body weight, general health, gender, diet, time of administration, nature of active compound(s), rate of excretion, drug combination, the judgment of the treating physician, and the severity of the particular disease being treated. Moreover, determination of the amount of a pharmaceutical composition to be administered to a subject will depend upon, among other factors, the amount and specific activity of the active compound(s) included in the pharmaceutical composition and the use or incorporation of additional therapeutic or prophylactic agents or treatment regimes. Determination of therapeutically effective dosages may be based on animal model studies and is typically guided by determining effective dosages and administration protocols that significantly reduce the occurrence or severity of disease in model subjects.

A non-limiting range for a therapeutically effective amount of the active compounds described herein is from about 0.001 mg/kg to about 100 mg/kg body weight per day. For example, pharmaceutical compositions according to the present description can be prepared and administered such that the amount of active compound according to the present description administered to a subject is selected from between about 0.001 mg/kg and about 50 mg/kg, between about 0.01 mg/kg and about 20 mg/kg, between about 0.1 and about 10 mg/kg, and between about 0.1 mg/kg and about 5 mg/kg body weight per day.

One aspect of the present disclosure relates to a first-in-class chemical series of direct, small molecule ADP-ribosylation factor 6 (ARF6) inhibitors that shows robust efficacy in a wide variety of conditions characterized by excessive vascular leak, including mouse models of lipopolysaccharide (LPS)-induced acute lung injury (ALI), *Acinetobacter baumannii* (AB) pneumonia, methicillin-resistant *Staphylococcus aureus* (MRSA) bacteremia, *Pseudomonas aeruginosa* (PA) pneumonia, systemic *Candida albicans* infection, severe cerebral malaria, multiple sclerosis, rheumatoid arthritis, and vascular eye disease. These ARF6 inhibitors were discovered using a high-throughput biochemical, fluorometric nucleotide exchange assay to screen 100,000 compounds from a commercially available compound library. Medicinal chemistry optimization efforts have also been conducted. In some embodiments, the clinical potential of the discovered small molecule ARF6 inhibitors can be limited by poor solubility. Accordingly, the synthesis and development of water soluble prodrugs of ARF6 inhibitors can be advantageous. One such compound, NAV-B (a lysine prodrug of the ARF6 inhibitor NAV-A), has been synthesized and its efficacy demonstrated in mouse models of LPS-induced ALI, AB-induced pneumonia, cecal ligation and puncture (CLP)-induced sepsis, and severe cerebral malaria.

Patient outcomes may be improved by attenuating the host response to multidrug resistant (MDR) bacterial infection. Inhibition of ARF6 can enhance vascular stability in the face of potential challenges from a variety of inflammatory mediators, while leaving intact the immune response mediated by NF-κB. Because ARF6 can act as a central convergence point for multiple inflammatory signaling pathways, multiple injury-inducing pathways can be targeted with a single compound designed to inhibit ARF6. The ARF6 inhibitors disclosed herein show promising activity in a variety of disease states characterized by excessive vascular leak (e.g., acute lung injury, acute respiratory distress syndrome, age-related macular degeneration, etc.). In some embodiments, however, the ARF6 inhibitors can have poor aqueous solubility. Design and synthesis of water soluble prodrugs of the ARF6 inhibitors can deliver new therapeutic agents with potential for both IV and oral dosing regimens.

In yet certain other embodiments, NAV-A may be synthesized according to the scheme shown below:

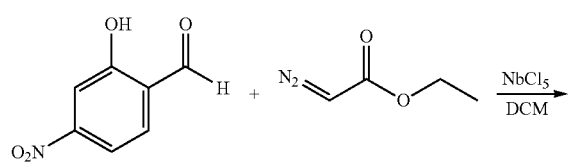

-continued

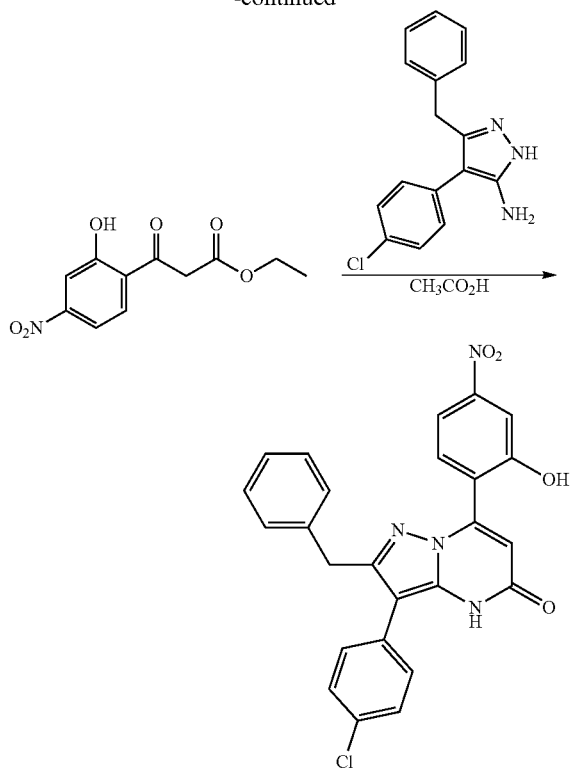

An aspect of the disclosure relates to methods for treating a patient having, or at risk of developing, a disorder relating to vascular leak, vascular inflammation, and/or angiogenesis. In certain embodiments, the method may include administering to the patient an effective amount of a pharmaceutical composition. The pharmaceutical composition may include an ARF6 inhibitor, or a pharmaceutically acceptable salt of an ARF6 inhibitor. The composition may further include a pharmaceutically acceptable carrier.

In various embodiments, the pharmaceutical composition may be administered to the patient to reduce a pathological effect or symptom of the disorder relating to vascular leak, vascular inflammation, and/or angiogenesis. In various other embodiments, the pharmaceutical composition may be administered to the patient to reduce the risk of developing the disorder relating to vascular leak, vascular inflammation, and/or angiogenesis.

In some embodiments, the disorder relating to vascular leak, vascular inflammation, or angiogenesis may be selected from at least one of an ALI, influenza-induced acute respiratory distress, MDR pneumonia, sepsis, age-related macular degeneration, rheumatoid arthritis, cerebral malaria, multiple sclerosis, or cancer. In certain embodiments, the disorder relating to vascular leak, vascular inflammation, or angiogenesis may be a hemorrhagic fever virus infection selected from at least one of an Ebola virus infection, a Marburg virus infection, a hantavirus infection, or a dengue virus infection.

In various embodiments, the method may further include identifying a patient having a disorder relating to vascular leak, vascular inflammation, or angiogenesis, wherein the patient has enhanced ARF6 activity.

Another aspect of the disclosure relates to methods for treating a patient having, or at risk of developing, an ocular disorder. In some embodiments, the method may include administering to the patient an effective amount of a pharmaceutical composition including an ARF6 inhibitor, or a pharmaceutically acceptable salt of an ARF6 inhibitor. The pharmaceutical composition may further include a pharmaceutically acceptable carrier.

Another aspect of the disclosure relates to methods for treating a patient having malaria. In some embodiments, the method may include administering to the patient an effective amount of a pharmaceutical composition including an ARF6 inhibitor, or a pharmaceutically acceptable salt of an ARF6 inhibitor. The pharmaceutical composition may further include a pharmaceutically acceptable carrier. In various embodiments, the malaria may be a cerebral malaria, a severe malaria, or another suitable form of malaria.

In certain embodiments, the pharmaceutical composition may be administered to the patient to reduce a pathological effect or symptom of the ocular disorder. In certain other embodiments, the pharmaceutical composition may be administered to the patient to reduce the risk of developing the ocular disorder.

In various embodiments, the ocular disorder may be selected from at least one of age-related macular degeneration, diabetic retinopathy, retinopathy of prematurity, or macular edema.

Another aspect of the disclosure relates to methods for treating a patient having, or at risk of developing, an inflammatory disorder. In some embodiments, the method may include administering to the patient an effective amount of a pharmaceutical composition including an ARF6 inhibitor, or a pharmaceutically acceptable salt of an ARF6 inhibitor. The pharmaceutical composition may also include a pharmaceutically acceptable carrier.

In certain embodiments, administration of the pharmaceutical composition may reduce a pathological effect or symptom of the inflammatory disorder. In certain other embodiments, administration of the pharmaceutical composition may reduce the risk of developing the inflammatory disorder.

In various embodiments, the inflammatory disorder may be selected from at least one of ALI, acute respiratory distress syndrome, pneumonia, sepsis, rheumatoid arthritis, or multiple sclerosis.

Another aspect of the disclosure relates to methods for treating a patient having, or at risk of developing, a disorder treatable by inhibiting the activity of ARF6. In some embodiments, the method may include administering to the patient an effective amount of a pharmaceutical composition comprising an ARF6 inhibitor or a pharmaceutically acceptable salt of an ARF6 inhibitor. The pharmaceutical composition may also include a pharmaceutically acceptable carrier.

In certain embodiments, administration of the pharmaceutical composition may reduce a pathological effect or symptom of the disorder treatable by inhibition of the activity of ARF6. In certain other embodiments, administration of the pharmaceutical composition may reduce the risk of developing the disorder treatable by inhibiting the activity of ARF6.

In various embodiments of the methods disclosed herein, the patient may be a mammal such as a human. In some embodiments, the ARF6 inhibitor may be a prodrug of the ARF6 inhibitor. For example, the compound may include at least one of the compounds identified in Table 1 or 2, or in FIG. 8 or FIG. 9.

Another aspect of the disclosure relates to pharmaceutical compositions comprising a compound of Formula I or Formula II for use in any of the methods disclosed herein.

Another aspect of the disclosure relates to pharmaceutical compositions including one or more compounds including at least one of the compounds identified in Table 1 or Table 2 or pharmaceutically acceptable salts thereof. The pharmaceutical composition may also include a pharmaceutically acceptable carrier.

In some embodiments, the compound may be present in an amount effective to treat a patient having, or at risk of developing, a disorder relating to vascular leak, vascular inflammation, or angiogenesis. In certain embodiments, the compound may be present in an amount effective to treat a patient having, or at risk of developing, an ocular disorder. In various embodiments, the compound may be present in an amount effective to treat a patient having, or at risk of developing, an inflammatory disorder. In some embodiments, the compound may be present in an amount effective to treat a patient having, or at risk of developing, a disorder treatable by inhibiting the activity of ARF6. In certain embodiments, the compound may be present in an amount effective to treat a patient having malaria (e.g., cerebral malaria, severe malaria, etc.).

Another aspect of the disclosure relates to compounds having the chemical structures of, or identified in, Table 1 and Table 2. In some embodiments, the chemical structure of the compound may be at least one of NAV-B-NAV-AAR or at least one of NAV-B'-NAV-AAR'. In certain embodiments, the chemical structure of the compound may be NAV-B or NAV-AAR'.

Another aspect of the disclosure relates to prodrugs of the compounds identified herein, e.g., in Table 1 and Table 2. In some embodiments, the prodrug can be a lysine ester prodrug of NAV-U. In certain embodiments, the prodrug may be a phosphate ester of NAV-A, NAV-A', NAV-C, NAV-C', NAV-R, NAV-R', NAV-U, NAV-U', NAV-AD, NAV-AD', NAV-AAC, or NAV-AAC'. In some instances, the phosphate ester drug may be an active ARF6 inhibitor in its own right, and in other instances, the phosphate ester may be a prodrug requiring hydrolysis to its active parent. Other suitable prodrugs of the compounds identified herein (e.g., in Tables 1 and 2) are also within the scope of this disclosure.

EXAMPLES

To further illustrate these embodiments, the following examples are provided. These examples are not intended to limit the scope of the claimed invention, which should be determined solely on the basis of the attached claims.

Example 1—Target Validation

It has been demonstrated that the signaling pathway governed by the transmembrane cell surface receptor Robo4 and its agonists, the Slit glycoprotein family, stabilizes the vasculature during cytokine storm via inhibition of ARF6 (see Jones C A, et al. *Nature medicine*. 2008; 14:448-53; Jones C A, et al. *Nature cell biology*. 2009; 11:1325-31; and London N R, et al. *Science translational medicine*. 2010; 2:23ra19). ARF6 is a small GTPase of the Ras superfamily that, by virtue of its roles in endocytic trafficking and cell surface actin remodeling, makes it a player in regulation of cell-cell adhesion and cell motility (see Donaldson J G. *The Journal of biological chemistry*. 2003; 278:41573-6 and Schweitzer J K, et al. *Seminars in cell & developmental biology*. 2011; 22:39-47). ARF6 is activated by the exchange of intrinsically bound GDP for GTP that, depending on physiological context, can be catalyzed by a number of guanine nucleotide exchange factors (GEFs) (see Gillingham A K and Munro S. *Annual review of cell and developmental biology.* 2007; 23:579-611). It has been shown that ARF6 mediates cytokine-induced vascular hyperpermeability by promoting endocytosis of VE-cadherin (see Davis C T, et al. *Journal of immunology.* 2014; 192:6045-52 and Zhu W, et al. *Nature.* 2012; 492:252-5), a component of inter-endothelial adherens junctions with roles in the control of vascular integrity (see Komarova Y and Malik A B. *Annual review of physiology.* 2010; 72:463-93; Gavard J and Gutkind J S. *Nature cell biology.* 2006; 8:1223-34; London N R, et al. *Angiogenesis.* 2009; 12:149-58; and Dejana E, et al. *Journal of cell science.* 2008; 121:2115-22).

It has been demonstrated that ARF6 may represent a convergence point in the signaling pathways downstream from at least four receptors with documented roles in inflammation: IL-1R, IL-6R, TLR4, and VEGFR (see Davis C T, et al. *Journal of immunology.* 2014; 192:6045-52 and Zhu W, et al. *Nature.* 2012; 492:252-5) (see FIG. 1). Exposure of vascular endothelial cell cultures to the respective agonists, IL-1β, IL-6, LPS, or VEGF has been shown to induce: i) ARF6 activation; ii) endocytosis of VE-cadherin; and iii) an increase in paracellular permeability of the cell monolayer. In all cases, an ARF6-specific siRNA significantly inhibited both VE-cadherin internalization and cellular hyperpermeability. These vascular stabilization effects are not accompanied by a suppression of the NF-κB pathway, suggesting that inhibition of ARF6 can be anti-inflammatory without producing overt immunosuppression (see Davis C T, et al. *Journal of immunology.* 2014; 192:6045-52 and Zhu W, et al. *Nature.* 2012; 492:252-5).

Figure 2:
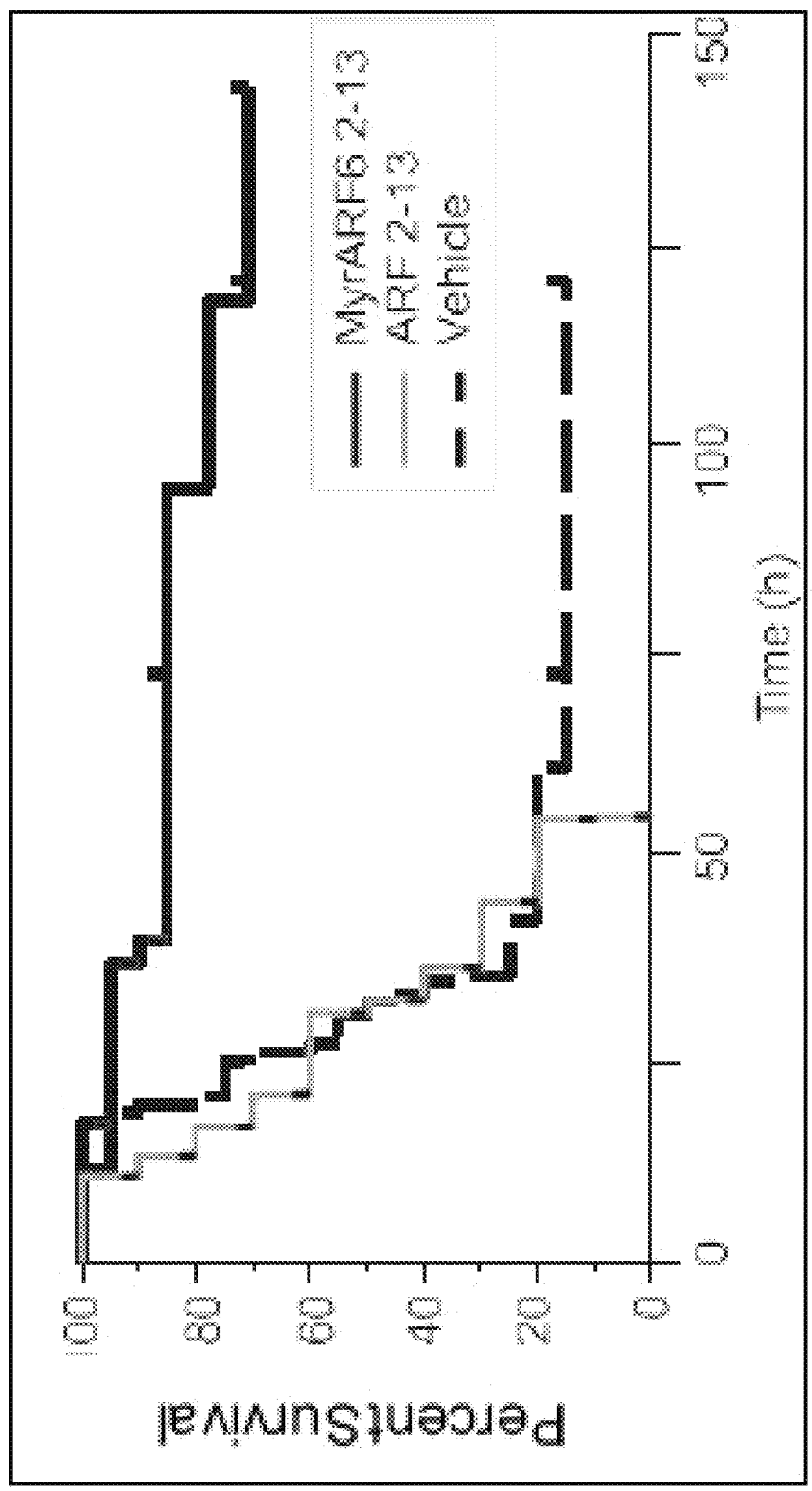
FIG. 2 is a graph showing that MyrARF6 2-13 peptide enhances survival during endotoxemia. Mice were administered a lethal dose of LPS (25 mg/kg IP) concurrently with 40 mmol/kg of peptide IV and monitored for survival.

ARF6 inhibition may be an effective approach to control cytokine-induced vascular permeability. Target validation has been supported by experiments using a peptide inhibitor of ARF6, and by experiments using mice with a conditional endothelial knockout of ARF6. A myristoylated peptide composed of amino acids 2-13 of ARF6 (MyrARF6 2-13), understood to inhibit ARF nucleotide exchange (see Randazzo P A, et al. *The Journal of biological chemistry.* 1995; 270:14809-15 and Choi W, et al. *Blood.* 2006; 107:3145-52), reduced ARF6 activation in HMVEC-D cells, reduced permeability across an endothelial monolayer, increased VE-cadherin at cell junctions, and prevented the leak of Evans blue dye from the blood into both lungs and kidneys (see Davis C T, et al. *Journal of immunology.* 2014; 192:6045-52). Further, MyrARF6 2-13 enhanced survival in a mouse model of LPS-induced endotoxic shock (see FIG. 2) (see Davis C T, et al. *Journal of immunology.* 2014; 192:6045-52). To further validate ARF6 as a target, it has been demonstrated that mice with a conditional knockout of ARF6 targeted to the endothelium are resistant to the effects of LPS administered into the lungs: the concentration of protein in the bronchoalveolar lavage fluid (BALF) of LPS-treated mice is reduced in these conditional knockout mice compared to that in wild-type mice (see Davis C T, et al. *Journal of immunology.* 2014; 192:6045-52).

Example 2—Efficacy of Small Molecule Inhibitors of ARF6

In support of target validation and to demonstrate feasibility of inhibiting ARF6 function with small molecule inhibitors, the in vivo efficacy of several such inhibitors was tested in a variety of animal models of vascular leak. First, in vivo efficacy was demonstrated of the ARF6 inhibitor, Compound No. 38 of International Application No. PCT/US2015/032720, in three distinct mouse models of retinal eye disease (VEGF-induced retinal permeability, laser-induced choroidal neovascularization, and oxygen-induced retinopathy). Second, efficacy was demonstrated of Compound No. 38 of International Application No. PCT/US2015/032720 in a murine model of collagen-induced arthritis (CIA). Mice were dosed once daily for 14 days in this CIA study at 30 mg/kg by intraperitoneal (IP) injection; a significant reduction in arthritic score was observed, with no signs of overt toxicity.

Figure 3:
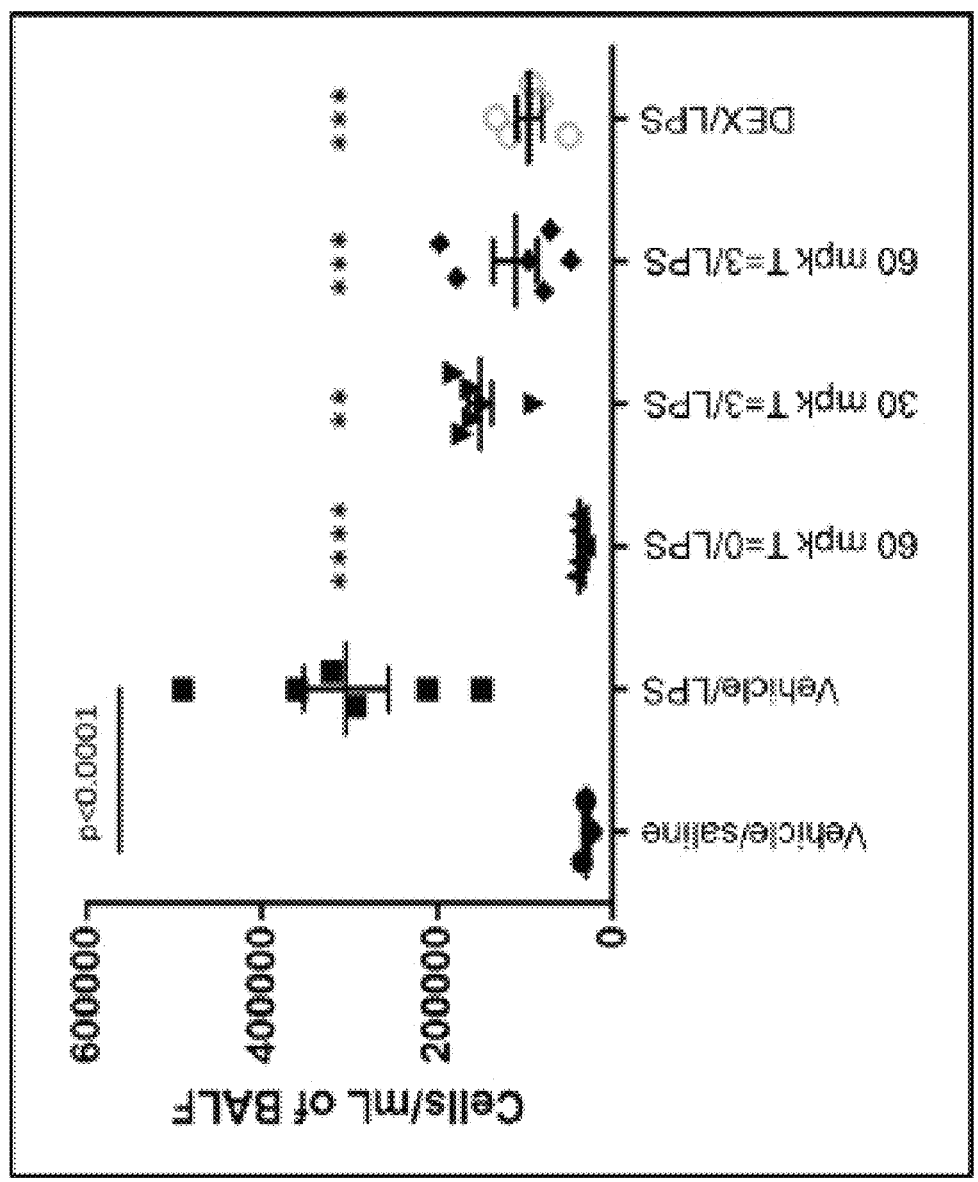
FIG. 3 is a graph showing the effect of NAV-A on bronchoalverolar lavage fluid (BALF) cell count in mouse LPS-induced acute lung injury (ALI) model. Administration of NAV-A at 60 mg/kg (T=0), 30 mg/kg (T=3), and 60 mg/kg (T=3) by intraperitoneal (IP) injection resulted in significant decreases in the total number of cells in BALF. **, $p<0.0001$; *, $p<0.001$; **, $p<0.01$. 1-way ANOVA followed by Tukey's multiple comparison test.

It has been demonstrated that several ARF6 inhibitors reduce vascular permeability in a mouse model of LPS-induced ALI (see FIG. 3 and Table 3). LPS was instilled into the trachea of anesthetized mice. ARF6 inhibitor was given by IP injection at a dose of either 30 or 60 mg/kg, either immediately after LPS instillation (T=0) or three hours after LPS (T=3). The efficacy endpoints were total cell counts and total protein in BALF. All studies were conducted using vehicle negative controls and dexamethasone (5 mg/kg IP at T=0 and 6) as a positive control. Data were analyzed by 1-way ANOVA followed by Tukey's multiple comparison test (GRAPHPAD PRISM® software, version 6.05). The effect of NAV-A is illustrated in FIG. 3; administration of NAV-A at 60 mg/kg (T=0), 30 mg/kg (T=3), and 60 mg/kg (T=3) resulted in significant decreases in the total number of cells in BALF. Further experiments demonstrated that greater than 95% of these cells were neutrophils. Reductions in BALF total protein were also observed.

TABLE 3

Effect of ARF6 Inhibitors on BALF Cell Count and BALF Protein

| BALF CELL COUNT | | | | | |
|---|---|---|---|---|---|
| Compound | 30 mg/kg T = 0 | 60 mg/kg T = 0 | 30 mg/kg T = 3 | 60 mg/kg T = 3 | DEX |
| Cpd. No. 38**** | 49 ± 13% *** | 61 ± 4% *** | 26 ± 3% ** | 64 ± 4% *** | 63 ± 4% *** |
| Cpd. No. 4**** | 52 ± 9% *** | 34 ± 4% *** | 66 ± 9% *** | 44 ± 11% *** | 59 ± 5% *** |
| NAV-A | 57 ± 9% *** | 95 ± 4% *** | 55 ± 3% *** | 91 ± 1% *** | 70 ± 7% *** |
| Cpd. No. 14**** | 39 ± 3% * | 48 ± 25% ** | 7 ± 7% | 47 ± 17% ** | 64 ± 9% *** |
| Cpd. No. 40**** | 45 ± 11% ** | 84 ± 4% *** | 53 ± 10% ** | 82 ± 8% *** | 74 ± 5% *** |

| BALF PROTEIN | | | | |
|---|---|---|---|---|
| 30 mg/kg T = 0 | 60 mg/kg T = 0 | 30 mg/kg T = 3 | 60 mg/kg T = 3 | DEX |
| 20 ± 10% | 61 ± 9% *** | 7 ± 4% | 60 ± 8% *** | 48 ± 7% *** |
| 19 ± 8% | 33 ± 17% * | 27 ± 5% * | 20 ± 8% * | 58 ± 13% *** |
| 36 ± 13% | 46 ± 24% | 23 ± 12% | 55 ± 6% ** | 43 ± 9% *** |

TABLE 3-continued

Effect of ARF6 Inhibitors on BALF Cell Count and BALF Protein

| 8 ± 5%  | 56 ± 19% ** | 5 ± 5%   | 40 ± 5% ** | 42 ± 10% ** |
| 27 ± 8% | 49 ± 5% *** | 13 ± 13% | 30 ± 8% *  | 37 ± 6% **  |

Individual mouse data points across several identical experiments were pooled and then analyzed by 1-way ANOVA and Tukey's test.
Data are presented as mean ± SEM percent reduction in LPS-induced increases in BALF cell counts and BALF protein.
At least three independent experiments were conducted for each condition, and sample size for each dose group within each experiment was ≥3 mice.
*, $p < 0.05$;
**, $p < 0.01$;
***, $p < 0.001$ compared to LPS treatment;
****Compound Nos. from International Application No. PCT/US2015/032720.

Figure 4:
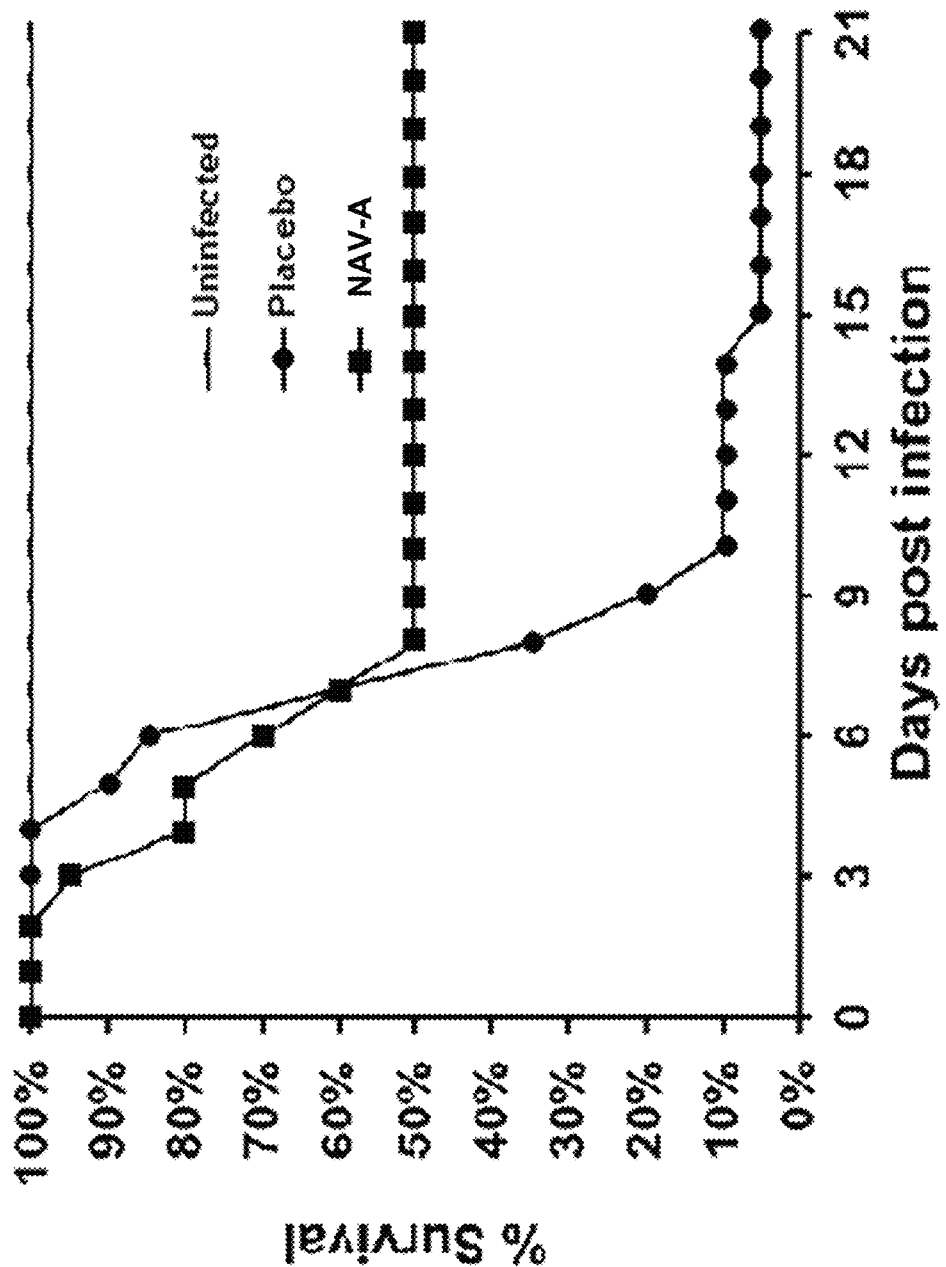
FIG. 4 is a graph showing that treatment with NAV-A IP for seven days significantly improves survival of neutropenic mice infected with *Acinetobacter baumannii* (AB). NAV-A: 50% survival, $p<0.05$ compared to vehicle placebo. n=22 mice per treatment group.

Studies have demonstrated significant activity of the small molecule inhibitors of ARF6 in a mouse model of MDR Gram-negative bacterial (GNB) infection. Briefly, CD-1 male mice were made neutropenic with 200 mg/kg cyclophosphamide and 250 mg/kg cortisone acetate (in 0.05% Tween 80) on Days −2 and +3. On Day 0, neutropenic mice were infected with Acinetobacter baumannii (AB) HUMC1 (virulent strain; see Luo G, et al. J Antimicrob Chemother. 2012; 67:1439-45 and Luo G, et al. PloS one. 2012; 7:e29446) via inhalation. Treatment with "NAV-" compound was initiated at three hours post infection. As shown in FIG. 4, once-daily injection of NAV-A at 30 mg/kg IP led to a significant improvement in survival compared to treatment with vehicle (50% survival, p<0.05 compared to vehicle placebo). The mice appeared healthy with normal weight gain.

Figure 5:
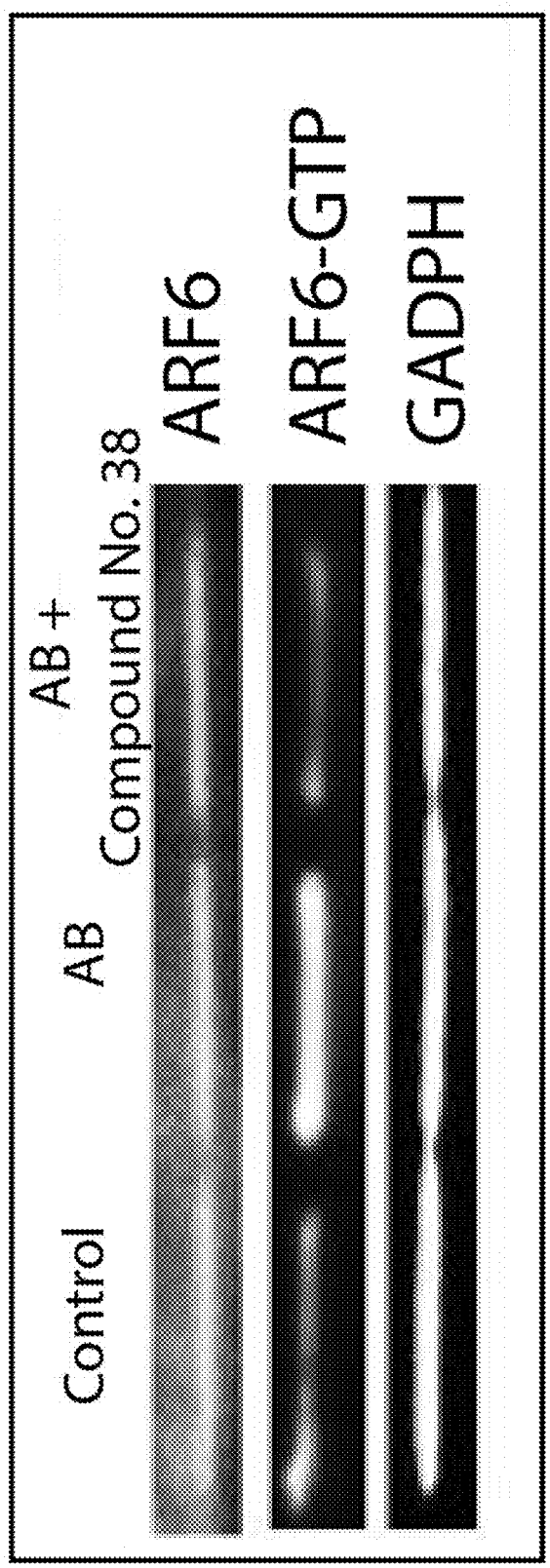
FIG. 5 is a series of images showing that infection of human umbilical vein endothelial cells (HUVECs) with AB increased levels of active ARF6-GTP. ARF6 activation was blocked by Compound No. 38 of International Application No. PCT/US2015/032720.

It has also been demonstrated that infection of human umbilical vein endothelial cells (HUVECs) with AB can lead to activation of ARF6, as measured by the amount of ARF6-GTP in a pulldown assay. Further, this activation of ARF6 was inhibited by treatment of HUVECs with 20 μM of Compound No. 38 of International Application No. PCT/US2015/032720, another small molecule ARF6 inhibitor (see FIG. 5).

Example 3—NAV-B, a Water Soluble Prodrug of NAV-A

Some of the small molecule inhibitors of ARF6, disclosed herein, have limited aqueous solubility, which can necessitate use of complex solvents, co-solvents, and/or excipients for formulation. The formulation used in most studies described above was dimethylacetamide (DMA)/PEG300 (10:90 v/v). Therefore, an effort was initiated to synthesize water soluble prodrugs of the effective ARF6 inhibitors. Prodrugs can be chemically modified versions of pharmacologically active agents (parent drugs), which are designed to release parent drug upon chemical or enzymatic degradation in vivo (see Rautio J, et al. Nature reviews Drug discovery. 2008; 7:255-70; Huttunen K M, et al. Pharmacol Rev. 2011; 63:750-71; and Zawilska J B, et al. Pharmacological reports: PR. 2013; 65:1-14). Approximately 20% of all small molecule drugs approved from 2000 to 2008 were prodrugs. The use of prodrugs has been shown to overcome poor water solubility (see Stella V J and Nti-Addae K W. Advanced drug delivery reviews. 2007; 59:677-94).

Figure 6:
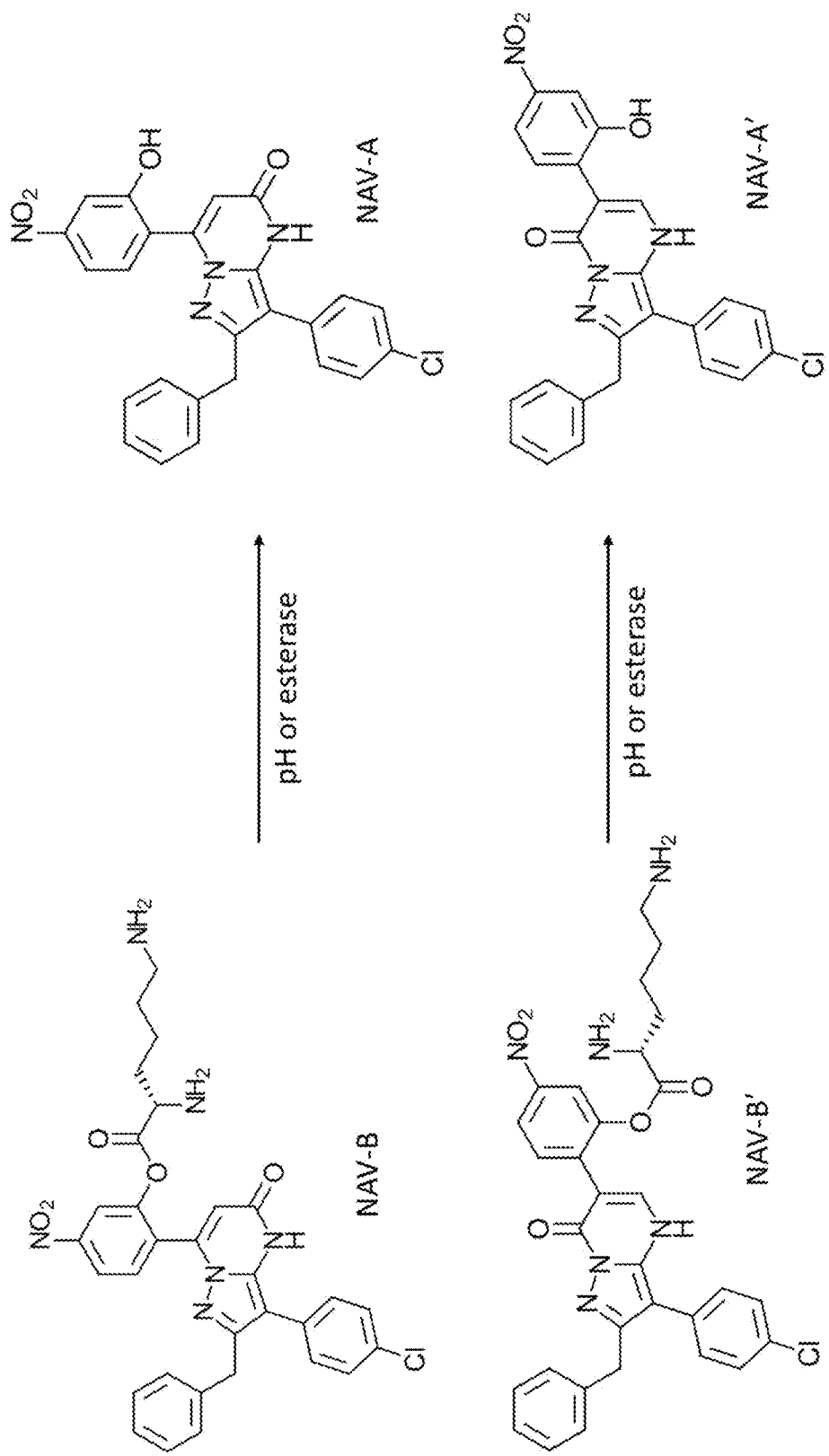
FIG. 6 shows the chemical structures of NAV-B (lysine prodrug) and its parent NAV-A, and of NAV-B' (lysine prodrug) and its parent NAV-A'.

The structure of NAV-B, the lysine prodrug of NAV-A, is shown in FIG. 6. NAV-B as the dihydrochloride salt is soluble in acidic aqueous media at concentrations greater than 50 mg/mL. The vehicle used in the in vivo studies described below was either 5% dextrose in water (D5W) with 0.1% Tween 80 in water, pH ~4.5, or 0.9% sodium chloride (normal saline).

Figure 7:
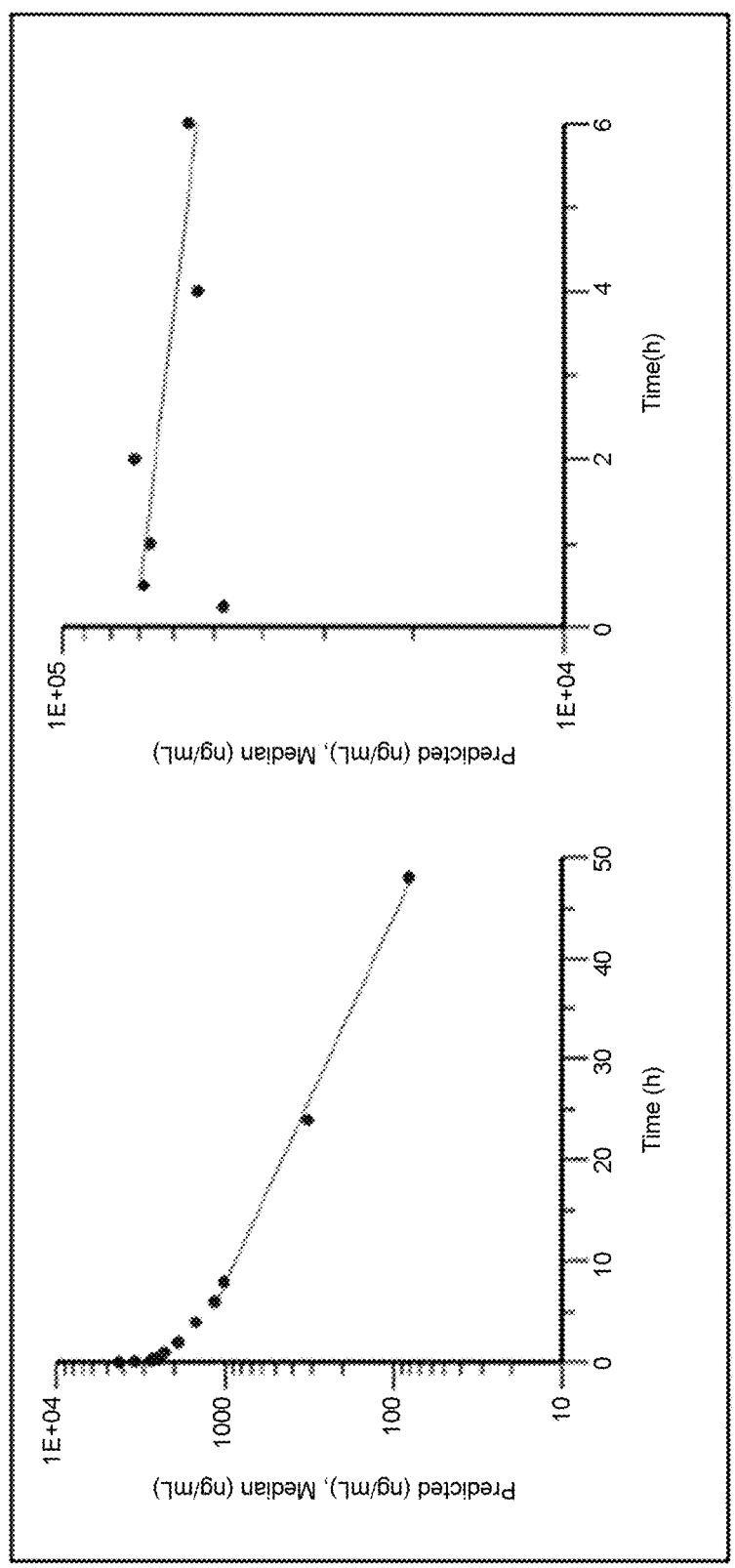
FIG. 7 is two graphs showing plasma concentration versus time profiles of NAV-A following intravenous (IV) dosing of NAV-B to rats (left) and IP dosing of NAV-B to mice (right). Administration of NAV-B provided excellent exposure of NAV-A. The following pharmacokinetic (PK) parameters were determined following IV dosing in rats: terminal half-life, 10.9 hr; volume of distribution, 383 mL/kg; clearance, 25 mL/kg/hr.

The PK profile of NAV-A was determined following intravenous (IV) and intraperitoneal (IP) administration of prodrug NAV-B to rats and mice, respectively. FIG. 7 (left panel) shows the plasma concentration versus time profile of NAV-A following a lateral tail vein IV injection of NAV-B at the dose of 1.4 mg/kg (equivalent to NAV-A at 1 mg/kg). In this experiment, only the appearance and PK profile of NAV-A was followed, using an established LC/MS method. Administration of NAV-B provided excellent exposure of NAV-A, similar to what was observed previously after dosing NAV-A itself. Of note was the very rapid appearance of NAV-A in plasma of the rats receiving NAV-B IV; the highest plasma concentration observed was at five minutes post-dose, the first time point measured. The right panel of FIG. 7 shows the plasma concentration versus time profile of NAV-A following IP administration of 43 mg/kg of NAV-B (equivalent to 30 mg/kg of NAV-A). Although the time course of this experiment was relatively short, high and sustained plasma levels of NAV-A can be seen across a six-hour period after dosing. Near peak plasma levels of NAV-A were observed within 30 minutes.

The in vivo efficacy of NAV-B was evaluated in a murine LPS-induced ALI model. Administration of NAV-B at 43 mg/kg IP at T=0 resulted in a 70% reduction in BALF cell count, similar to that produced by 30 mg/kg NAV-A at T=0 (see Table 2). Efficacy in the LPS-induced ALI model confirms the conversion of NAV-B in vivo to the active parent drug NAV-A.

Example 4—NAV-AAR', a Water Soluble ARF6 Inhibitor

The structure of NAV-AAR' is shown in Table 2. NAV-AAR' is an ARF6 inhibitor with an IC50 value of approximately 1-2 μM. NAV-AAR' is also a substrate for alkaline phosphatase, thereby being metabolized to an active metabolite NAV-AAC'. NAV-AAR' is highly soluble in aqueous media at concentrations up to 50 mg/mL, and is stable in solution for up to 4 months at room temperature, protected from light.

Figure 12:
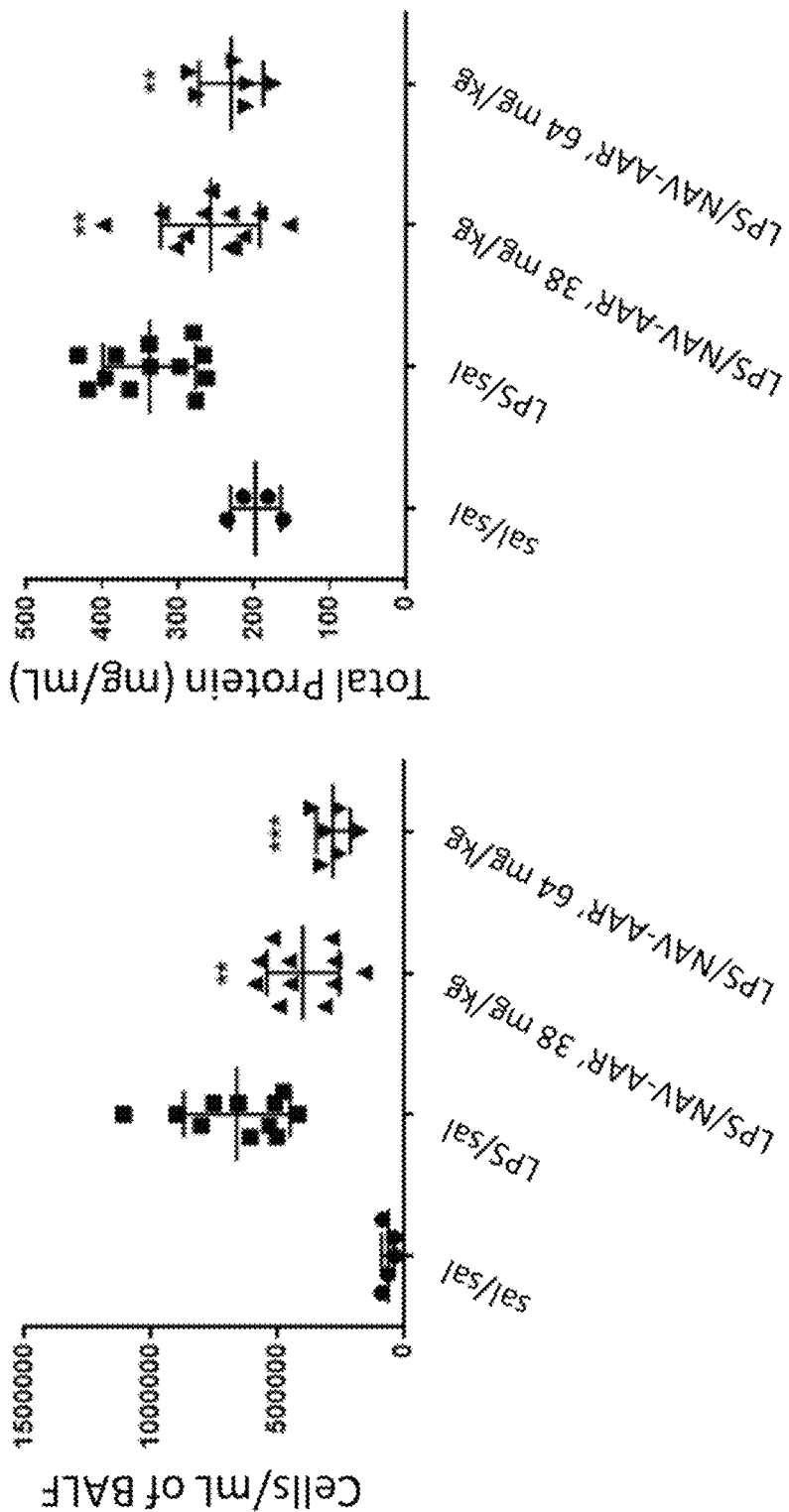
FIG. 12 shows decrease in number of nucleated cells and total protein concentration in BALF in LPS-induced ALI mice treated with NAV-AAR'. , $p<0.01$ compared to LPS/sal. *, $p<0.001$ compared to LPS/sal. One-way ANOVA with Tukey's test for multiple comparisons.
Figure 13:
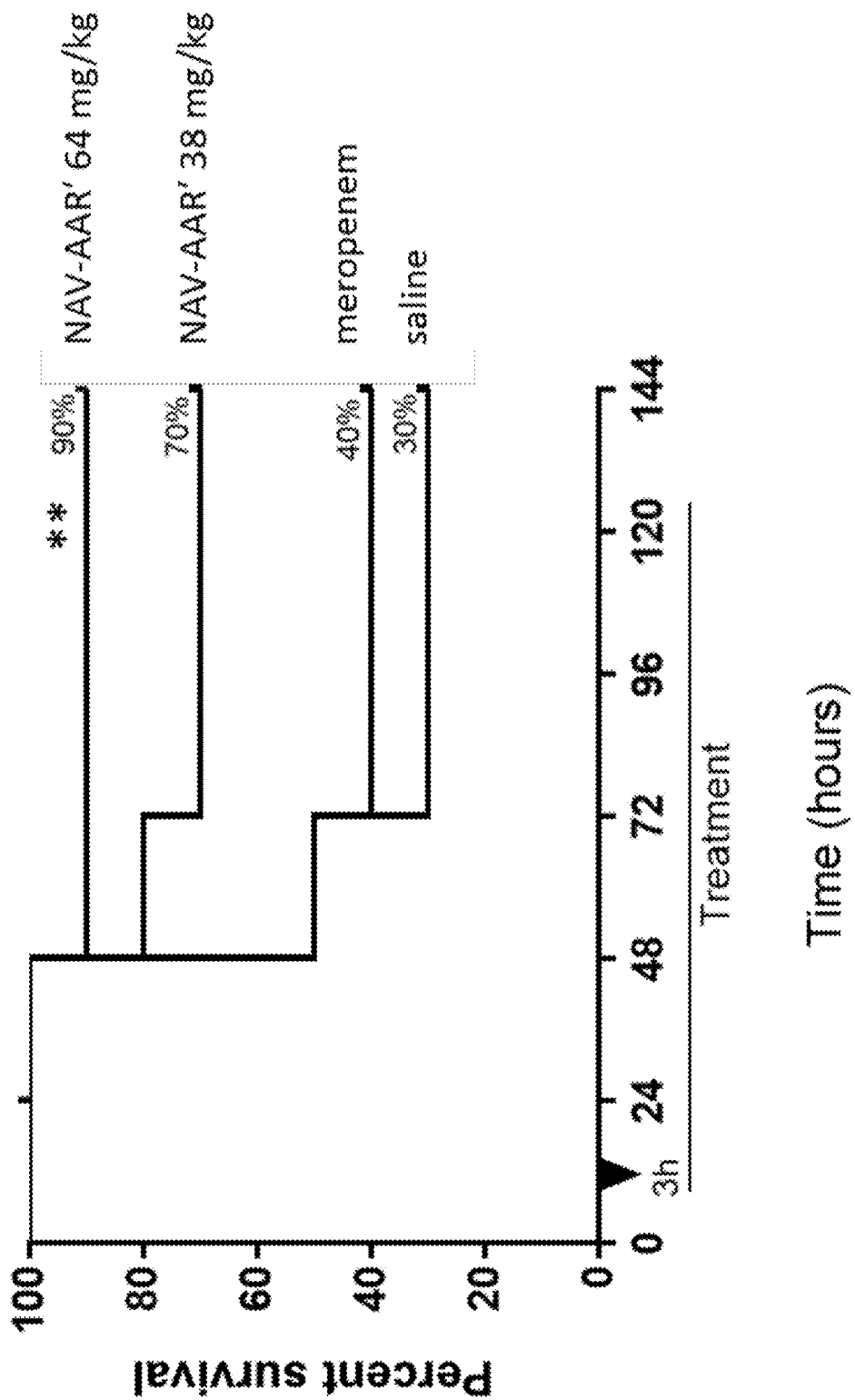
FIG. 13 shows increase in survival in mice with multi-drug-resistant (MDR) *Pseudomonas aeruginosa* pneumonia treated with NAV-AAR'. **, p<0.01 compared to vehicle.

The effect of NAV-AAR' in the mouse model of LPS-induced ALI is shown in FIG. 12. Administration of NAV-AAR' at 38 mg/kg or 64 mg/kg by intravenous injection resulted in significant reductions in the number of total cells and protein concentration in BALF. NAV-AAR' is also active in a multidrug-resistant Pseudomonas aeruginosa (PA) mouse model of pneumonia. FIG. 13 illustrates the effect of NAV-AAR' to improve survival in mice at dose levels of 38 and 64 mg/kg. NAV-AAR' was administered by subcutaneous injection once daily for 6 days. The antibiotic meropenem was ineffective against MDR PA in this model.

Figure 8:
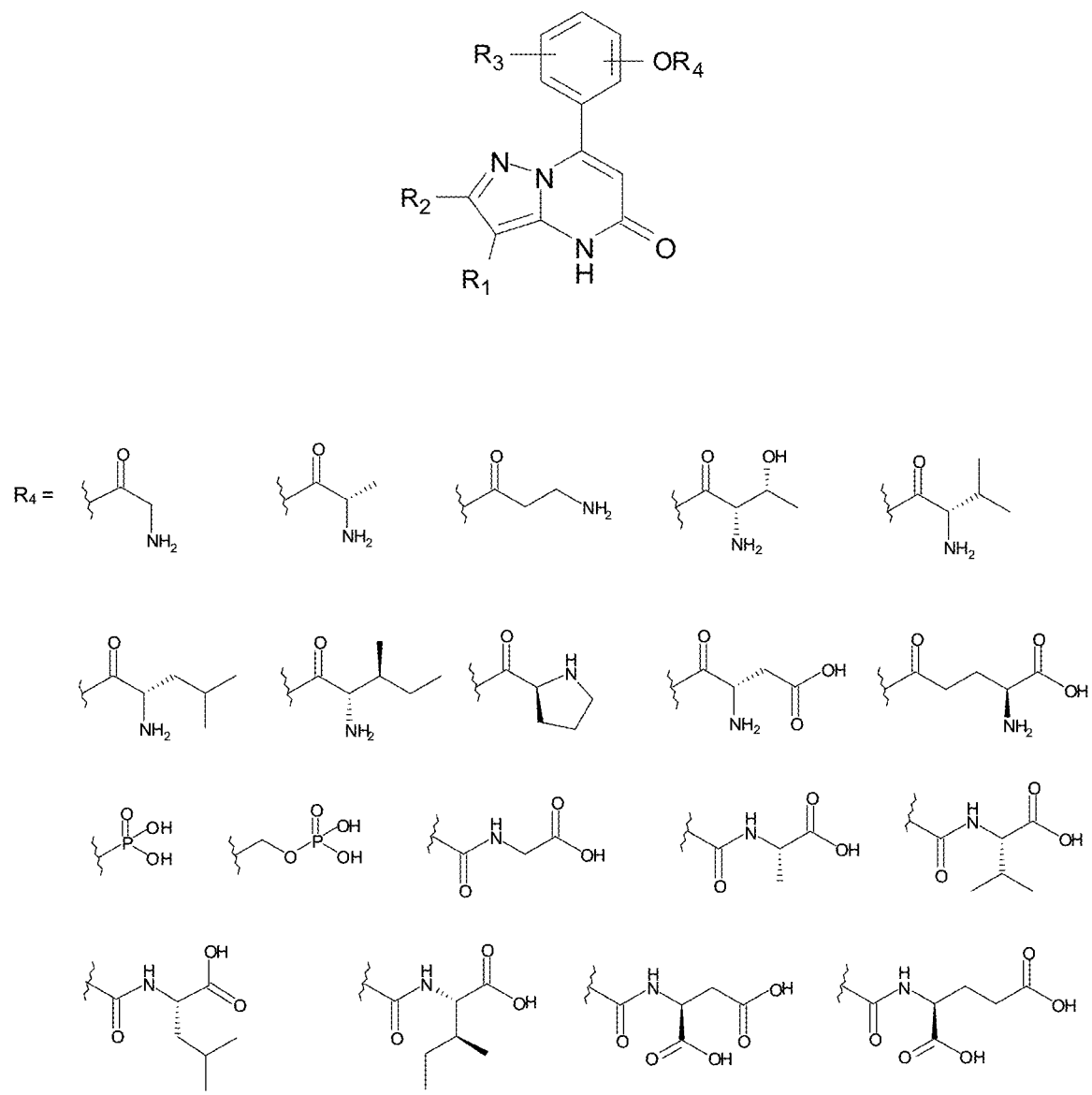
FIG. 8 shows examples of prodrugs of NAV-A and other ARF6 inhibitors.
Figure 9:
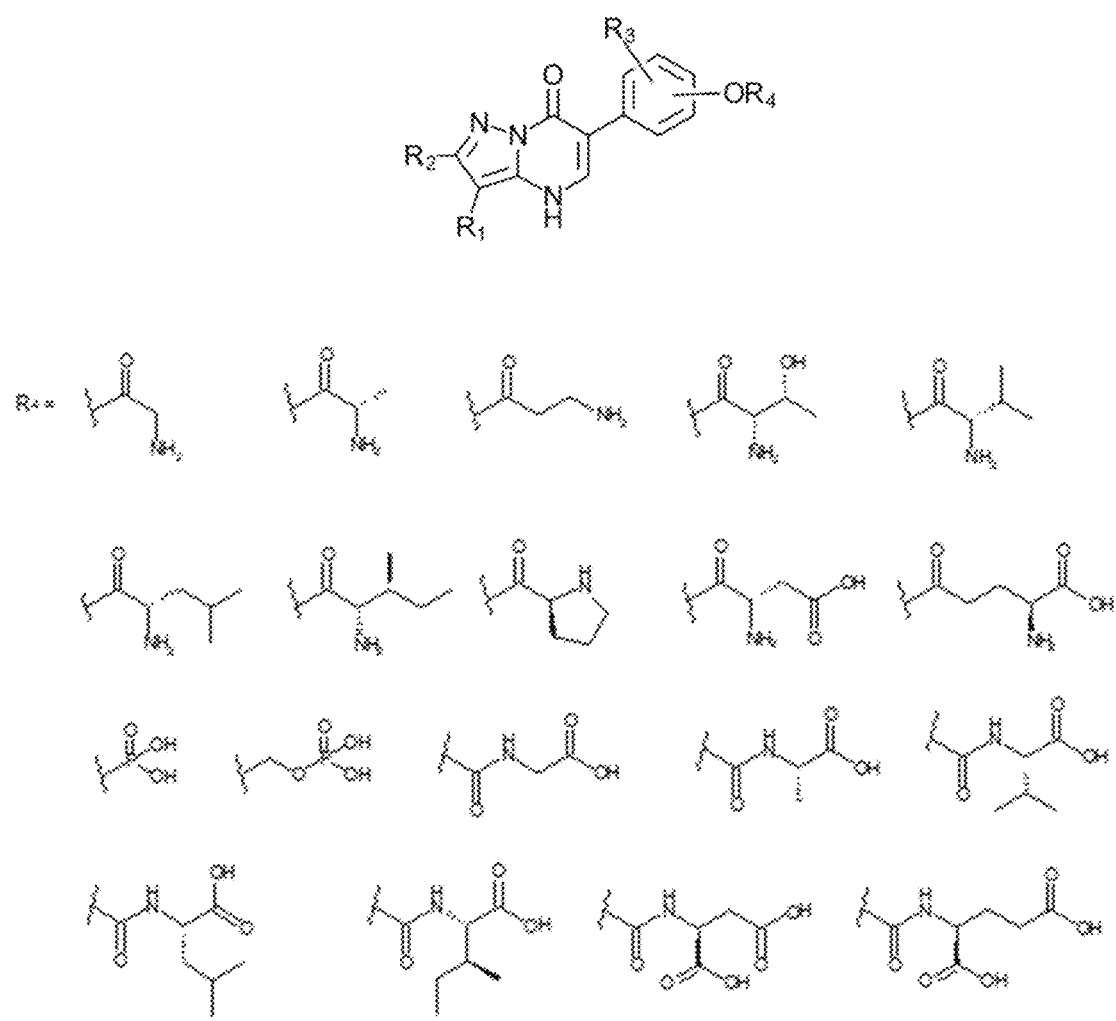
FIG. 9 shows examples of prodrugs of NAV-A' and other ARF6 inhibitors.

Example 5—Synthesis and Characterization of Water Soluble Prodrugs of NAV-A and Other ARF6 Inhibitors Prodrugs of NAV-A, of NAV-A', and other ARF6 inhibitors may be synthesized, including a phosphate ester prodrug, several amino acid and dipeptide prodrugs, as well as prodrugs with other functionalities. A few examples of potential prodrugs and their pharmaceutically acceptable salts to be synthesized are illustrated in FIG. 8 and FIG. 9. The following characteristics of these prodrugs can be evaluated: intrinsic ARF6 inhibitory activity measured in a biochemical assay as disclosed herein; aqueous solubility in vehicles such as sterile water for injection, normal saline, phosphate buffered saline, and D5W; aqueous solubility and stability in solution as a function of pH; and rate and extent of conversion to parent NAV-A (FIG. 8) or NAV-A' (FIG. 9) in mouse, rat, dog, monkey, and human serum.

Example 6—Rodent PK and Confirmation of In Vivo Efficacy in Mouse LPS-induced ALI Model Prodrugs of NAV-A and other ARF6 inhibitors synthesized in Example 5 can be evaluated in rodent PK studies. IV PK in rats can provide parameters such as half-life, clearance, and volume of distribution. Rats may be preferred for IV PK studies, as one can obtain multiple blood draws from a catheterized rat over a 24- to 48-hour period, thereby minimizing the number of animals required. This subset of prodrugs can also be tested in mice with IP dosing. IP PK can provide additional parameters (maximum blood level, time to maximum blood level, and overall exposure) that may be used to determine appropriate dose levels for LPS-induced ALI studies. Plasma levels of prodrug (if possible) and parent may be determined using LC/MS. Sensitive bioanalytical methods have been developed for several small molecule ARF6 inhibitors, including NAV-A. PK data can be analyzed using PHOENIX WINNONLIN® software. Mouse LPS-induced ALI studies may then be conducted using prodrugs. Efficacy in this model may confirm the systemic exposure of the active parent drug and therefore complement the PK data.

Sprague-Dawley rats (300-350 g) can be anesthetized, and venous and arterial catheters can be placed for drug infusion and blood collection, respectively. Prodrug can be administered at a dose equivalent to 1 mg/kg of its respective parent by slow (60 second) IV push to six rats (three male/three female). Blood can be collected at 11 time points over a 48-hour period for determination of drug levels: 5 minutes, 10 minutes, 15 minutes, 30 minutes, 1 hour, 2 hours, 4 hours, 6 hours, 8 hours, 24 hours, and 48 hours.

For IP PK studies, prodrug can be administered to C57BL/6 mice by IP injection at doses equivalent to 10, 30, and 60 mg/kg of its respective parent. Blood can be collected at the following time points for analysis: 15 minutes, 30 minutes, 1 hour, 2 hours, 4 hours, 8 hours, 24 hours, and 48 hours. Sample size may be six mice per time point (three male/three female). Two blood samples can be collected from an individual mouse (one of these being at time of terminal sacrifice) as this reduces by half the number of animals required.

For the ALI studies, LPS can be administered into the trachea of anesthetized C57BL/6 mice. Immediately thereafter (T=0), prodrug can be injected IP; three doses of each prodrug can be tested (e.g., doses equivalent to 10, 30, and 60 mg/kg of parent). BALF can be collected from anesthetized animals 24 hours after injection of LPS and analyzed for total cell count and total protein. Four males and four females (total n=8) can be randomized to blinded treatment and control groups. A power analysis run at 80% power to detect a treatment effect size of 1.5 at a significance of 0.0083 (0.5÷6, due to six treatment groups) can calculate a sample size of eight with actual power of 83% (G*POWER® software, Version 3.1.9.2).

Figure 10A:
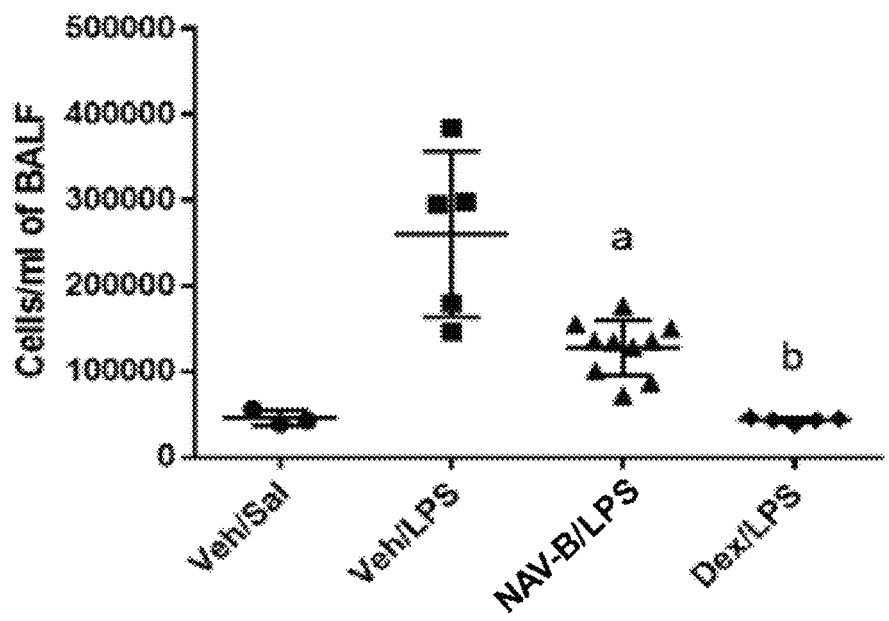
FIG. 10A is a graph showing reduction in LPS-induced BALF cell count by NAV-B, 42.75 mg/kg IP at T=0, equivalent to 30 mg/kg of parent NAV-A. a, 62% reduction, $p<0.001$; b, 100% reduction, $p<0.0001$.

In LPS-induced ALI experiments, a significant effect of NAV-B (42.75 mg/kg IP, equivalent to 30 mg/kg of parent NAV-A) was observed in reducing concentrations of cells (see FIG. 10A) and protein in BALF, similar to the effect observed with parent NAV-A.

Example 7—Mouse *Acinetobacter baumannii* (AB) Pneumonia

Prodrugs may advance from Example 6 to the studies of Example 7. It has been demonstrated that AB virulence and lethality in mice can be directly attributed to the shedding of LPS and the activation of the TLR4 pathway (see Lin L, et al. *mBio*. 2012; 3.). Further, it has been demonstrated that the ARF6 inhibitor, NAV-A, showed significant improvement in survival in a murine model of AB pneumonia (see FIG. 5).

Mice can be made neutropenic by injecting them with cyclophosphamide (200 mg/kg IP) and cortisone acetate (250 mg/kg, subcutaneously) on day −2 and +3 relative to infection. To induce AB pneumonia, neutropenic mice can be infected by aerosolizing AB into an inhalational chamber for one hour through a nebulizer as previously described (see Luo G, et al. *J Antimicrob Chemother*. 2012; 67:1439-45). Dosing and frequency of treatment can be dictated by the PK and ALI studies conducted in Example 6. Placebo mice can receive vehicle. Another group of mice infected and treated with colistin (2.5 mg/kg given twice daily via IP injection) can serve as a positive control, since this antibiotic has been shown to be protective against AB HUMC1 (see Luo G, et al. *J Antimicrob Chemother*. 2012; 67:1439-45). Treatment can begin three hours after infection and continue through Day +7, and survival of mice (the primary endpoint) can be followed for 28 days post-infection. Each group may comprise 10 mice and each experiment may be repeated once (for a total of 20 mice per treatment group) to detect a three-day difference in survival by the Log Rank test ($\alpha=0.05$).

As secondary end points, the effect can be determined of the inhibitors on the tissue bacterial burden and histopathology (see Luo G, et al. *J Antimicrob Chemother*. 2012; 67:1439-45) in kidneys, lungs, and spleen. Protective doses of the inhibitors can be administered as above, and at a selected time interval (determined from the survival studies), mice can be sacrificed and target tissues harvested for quantitative culturing and histopathological examination. Further, the effect of protective doses of the inhibitors on inflammatory cytokine profiles during infection can be determined in blood (by cardiac puncture after sedation with a mixture of ketamine and xylazine) and in whole organs, because this technique measures the cytokine response of all cell types present at the site of infection. Hence, this technique may allow a global assessment of the host cytokine response to the organism and to the ARF6 inhibitor treatment, rather than focusing on an individual cell type. Cytokine levels, including IFN-γ, IL-1β, IL-6, IL-10, IL-12, TNF-α, and KC, in serum or target organs, can be determined using MSD Multi-Spot assay (MESO SCALE™) per the manufacturer's instructions (see Lin L, et al. *mBio*. 2012; 3). Additionally, myeloperoxidase (MPO) in target organs can be determined. Finally, serum LPS can be measured by using Limulus amebocyte lysate, Chromogenic Endotoxin Quantitation Kit (CHARLES RIVER™) (see Luo G, et al. *PloS one*. 2012; 7:e29446). All these studies may be conducted on the same mice used for the CFU studies to reduce the number of animals used and to power the results for better correlation of mouse-to-mouse data. As above, 10 mice/group (from two experiments) can be used to achieve an 80% power to detect a one log difference in CFU or double the change in other parameters ($\alpha=0.05$) (see Spellberg B, et al. *Infection and immunity*. 2003; 71:5756-64).

Figure 10B:
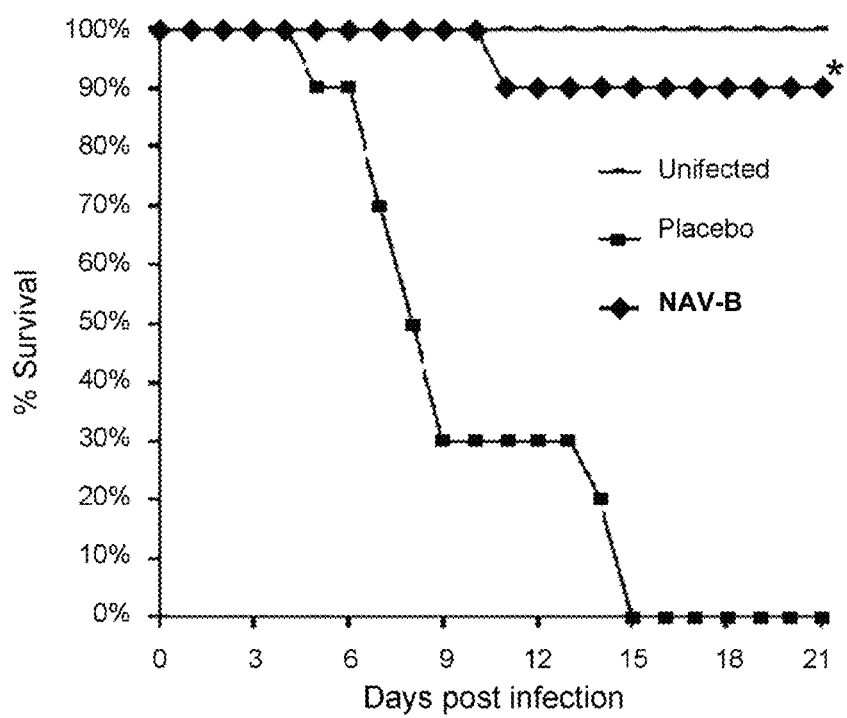
FIG. 10B is a graph showing 90% survival of AB infected mice treated with NAV-B, 42.75 mg/kg IP once daily for 7 days. *, $p<0.01$ compared to placebo.

In another experiment, NAV-B (42.75 mg/kg IP once daily for seven days) resulted in a highly significant 90% survival rate in mice with *Acinetobacter baumannii* (AB) pneumonia (see FIG. 10B). This dose of NAV-B is equivalent to dosing NAV-A at 30 mg/kg. The 90% survival observed with NAV-B is superior to the 50% survival noted previously with NAV-A itself. Without being bound by any one particular theory, the greater efficacy seen with NAV-B may be due to use of normal saline as drug vehicle rather than DMA/PEG300 required to solubilize NAV-A. No outcome measures specific to lung injury, e.g., histologic evidence of lung injury, inflammation, alteration of the alveolar capillary barrier, or physiologic dysfunction, were measured in this study; the only outcome measured was survival.

Example 8—Analysis in Cerebral Malaria Model

Figure 11:
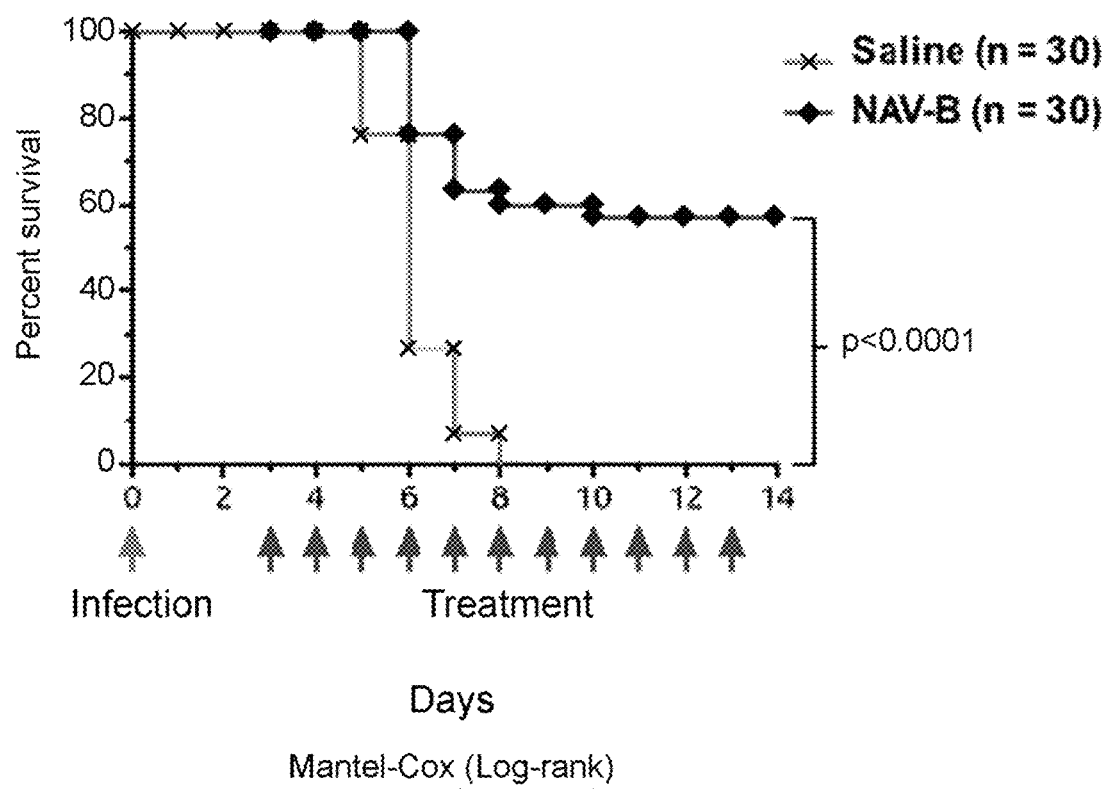
FIG. 11 is a graph depicting combined survival of malaria-infected mice treated with NAV-B in three independent experiments. Mice were infected on Day 0 and then treated with either saline or NAV-B once daily for 11 days. Treatment with NAV-B resulted in a significant improvement in survival.

NAV-B reduced mortality at 14 days post-infection, while no vehicle-treated mice survived beyond day 8 in a mouse model of cerebral malaria (CM) (see FIG. 11). Mice were infected with *Plasmodium berghei* ANKA on day 0. Treatment was initiated on day 3. Groups consisted of vehicle control (administered IP daily for 11 days) and NAV-B-treated mice (administered IP, 42.75 mg/kg daily, for 11 days). Surviving mice were sacrificed on day 14.

Example 9—Chemical Synthesis and Purification of Example Compounds

All reactions were performed in flame-dried or oven-dried glassware under a positive pressure of dry nitrogen or dry argon and were stirred magnetically unless otherwise indicated. All solvents and chemicals were purchased from standard commercial vendors and used as received unless otherwise noted. Any necessary preparations not referenced or described herein were facile and known to one of ordinary skill in the art. Yields are not optimized. The chemical names were generated using the SYMYX® DRAW™ 3.1 chemical drawing program, available from MDL INFORMATION SYSTEMS™, a division of SYMYX® TECHNOLOGIES, Inc. (Santa Clara, Calif.).

Reactions were monitored by thin layer chromatography (TLC) using 0.25 mm silica gel 60 $F_{254}$ plates purchased from EMD MILLIPORE™. Purification was performed with TELEDYNE ISCO™ COMBIFLASH® TLC retention factor (Rf). $^1$H nuclear magnetic resonance spectroscopy (NMR) spectra were recorded on a VARIAN MERCURY™ 400 MHz instrument. Proton chemical shifts are expressed in parts per million (ppm) relative to TMS and calibrated using residual undeuterated solvent as an internal reference. Mass spectra were recorded on AGILENT™ Q-TOF paired with an AGILENT™ 1290 INFINITY high performance liquid chromatography (HPLC) system. Compound purity was determined by an AGILENT™ HP1050 instrument with 4.6 mm×150 mm XTERRA® MS $C_{18}$ 3.5 µm column and UPCHURCH® 5 µm precolumn 24×12 mm. The flow rate was 1.2 mL/minute, and the injection volume was 5 µL. HPLC conditions were as follows: mobile phase A, HPLC grade water (0.1% trifluoroacetic acid (TFA)); mobile phase B, HPLC grade acetonitrile (0.1% TFA); UV detector, 250 nm; 95% A/5% B to 0% A/100% B in 10 minutes, 100% B in 10-11 minutes, 100% B to 95% A/5% B in 11-13 minutes, 95% A/5% B in 13-15 minutes.

Example 10—Methods of Synthesis: Schemes I and II

General methods, according to some embodiments, for the preparation of the compounds of the present disclosure are provided in this and other Examples below.

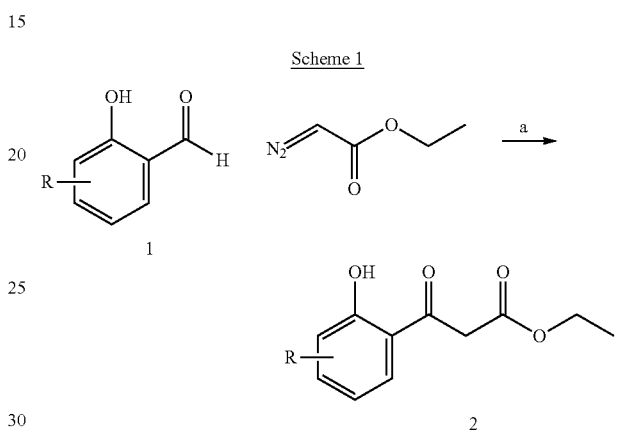

Reagents and conditions: dichloromethane (DCM), NbCl$_5$, room temperature (rt), and 1-18 hours. Compound 2 may be synthesized by reacting compound 1 with ethyl diazoacetate in toluene or ethyl diazoacetate in DCM using NbCl$_5$ as a catalyst in an organic solvent.

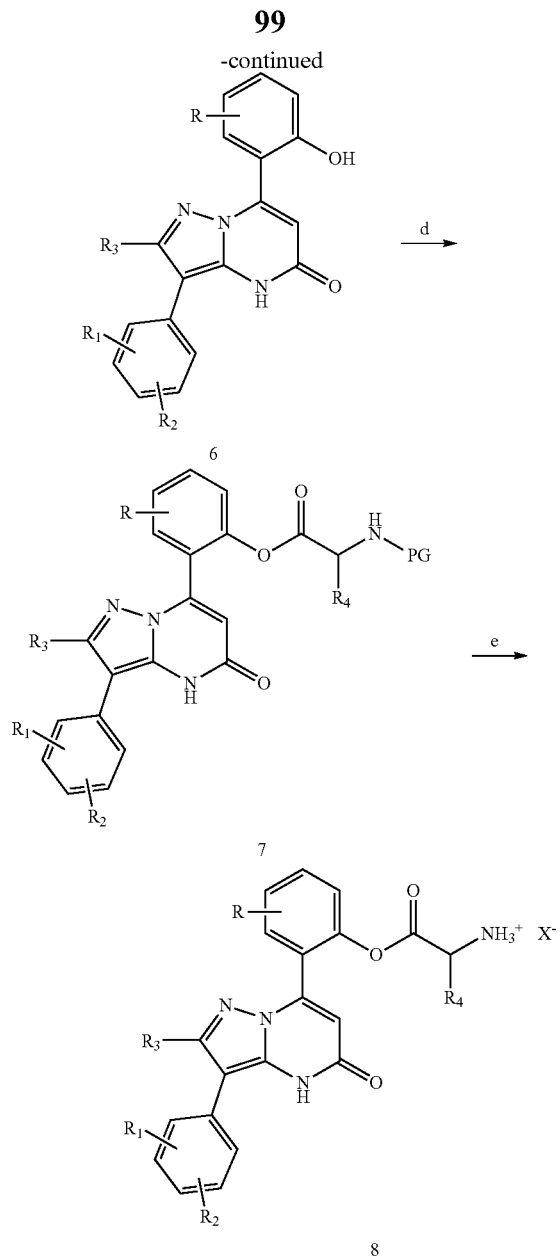

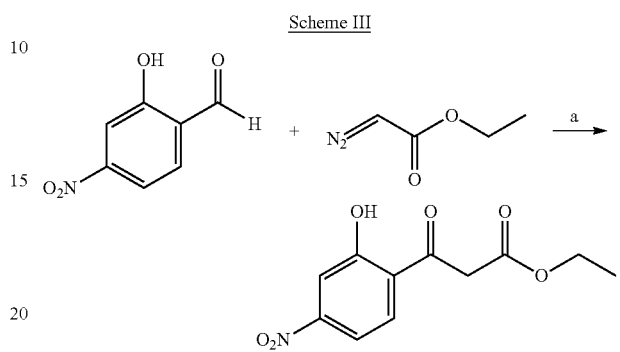

prepared under standard conditions); and v) deprotection of the protecting groups using known methods to provide compound 8.

Example 11—Scheme III

Scheme III

Reagents and conditions: a) DCM, NbCl$_5$, rt, and 16 hours.

Detailed procedure of Scheme III (intermediate 1):

Intermediate 1

Ethyl 3-(2-hydroxy-4-nitro-phenyl)-3-oxo-propanoate

To a solution of 2-hydroxy-4-nitro-benzaldehyde (10.0 g, 59.53 mmol) in dichloromethane (150 mL), NbCl$_5$ (0.810 g, 2.99 mmol) was added at rt. To the above mixture, ethyl diazoacetate (61.00 mL, 71.80 mmol; 15% solution in toluene) was added drop wise at rt and stirring continued for 16 hours. At the end of this period, solvent evaporated and the residue was chromatographed over silica gel (SiO$_2$) using 0-50% gradient of ethyl acetate in hexanes to afford ethyl 3-(2-hydroxy-4-nitro-phenyl)-3-oxo-propanoate (9.50 g, 63%) as a mixture of tautomers. $^1$H NMR (chloroform-d (CDCl$_3$)): δ1.23-1.36 (m, 6H), 3.84 (d, 1H), 4.16 (d, 1H), 4.22-4.34 (m, 4H), 6.46-6.48 (m, 1H), 7.52 (d, 1H), 7.66-7.68 (m, 1H), 7.84-7.87 (m, 1H).

Example 12—Scheme IV

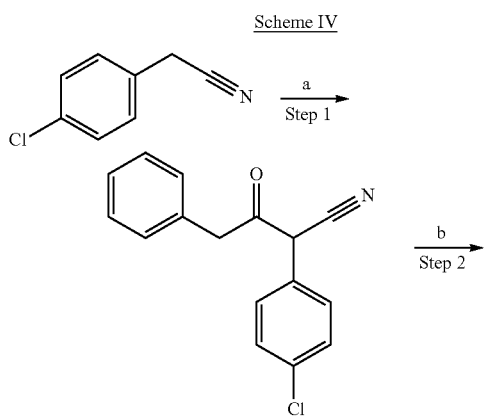

Reagents and conditions: a) NaH (60%), R$_3$CO$_2$Et, tetrahydofuran (THF), 2-8 hours, rt; b) CH$_3$CO$_2$H, N$_2$H$_4$.H$_2$O, Toluene, 120° C., 8-16 hours; c) compound 2 from Scheme I, CH$_3$CO$_2$H, 120° C., 8-16 hours; d) protecting group (PG)-amino acid, N N-dimethylaminopyridine (DMAP), N-ethyl-N'-(3-dimethylaminopropyl)carbodiimide hydrochloride (EDCI.HCl), N-methyl-2-pyrrolidone (NMP), rt, 1-5 hours; e) acid, DCM, or ethyl acetate (EtOAc), rt, and 1-6 hours.

The target compound 8 may be synthesized by standard five-step procedures: i) reacting compound 3 with aliphatic or aromatic esters using a base such as sodium hydride, sodium ethoxide, or sodium methoxide to provide compound 4; ii) forming substituted aminopyrazole by treatment with hydrazine hydrate and acetic acid in toluene; iii) forming pyrimidinone ring by reacting compound 5 with substituted beta keto esters; iv) forming ester by reacting with various acids, amino acids, or activated acids using standard coupling reagents (ethers or carbamates can be -continued

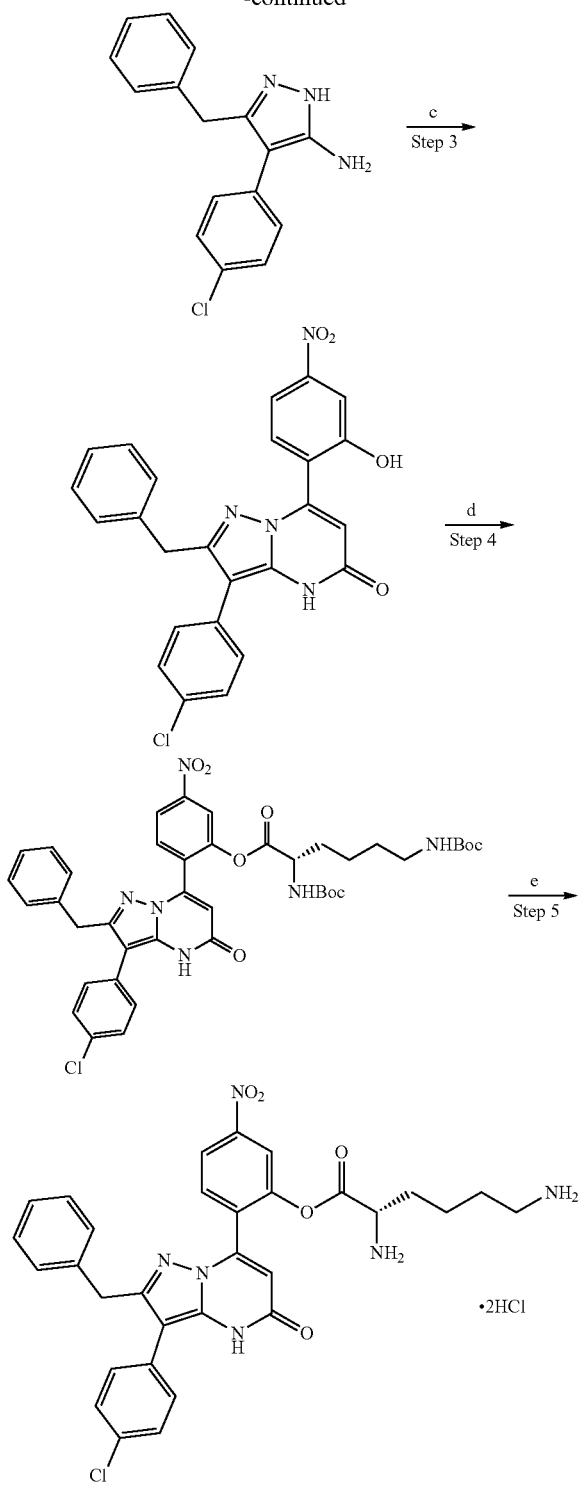

Reagents and conditions: a) NaH (60%), Ethyl phenyl acetate, THF, 16 hours, and rt; b) CH₃CO₂H, N₂H₄.H₂O, Toluene, 120° C., and 16 hours; c) Ethyl 3-(2-hydroxy-4-nitro-phenyl)-3-oxo-propanoate, CH₃CO2H, 120° C., and 16 hours; and d) N2, N6-bis-boc-L-lysine, DMAP, EDCI.HCl, NMP, rt, and five hours; e) 4M hydrochloric acid (HCl) in dioxane, EtOAc, rt, and four hours.

Detailed Procedure of Scheme IV:

Example I—Synthesis of [2-[2-benzyl-3-(4-chlorophenyl)-5-oxo-4H-pyrazolo[1,5-a]pyrimidin-7-yl]-5-nitro-phenyl] (2S)-2,6-diaminohexanoate dihydrochloride Step 1—

3-Benzyl-4-(4-chlorophenyl)-1 H-pyrazol-5-amine: to a solution of 2-(4-chlorophenyl)acetonitrile (15.0 g, 98.95 mmol) in THF was added NaH (60%) (4.73 g, 118.38 mmol) portion wise at rt. To the above mixture, initially 2 mL of ethyl 2-phenylacetate was added and the mixture was warmed to 40° C. for 10 minutes. After the initiation of the reaction, the reaction was cooled in an ice bath and the remaining ethyl 2-phenylacetate (15.35 mL), a total of 17.35 mL (108.84 mmol) was added drop wise. The ice bath was removed and stirring continued at rt for 4 hours. At the end of this period, the reaction mixture was quenched with aqueous ammonium chloride (NH₄Cl) solution (20 mL) and the pH was adjusted to 3 by adding 3N HCl. The mixture was partitioned with ethyl acetate (150 mL). The aqueous layer was extracted with ethyl acetate (50 mL). The combined ethyl acetate layer was washed with brine, dried (sodium sulfate (Na₂SO₄)), filtered, and solvent was evaporated to dryness under reduced pressure to afford 2-(4-chlorophenyl)-3-oxo-4-phenyl-butanenitrile in quantitative yield. This product was used for the next step (i.e., Step 2) without further purifications.

Step 2— the crude 2-(4-chlorophenyl)-3-oxo-4-phenyl-butanenitrile was dissolved in toluene (150 mL). To the above solution was added acetic acid (31.12 mL, 544.22 mmol) followed by hydrazine hydrate (14.40 mL, 296.85 mmol), drop wise. The reaction mixture was refluxed for 16 hours. At the end of this period it was cooled to rt, solvent and excess reagents were removed under reduced pressure. The residue was neutralized with saturated sodium bicarbonate (NaHCO₃) solution, and the solid separated was filtered and washed with water (3×50 mL) and dried under vacuum at 50° C. for 10 hours to afford title product (22.0 g, 78%). ¹H NMR (dimethylsulfoxide-d₆ (DMSO-d₆)): δ 3.87 (singlet (s), 2H), 4.57 (broad singlet (bs), 2H), 7.06-7.15 (m, 3H), 7.21-7.28 (m, 4H), 7.34 (d, 2H), and 11.60 (bs, 1H).

Step 3—

2-Benzyl-3-(4-chlorophenyl)-7-(2-hydroxy-4-nitro-phenyl)-4H-pyrazolo[1,5-a]pyrimidin-5-one: a mixture of 3-benzyl-4-(4-chlorophenyl)-1 H-pyrazol-5-amine (9.67 g, 34.10 mmol) and ethyl 3-(2-hydroxy-4-nitro-phenyl)-3-oxo-propanoate (9.5 g, 37.52 mmol) in acetic acid (80 mL) was heated at 120° C. for 16 hours. The mixture was cooled to rt and the solid separated was collected and washed with acetic acid (20 mL) followed by ethyl acetate (50 mL) and dried to afford title product (11.70 g, 73%). ¹H NMR (DMSO-d₆): δ 4.09 (s, 2H), 7.09-7.26 (m, 5H), 7.37 (d, 2H), 7.49 (d, 2H), 7.65 (d, 1H), 7.72-7.74 (m, 2H), 7.95 (s, 1H), 10.58 (s, 1H), and 12.55 (s, 1H). LCMS: [M+H] 473.10.

Step 4—

[2-[2-benzyl-3-(4-chlorophenyl)-5-oxo-4H-pyrazolo[1,5-a]pyrimidin-7-yl]-5-nitro-phenyl] (2S)-2,6-bis(tert-butoxycarbonylamino)hexanoate: to a mixture of 2-benzyl-3-(4-chlorophenyl)-7-(2-hydroxy-4-nitro-phenyl)-4H-pyrazolo[1,5-a]pyrimidin-5-one (2.46 g, 5.20 mmol) and N2, N6-bis-boc-L-lysine (2.16 g, 6.24 mmol) in THF (50 mL) was added DMAP (0.100 g) and EDCI.HCl (1.99 g, 10.40 mmol) at rt. To the above mixture, NMP (15 mL) was added drop wise at rt and stirring continued for five hours. At the end of this period, water was added extracted with EtOAc. The EtOAc layer was washed with water and brine, the EtOAc layer was dried (Na$_2$SO$_4$), filtered, and solvent evaporated to dryness. The crude was chromatographed over SiO$_2$, using 0-10% methanol in dichloromethane to give title product (3.24 g, 82%). $^1$H NMR (CDCl$_3$): δ 1.19-1.46 (m, 20H), 1.98-2.04 (m, 2H), 2.30-2.34 (m, 2H), 3.37 (t, 2H), 4.08 (s, 2H), 4.33-4.38 (m, 1H), 4.70 (bs, 1H), 5.30 (bs, 1H), 7.03-7.12 (m, 7H), 7.20-7.28 (m, 2H), 7.80 (s, 1H), 7.85-7.80 (bs 1H), 8.06 (s, 1H), 8.14 (d, 1H), 11.70 (bs, 1H).

Step 5—

[2-[2-benzyl-3-(4-chlorophenyl)-5-oxo-4H-pyrazolo[1,5-a]pyrimidin-7-yl]-5-nitro-phenyl] (2S)-2,6-diaminohexanoate dihydrochloride: to a solution [2-[2-benzyl-3-(4-chlorophenyl)-5-oxo-4H-pyrazolo[1,5-a]pyrimidin-7-yl]-5-nitro-phenyl] (2S)-2,6-bis(tert-butoxycarbonylamino)hexanoate (3.20 g, 3.99 mmol) in ethyl acetate (50 mL) was added 4M HCl in dioxane (30 mL) drop wise at room temperature and the mixture was stirred at rt for four hours. At the end of this period, solid separated was filtered and washed with diethyl ether and dried under vacuum at 50° C. for eight hours to afford title product (2.51 g, 93%). $^1$H NMR (DMSO-d$_6$): δ 1.39-1.48 (m, 4H), 1.70-1.91 (m, 3H), 2.15 (t, 1H), 3.27 (t, 1H), 4.12 (s, 2H), 4.65 (bs, 2H), 7.07-7.22 (m, 5H), 7.38 (d, 2H), 7.48 (d, 2H), 7.83 (d, 1H), 7.98 (s, 1H), 8.06 (bs, 2H), 8.23-8.30 (m, 2H), 8.83 (bs, 2H), and 13.02 (s, 1H). LCMS: [M+H] 601.19.

Example II—[2-[2-Benzyl-3-(4-chlorophenyl)-5-oxo-4H-pyrazolo[1,5-a]pyrimidin-7-yl]-5-nitro-phenyl] 2-(tert-butoxycarbonylamino)acetate

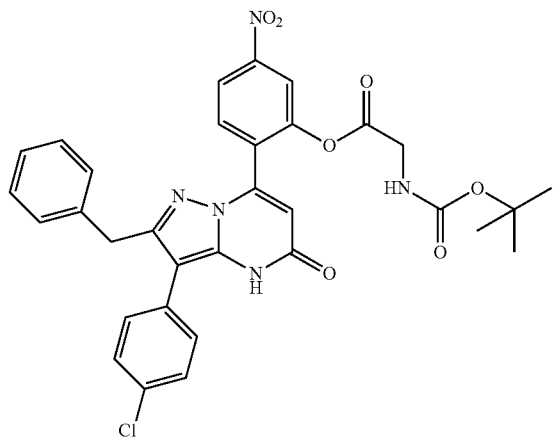 [SMILES: CC(C)(C)OC(=O)NCC(=O)Oc1cc([N+](=O)[O-])ccc1-c1cc(=O)[nH]c2c(-c3ccc(Cl)cc3)c(Cc3ccccc3)nn12]

The title compound (0.225 g, 69%) was prepared by a similar procedure described for Step 4 of Example I using 2-benzyl-3-(4-chlorophenyl)-7-(2-hydroxy-4-nitro-phenyl)-4H-pyrazolo[1,5-a]pyrimidin-5-one (0.246 g, 0.52 mmol) and N-(tert-Butoxycarbonyl)glycine (0.108 g, 0.62 mmol). $^1$H NMR (DMSO-d$_6$): δ 1.23 (s, 9H), 3.84 (d, 2H), 4.09 (s, 2H), 7.10-7.32 (m, 6H), 7.41-7.47 (m, 4H), 7.84-7.86 (m, 2H), 8.10 (s, 1H), 8.17-8.19 (m, 1H), and 12.65 (bs, 1H).

Example II—[2-[2-Benzyl-3-(4-chlorophenyl)-5-oxo-4H-pyrazolo[1,5-a]pyrimidin-7-yl]-5-nitro-phenyl] 2-aminoacetate trifluoroacetate

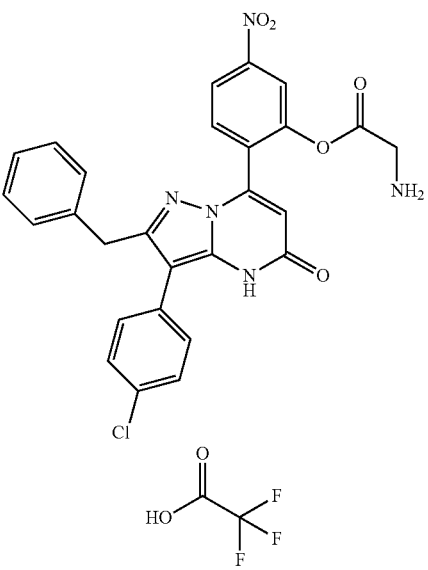

To a solution of [2-[2-benzyl-3-(4-chlorophenyl)-5-oxo-4H-pyrazolo[1,5-a]pyrimidin-7-yl]-5-nitro-phenyl] 2-(tert-butoxycarbonylamino)acetate (0.220 g, 0.350 mmol) in THF was added 4M HCl in dioxane (5 mL) at rt and stirred for four hours. At the end of this period, solvent was evaporated and the residue was triturated with diethyl ether (15 mL). The product was purified by preparative HPLC and isolated as trifluoroacetate salt (0.167 g, 73%). $^1$H NMR (DMSO-d$_6$): δ 3.95 (s, 2H), 4.08 (s, 2H), 7.07-7.28 (m, 5H), 7.37 (d, 2H), 7.49 (d, 2H), 7.85 (d, 1H), 7.97 (s, 1H), 8.21 (s, 1H), 8.24 (d, 1H), 8.55 (bs, 2H), and 12.95 (s, 1H).

Example IV—[2-[2-Benzyl-3-(4-chlorophenyl)-5-oxo-4H-pyrazolo[1,5-a]pyrimidin-7-yl]-5-nitro-phenyl] (2S)-2-(tert-butoxycarbonylamino)propanoate

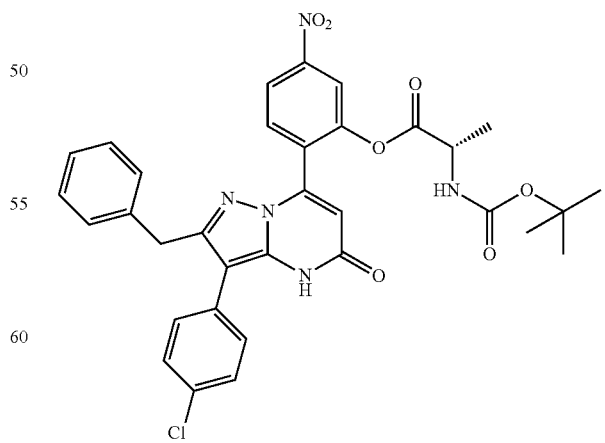

The title compound (0.270 g, 81%) was prepared by a similar procedure described for Step 4 of Example I using 2-benzyl-3-(4-chlorophenyl)-7-(2-hydroxy-4-nitro-phenyl)-4H-pyrazolo[1,5-a]pyrimidin-5-one (0.246 g, 0.52 mmol) and (0.117 g, 0.62 mmol). $^1$H NMR (DMSO-d$_6$): δ 1.22-1.25 (m, 12H), 4.08 (s, 2H), 4.11-4.15 (m, 1H), 7.08-7.22 (m, 5H), 7.37 (d, 2H), 7.47 (d, 2H), 7.83-7.85 (m, 2H), 8.06 (s, 1H), 8.20 (d, 1H), and 12.60 (s, 1H).

Example V—[2-[2-Benzyl-3-(4-chlorophenyl)-5-oxo-4H-pyrazolo[1,5-a]pyrimidin-7-yl]-5-nitro-phenyl] (2S)-2-aminopropanoate trifluoroacetate

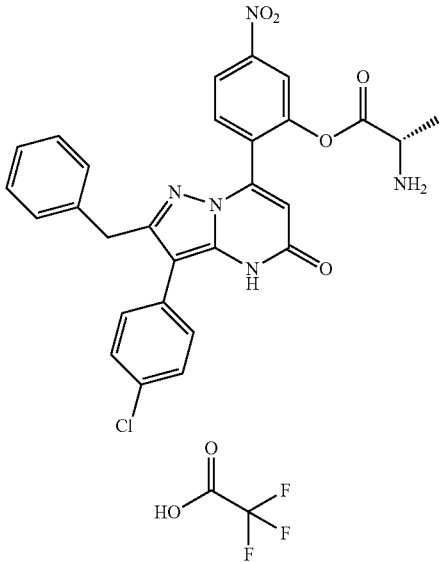

The title compound (0.170 g, 67%) was prepared by a similar procedure described for Example III using [2-[2-benzyl-3-(4-chlorophenyl)-5-oxo-4H-pyrazolo[1,5-a]pyrimidin-7-yl]-5-nitro-phenyl] (2S)-2-(tert-butoxycarbonylamino)propanoate (0.250 g, 0.388 mmol) and 4M HCl in dioxane (5 mL). The product was purified by preparative HPLC. $^1$H NMR (methanol-d$_4$ (CD$_3$OD)): δ 1.55 (d, 3H), 4.15 (s, 2H), 4.30-4.36 (m, 1H), 7.07-7.20 (m, 5H), 7.27 (d, 2H), 7.43 (d, 2H), 7.78 (d, 1H), 7.98 (s, 1H), and 8.23-8.28 (m, 2H).

Example VI—[2-[2-Benzyl-3-(4-chlorophenyl)-5-oxo-4H-pyrazolo[1,5-a]pyrimidin-7-yl]-5-nitro-phenyl] (2S)-2-(tert-butoxycarbonylamino)-3-methyl-butanoate

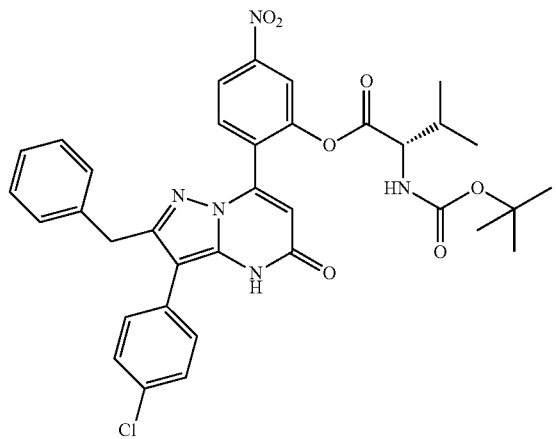 [SMILES: CC(C)[C@H](NC(=O)OC(C)(C)C)C(=O)Oc1cc([N+](=O)[O-])ccc1-c1cc(=O)[nH]c2c(-c3ccc(Cl)cc3)c(Cc3ccccc3)nn12]

The title compound (0.310 g, 89%) was prepared by a similar procedure described for Step 4 of Example I using 2-benzyl-3-(4-chlorophenyl)-7-(2-hydroxy-4-nitro-phenyl)-4H-pyrazolo[1,5-a]pyrimidin-5-one (0.246 g, 0.52 mmol) and N-(tert-butoxycarbonyl)-L-valine (0.134 g, 0.62 mmol). $^1$H NMR (DMSO-d$_6$): δ 0.69 (d, 3H), 0.74 (d, 3H), 1.26 (s, 9H), 1.97-2.05 (m, 1H), 3.96 (t, 1H), 4.08 (s, 2H), 7.08-7.35 (m, 8H), 7.47 (d, 2H), 7.82-7.89 (m, 2H), 7.98 (s, 1H), 8.19-8.21 (m, 1H), and 12.62 (s, 1H).

Example VII—[2-[2-Benzyl-3-(4-chlorophenyl)-5-oxo-4H-pyrazolo[1,5-a]pyrimidin-7-yl]-5-nitro-phenyl] (2S)-2-amino-3-methyl-butanoate trifluoroacetate

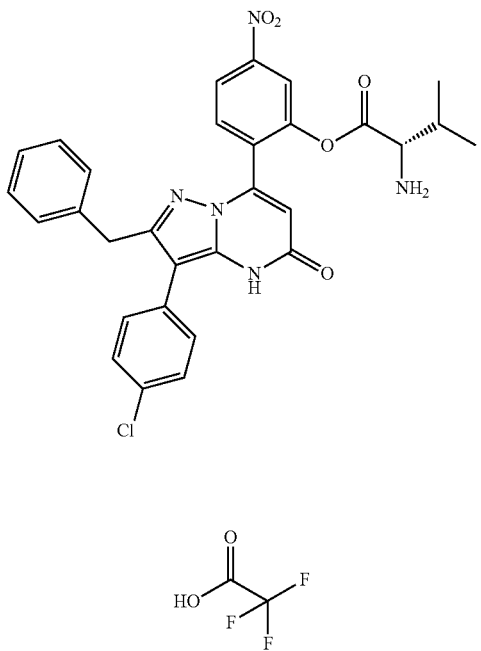

The title compound (0.25 g, 79%) was prepared by a similar procedure described for Example III using [2-[2-benzyl-3-(4-chlorophenyl)-5-oxo-4H-pyrazolo[1,5-a]pyrimidin-7-yl]-5-nitro-phenyl] (2S)-2-(tert-butoxycarbonylamino)-3-methyl-butanoate (0.310 g, 0.461 mmol)) and 4M HCl in dioxane (5 mL). The product was purified by preparative HPLC. $^1$H NMR (DMSO-d$_6$): δ 0.73 (d, 3H), 0.77 (d, 3H), 2.11-2.16 (m, 1H), 4.07 (s, 2H), 4.09 (bs, 1H), 7.06-7.32 (m, 5H), 7.31 (d, 2H), 7.49 (d, 2H), 7.84 (d, 1H), 7.95 (s, 1H), 8.25 (d, 1H), 8.27 (s, 1H), 8.66 (bs, 2H), and 12.90 (s, 1H).

Example 13—Synthesis of NAV-AAC', NAV-AAQ', and NAV-AAR'

Figure 14:
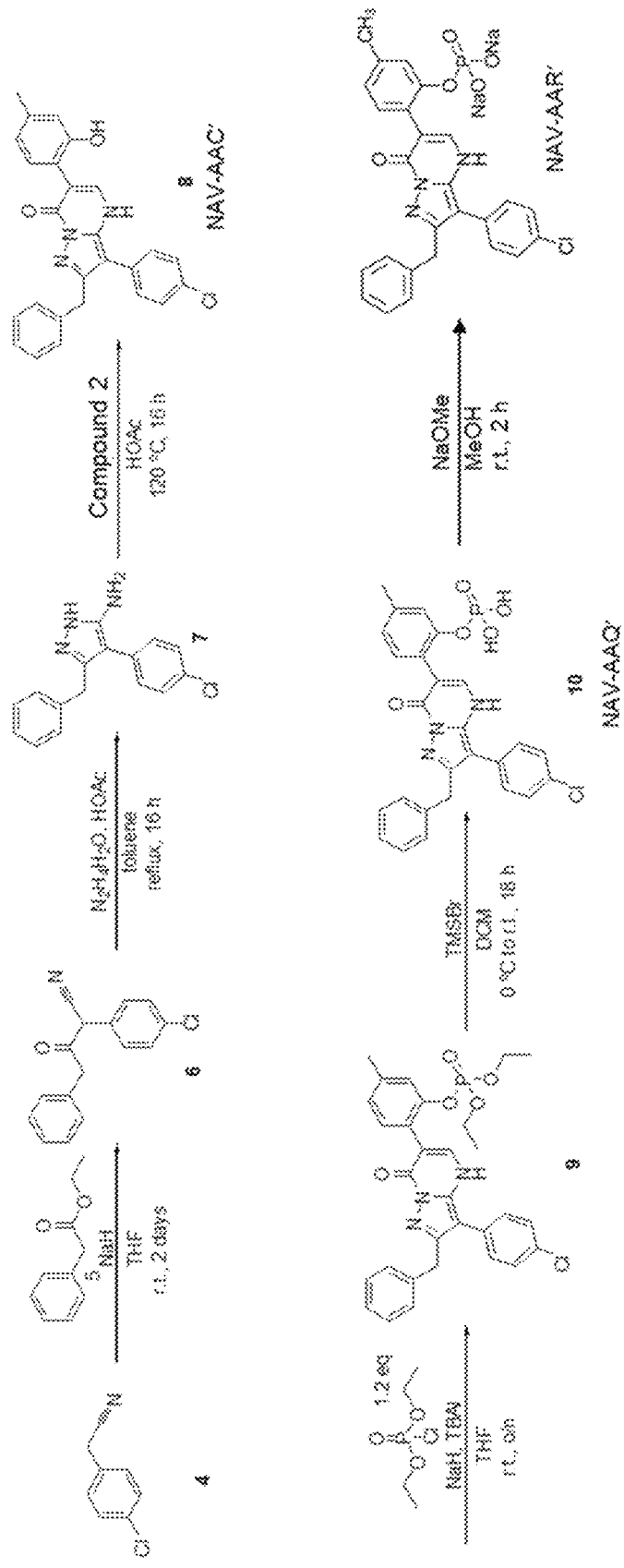
FIG. 14 shows the scheme for synthesis of NAV-AAC' and NAV-AAR'.
Figure 14:
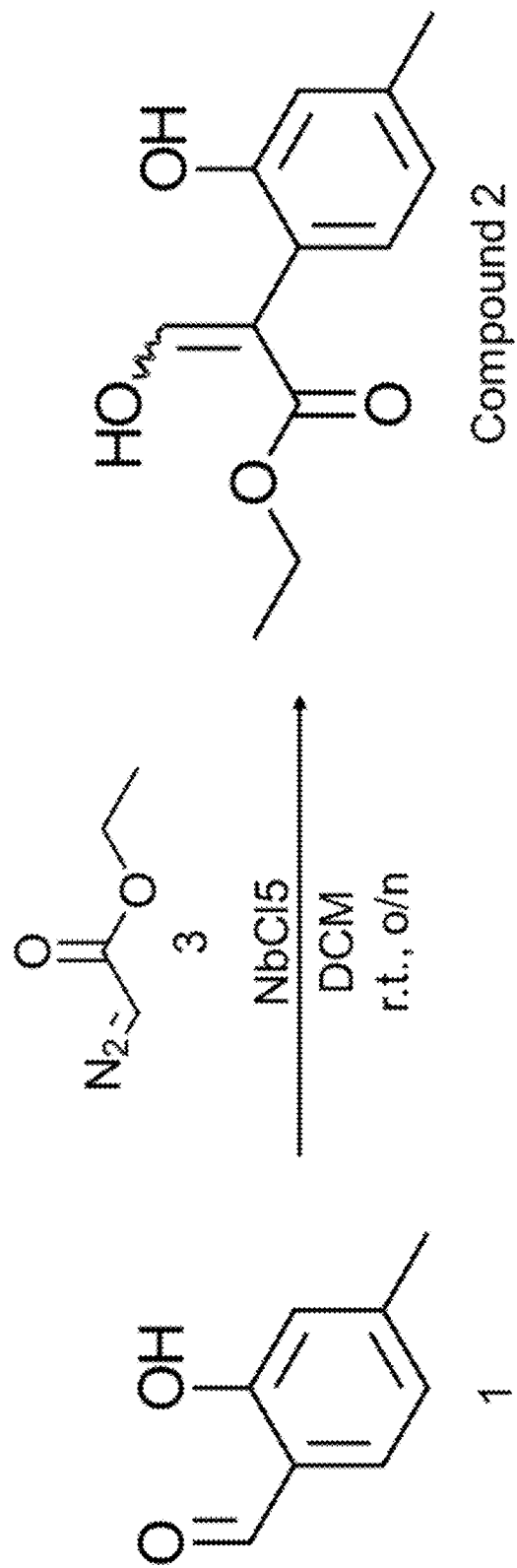
Figure 14:
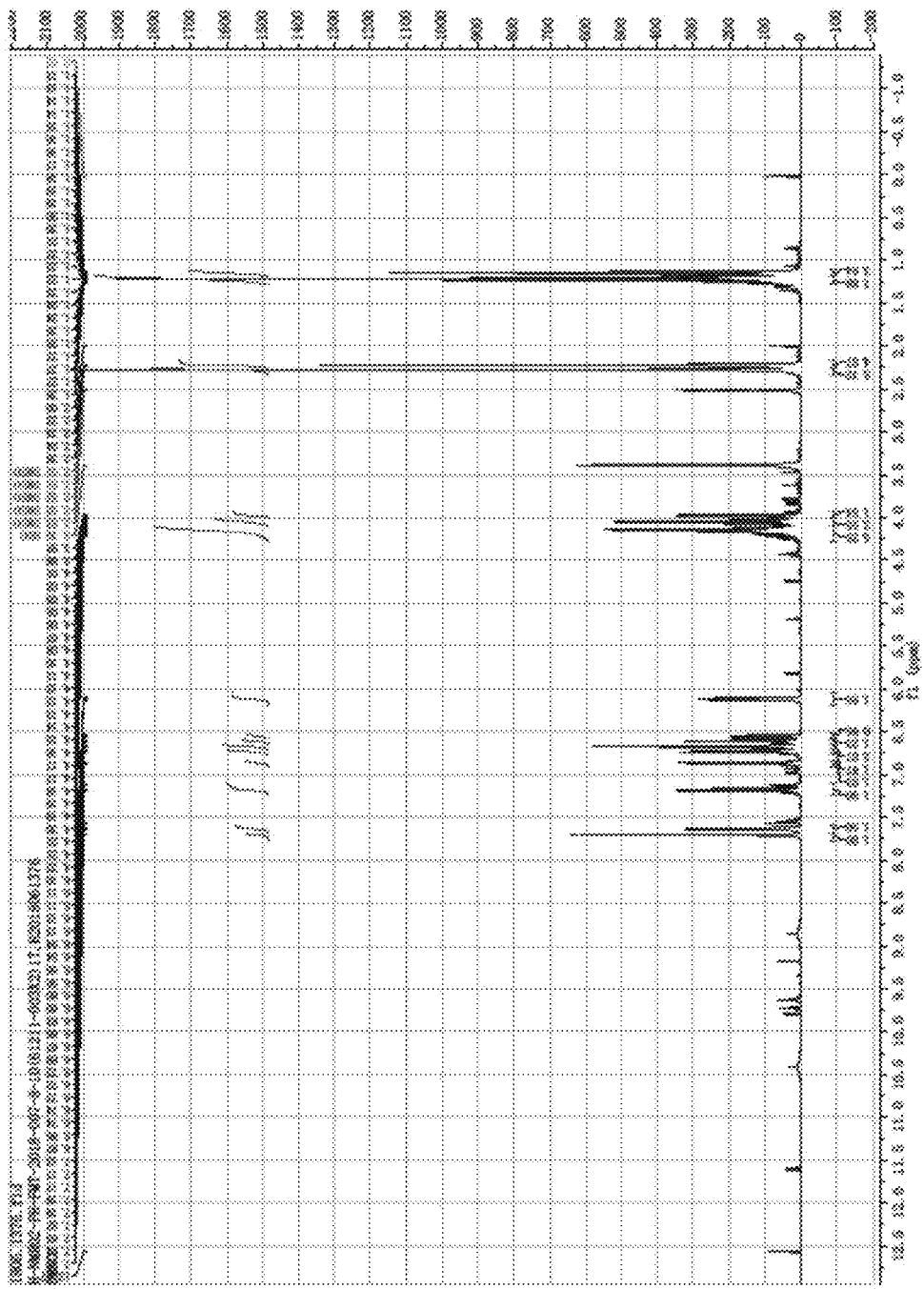
Figure 14:
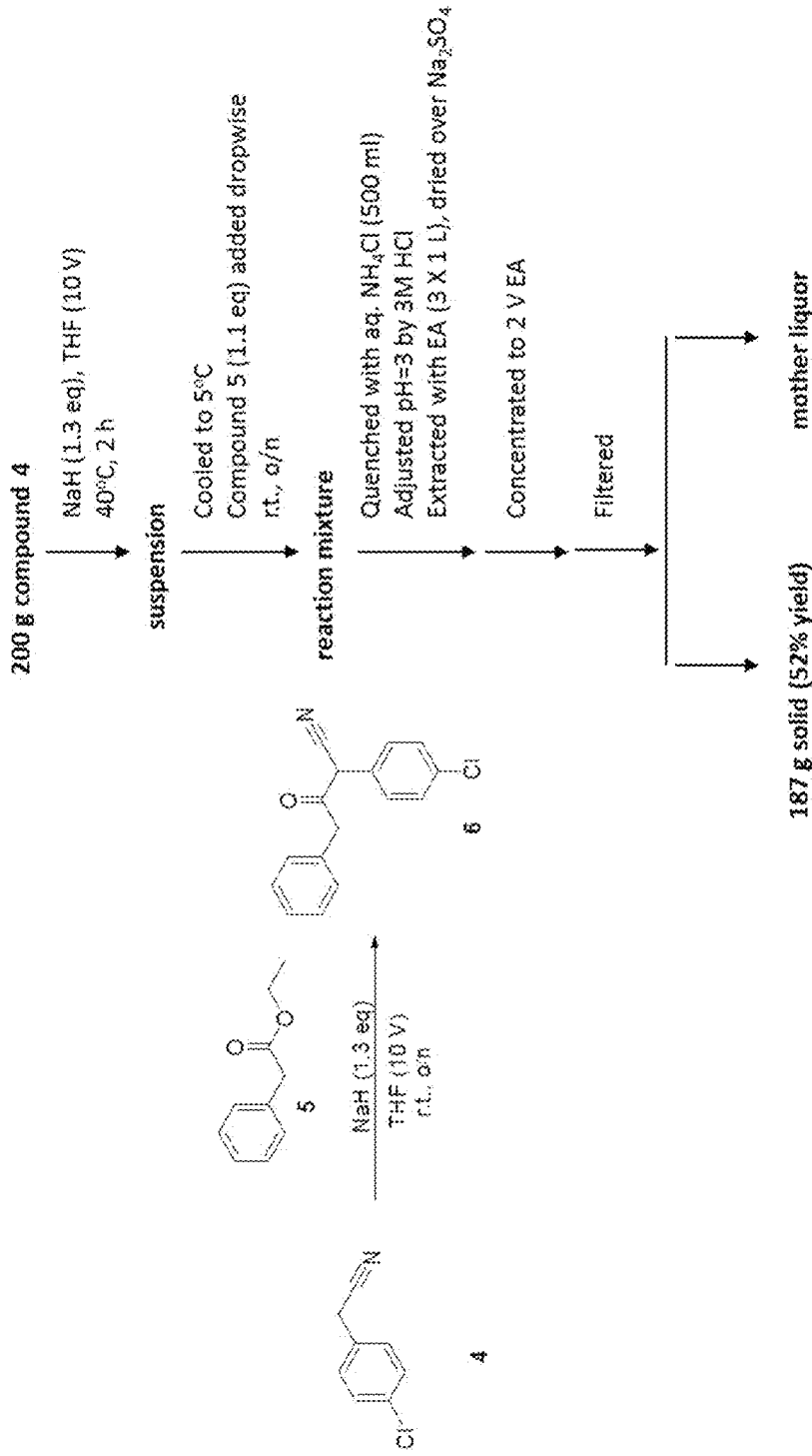
Figure 14:
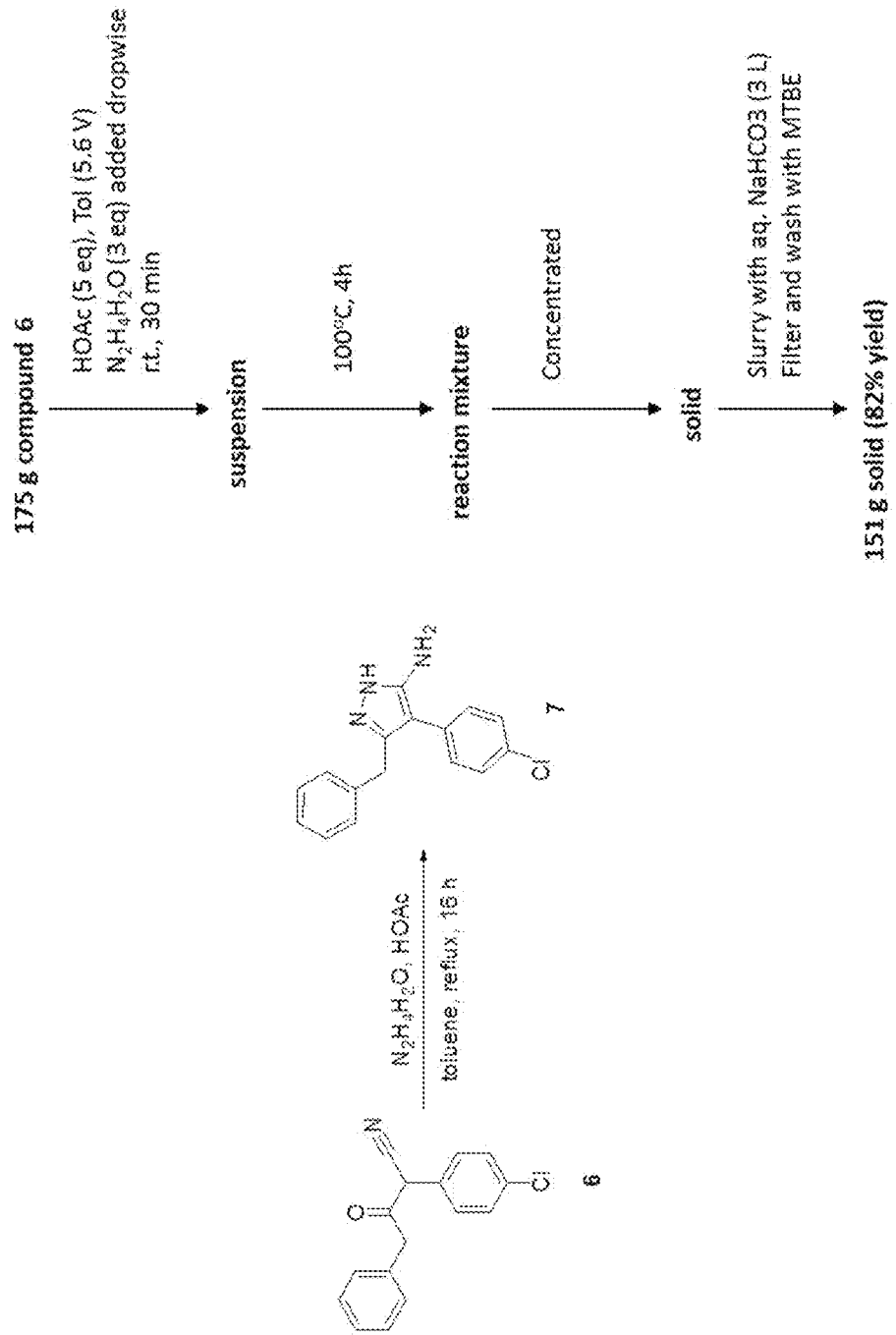
Figure 14:
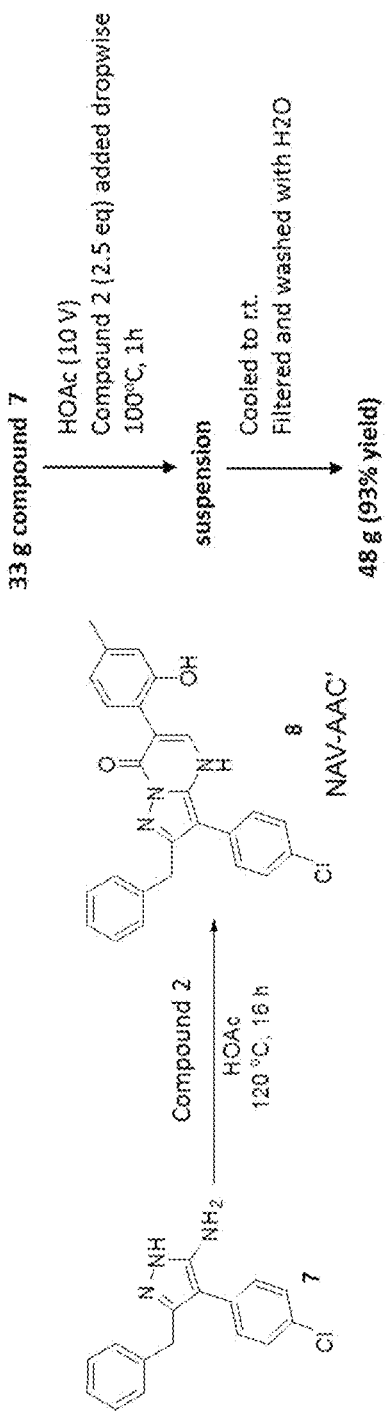
Figure 14:
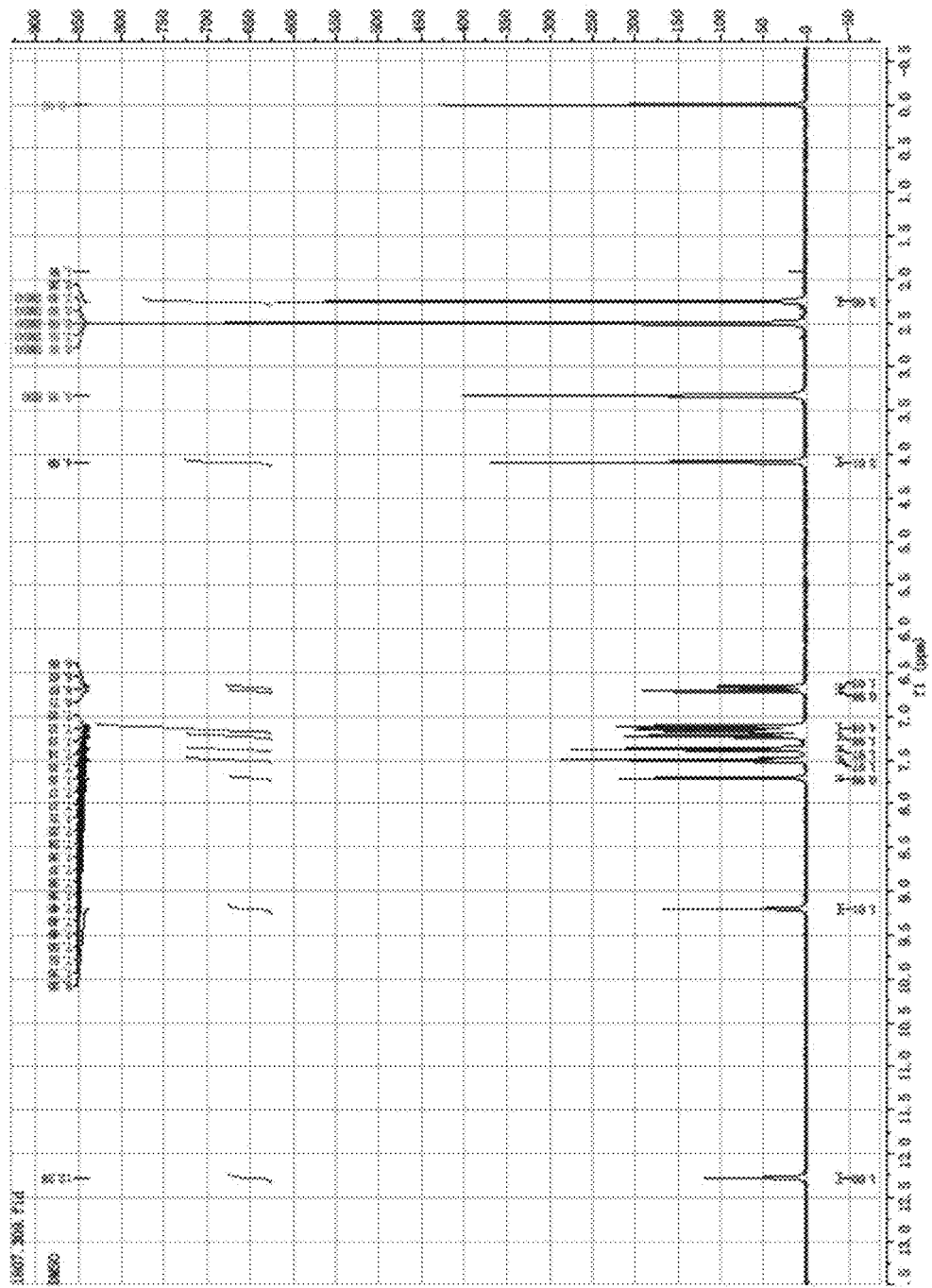
Figure 14:
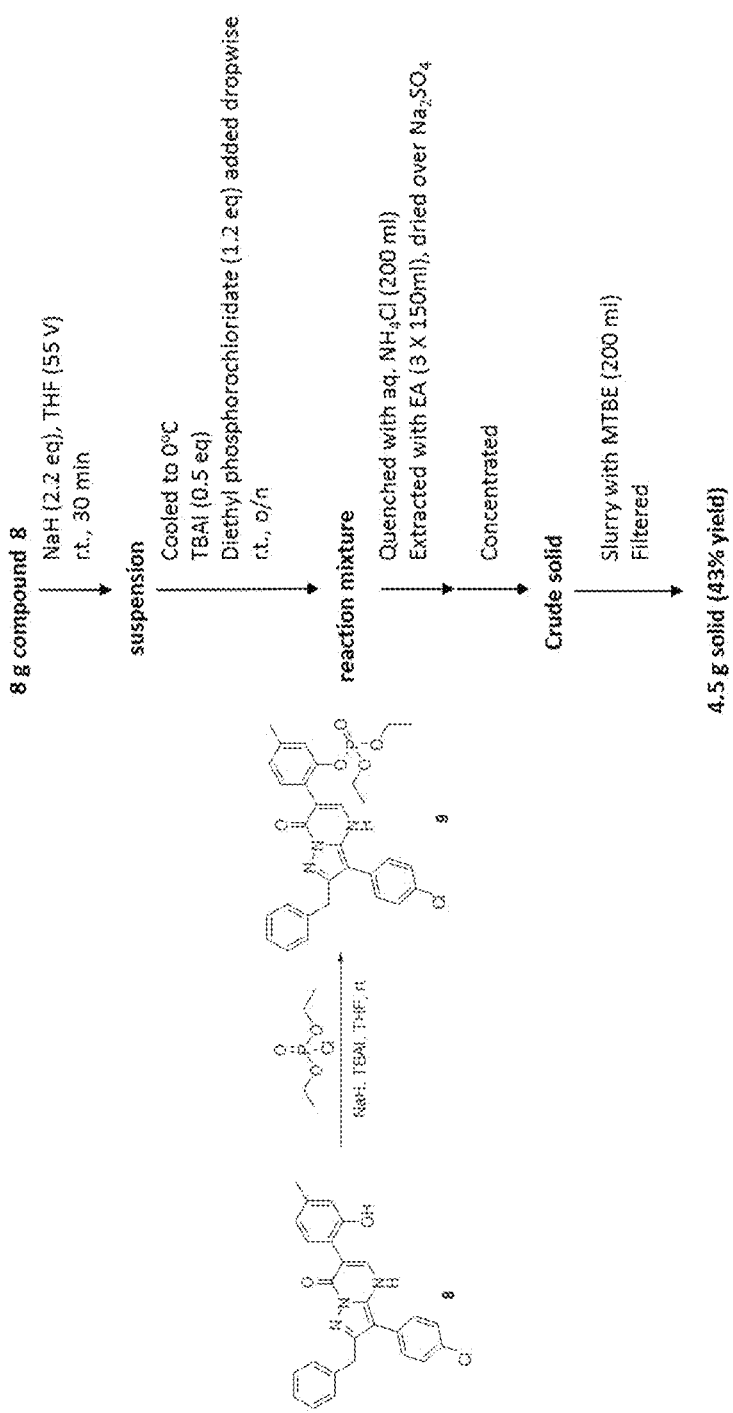
Figure 14:
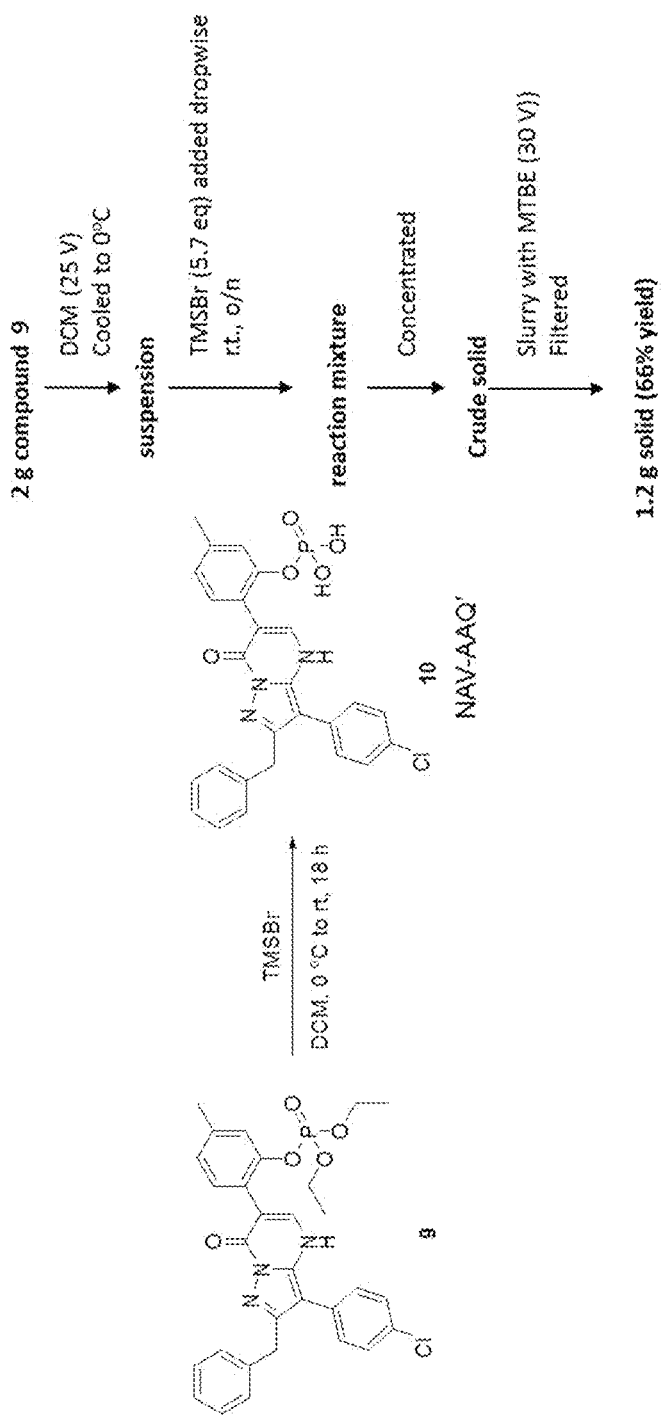
Figure 14:
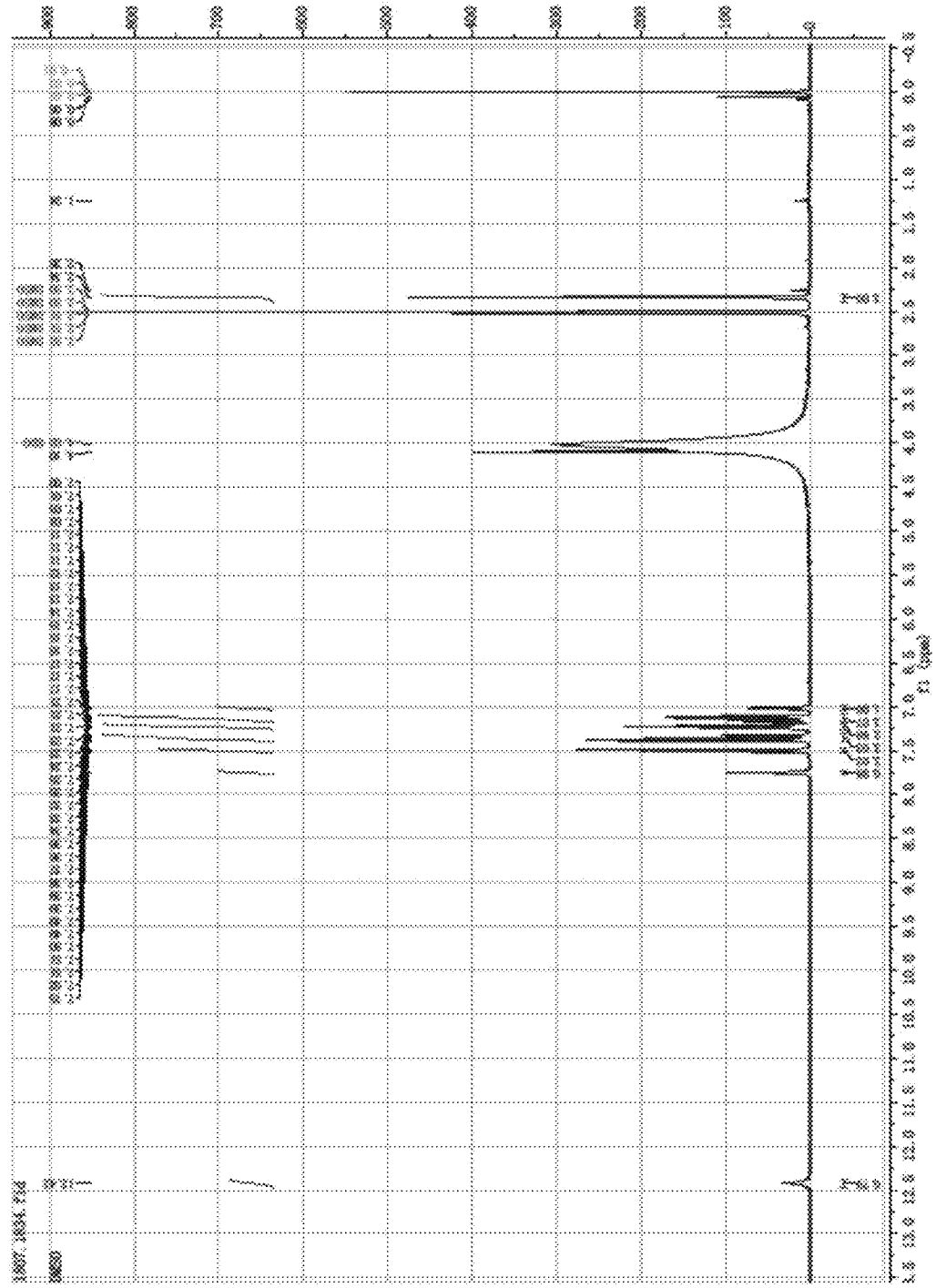
Figure 14:
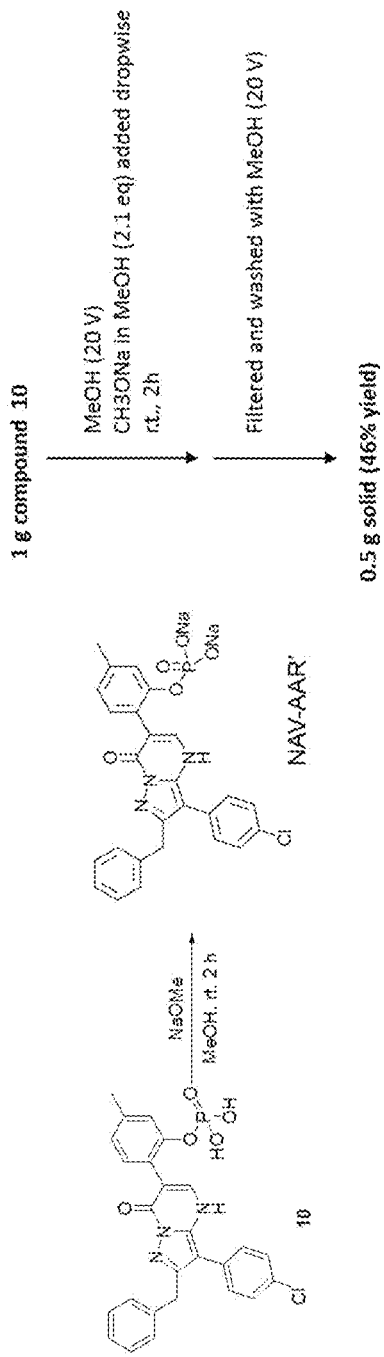
Figure 14:
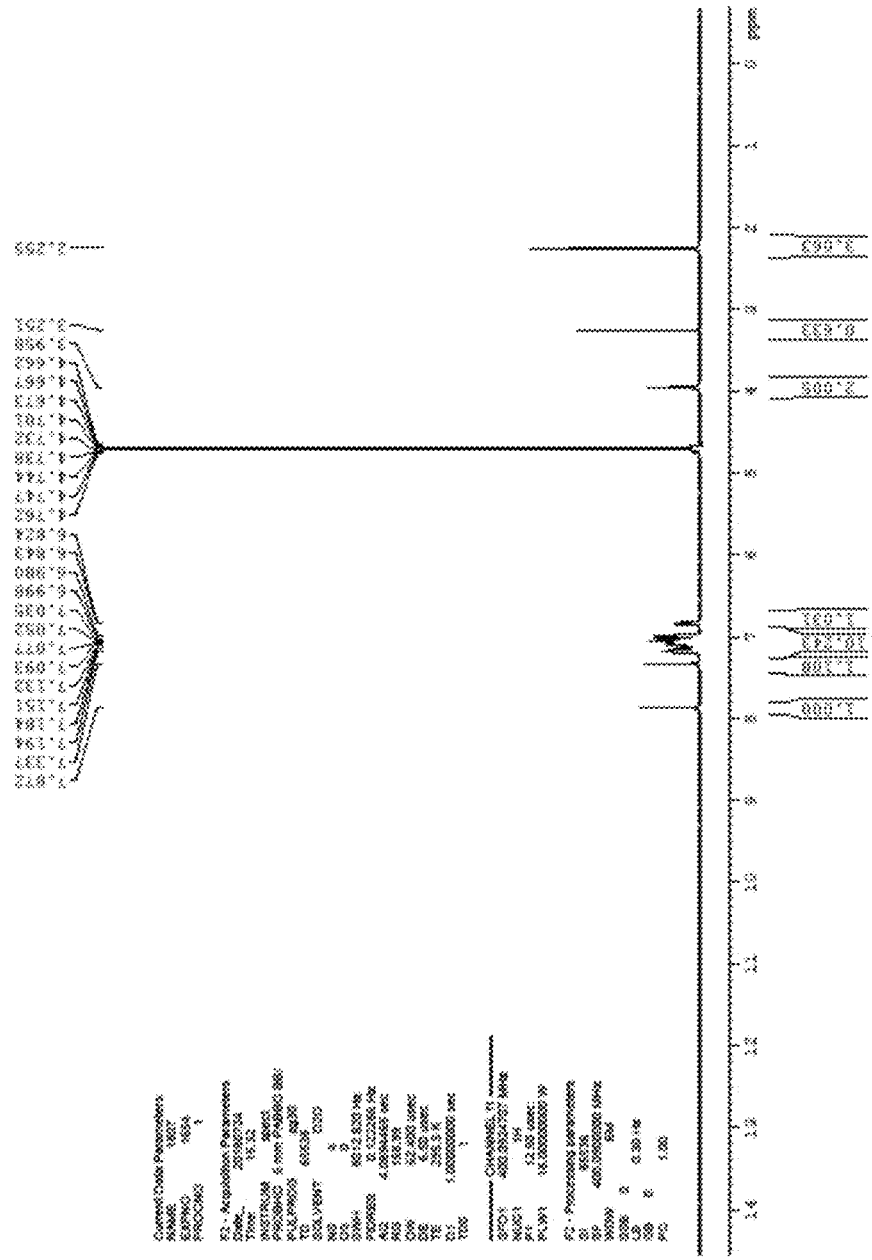

The synthetic route to NAV-AAC', NAV-AAQ', and NAV-AAR', including proton NMR spectra, is shown in FIG. 14.

Example 14—In Vitro Potency and Solubility of ARF6 Prodrugs

TABLE 4

| Compound | ARF6 inhibition IC$_{50}$ (μM) | Solubility (μM) | | | | |
|---|---|---|---|---|---|---|
| | | D5W Prepared from powder | 20 mM Na Citrate, pH 3.1 | 0.1% Tween 80 in D5W Diluted from 10 mM solution in DMSO | H$_2$O | DPBS, pH 7.4 |
| NAV-B (Example I) | 2.6 | 14,000 | 280 | 42 | 400 | 1 |
| Example V | 1.9 | 20 | 160 | 5.4 | 150 | <1 |
| Example III | | | 325 | | 375 | |

Example 15—Synthesis of Di-sodium Salt of [2-[3-(3,4-dichlorophenyl)-5-oxo-2 (trifluoromethyl)-4H-pyrazolo[1,5-a]pyrimidin-7-yl]phenyl]dihydrogen phosphate

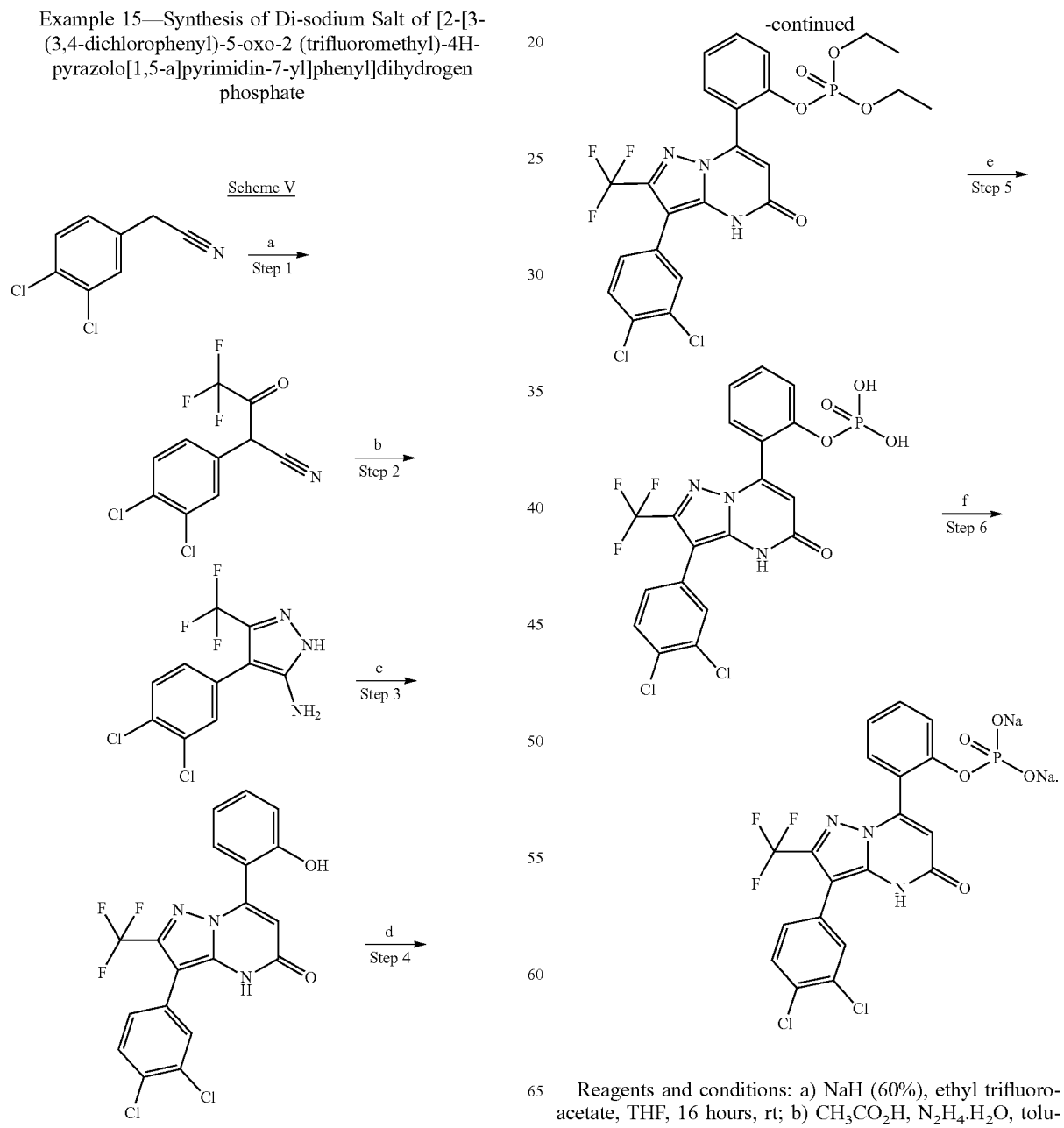

Reagents and conditions: a) NaH (60%), ethyl trifluoroacetate, THF, 16 hours, rt; b) CH$_3$CO$_2$H, N$_2$H$_4$.H$_2$O, toluene, 120° C., 16 hours; c) ethyl 3-(2-hydroxyphenyl)-3-oxopropanoate, $CH_3CO_2H$, 120° C., 6 hours; d) NaH (60%), diethyl chlorophosphate, $Bu_4NI$, THF, 2 hours; e) bromotirmethylsilane, DCM, 0-25° C., 16 hours; f), NaOMe (25%), MeOH, rt, 3 hours.

Step 1—

Synthesis of 2-(3,4-dichlorophenyl)-4,4,4-trifluoro-3-oxo-butanenitrile. To a solution of 2-(3,4-dichlorophenyl) acetonitrile (15.0 g, 80.62 mmol) in THF was added NaH (60%) (3.87 g, 96.75 mmol) portion wise at rt. To the above mixture, initially 2 mL of ethyl trifluoroacetate was added and the mixture was warmed to 40° C. for 10 minutes. After the initiation of the reaction, the reaction was cooled in an ice bath and the remaining ethyl trifluoroacetate (9.51 mL), a total of 11.51 mL (96.75 mmol) was added drop wise. The ice bath was removed and stirring continued at rt for 4 hours. At the end of this period, the reaction mixture was quenched with aqueous ammonium chloride ($NH_4Cl$) solution (20 mL) and the pH was adjusted to 3 by adding 3N HCl. The mixture was partitioned with ethyl acetate (150 mL). The aqueous layer was extracted with ethyl acetate (50 mL). The combined ethyl acetate layer was washed with brine, dried (sodium sulfate ($Na_2SO_4$)), filtered, and solvent was evaporated to dryness under reduced pressure to afford 2-(3,4-dichlorophenyl)-4,4,4-trifluoro-3-oxo-butanenitrile in quantitative yield. This product was used for the next step without further purifications.

Step 2—

Synthesis of 4-(3,4-dichlorophenyl)-3-(trifluoromethyl)-1H-pyrazol-5-amine. The crude 2-(3,4-dichlorophenyl)-4,4,4-trifluoro-3-oxo-butanenitrile (from Step 1) was dissolved in toluene (150 mL). To the above solution was added acetic acid (23.00 mL, 403.10 mmol) followed by hydrazine hydrate (11.73 mL, 241.88 mmol), drop wise. The reaction mixture was refluxed for 16 hours. At the end of this period it was cooled to rt, solvent and excess reagents were removed under reduced pressure. The residue was neutralized with saturated sodium bicarbonate ($NaHCO_3$) solution, and the mixture was extracted with ethyl acetate and washed with water (3×50 mL). The ethyl acetate layer was dried ($Na_2SO_4$), filtered, and solvent evaporated to dryness. The crude was chromatographed over $SiO_2$ using gradient of ethyl acetate in dichloromethane to afford title product (10.40 g, 44%). $^1H$ NMR (DMSO-$d_6$): δ 5.47 (bs, 2H), 7.23 (d, 1H), 7.45 (d, 1H), 7.63 (d, 1H), 12.41 (s, 1H).

Step 3—

Synthesis of 3-(3,4-dichlorophenyl)-7-(2-hydroxyphenyl)-2-(trifluoromethyl)-4H-pyrazolo[1,5-a]pyrimidin-5-one: a mixture of 4-(3,4-dichlorophenyl)-3-(trifluoromethyl)-1 H-pyrazol-5-amine (4.00 g, 13.51 mmol) and ethyl 3-(2-hydroxyphenyl)-3-oxo-propanoate (3.37 g, 16.21 mmol) in acetic acid (30 mL) was heated at 120° C. for 6 hours. The mixture was cooled to rt and the solid separated was collected and washed with acetic acid (50 mL) followed by ethyl acetate (50 mL) and dried to afford title product (4.60 g, 77%). $^1H$ NMR (DMSO-$d_6$): δ 6.82-6.90 (m, 2H), 6.91-7.20 (m, 1H), 7.26-7.28 (m, 1H), 7.41-7.44 (m, 1H), 7.75-7.79 (m, 2H), 7.96 (s, 1H), 9.42 (bs, 1H), 12.83 (bs, 1H). LC-MS 462 [M+Na]+.

Step 4—

Synthesis of [2-[3-(3,4-dichlorophenyl)-5-oxo-2-(trifluoromethyl)-4H-pyrazolo[1,5-a]pyrimidin-7-yl]phenyl] diethyl phosphate: to a solution of 3-(3,4-dichlorophenyl)-7-(2-hydroxyphenyl)-2-(trifluoromethyl)-4H-pyrazolo[1,5-a]pyrimidin-5-one (0.300 g, 0.681 mmol) in THF (15 mL) was added NaH (60%) (0.060 g, 1.49 mmol) portion wise at room temperature and stirred for 20 min at rt. The mixture was cooled to 0° C. and diethyl chlorophosphate (0.118 mL, 0.817 mmol) in (1.0 mL) THF was added drop wise. To the above mixture, $Bu_4NI$ (0.125 g, 0.340 mmol) was added and stirring continued for an additional 30 minutes at 0° C. and at room temperature for 2 hours. At the end of this period reaction mixture was quenched with saturated $NH_4Cl$ solution and ethyl acetate (30 mL) was added and washed with water (2×20 mL) and brine (20 mL). The ethyl acetate layer was dried ($Na_2SO_4$), filtered and solvent evaporated to dryness. The crude was chromatographed over $SiO_2$ using 0-20% methanol in DCM to afford title product (0.360 g, 92%). $^1H$ NMR (DMSO-$d_6$): δ 1.10 (t, 6H), 3.94-4.02 (m, 4H), 7.26-7.36 (m, 2H), 7.40-7.47 (m, 3H), 7.75-7.78 (m, 2H), 8.03 (s, 1H), 13.02 (bs, 1H). $^{31}P$ NMR (DMSO-$d_6$): δ −6.91. LC-MS: m/z 576 [M+H]+.

Step 5—

Synthesis of [2-[3-(3,4-dichlorophenyl)-5-oxo-2-(trifluoromethyl)-4H-pyrazolo[1,5-a]pyrimidin-7-yl]phenyl] dihydrogen phosphate: a solution of [2-[3-(3,4-dichlorophenyl)-5-oxo-2-(trifluoromethyl)-4H-pyrazolo[1,5-a]pyrimidin-7-yl]phenyl] diethyl phosphate (1.5 g, 2.60 mmol) was in DCM (30 mL) and was cooled to 0° C. To the above solution, bromotirmethylsilane (5.15 mL, 39.04 mmol) was added drop wise and stirring continued at rt for 18 hours. At the end of this period, solvent and the excess bromotirmethylsilane was evaporated under reduced pressure. To the residue, toluene (20 mL) was added and evaporated to dryness. The crude mixture was dissolved in DCM (10 mL) and cooled to 0° C. and methanol (5 mL) and stirred for 30 minutes and evaporated to dryness. To the residue, water (50 mL) was added and stirred for 30 minutes and the solid separated was collected and washed with water and dried to afford title product (1.21 g, 90%). Analytical sample was prepared as follows, dissolving crude product (0.15 g) in methanol (10 mL) and triethyl ammonium carbonate (5 mL) then the volatiles were removed under reduced pressure and the residue was acidified with 3N HCl, the solid separated was filtered and washed with water and dried to afford 60 mg of pure product. $^1H$ NMR (DMSO-$d_6$): δ 7.17-7.21 (m, 1H), 7.33-7.45 (m, 4H), 7.72-7.77 (m, 2H), 8.01 (s, 1H). $^{31}P$ NMR (DMSO-$d_6$): δ −6.18.

Step 6—

Synthesis of di-sodium salt of [2-[3-(3,4-dichlorophenyl)-5-oxo-2(trifluoromethyl)-4H-pyrazolo[1,5-a]pyrimidin-7-yl]phenyl] dihydrogen phosphate. To a solution of [2-[3-(3,4-dichlorophenyl)-5-oxo-2-(trifluoromethyl)-4H-pyrazolo[1,5-a]pyrimidin-7-yl]phenyl] dihydrogen phosphate (0.47 g, 0.905 mmol) in methanol (20 mL) was added NaOMe (25% solution in methanol) (0.435 mL, 1.897 mmol) and stirred at rt for 2 hours. Solvent was evaporated under reduced pressure and the residue was triturated with mixture of hexane and ethyl acetate (9:1). The solid separated was filtered and washed with hexanes and the product was dried at 55° C. under vacuum to afford title product (0.480 g, 94%). $^1H$ NMR ($D_2O$): δ 6.95-6.99 (m, 1H), 7.18-7.22 (m, 1H), 7.27-7.30 (m, 2H), 7.41-7.44 (m, 2H), 7.56 (s, 1H), 8.03 (s, 1H). $^{31}P$ NMR ($D_2O$): δ −0.33.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

It will be apparent to those having skill in the art that many changes may be made to the details of the above-described embodiments without departing from the underlying principles of the invention. The scope of the present invention should, therefore, be determined only by the following claims.

The invention claimed is:

1. A composition, comprising:
a compound of Formula I or Formula II,

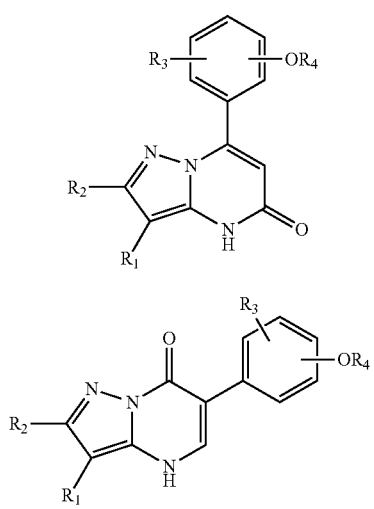

Formula I

Formula II wherein R1 is selected from at least one of an aryl group or a cycloalkyl group;
R2 is selected from at least one of a morpholino group coupled through a spacer, an aryl group, an aryl group coupled through a spacer, a heteroaryl group, an unsaturated cycloalkyl group, a saturated cycloalkyl group, an unsaturated heterocyclic group, a saturated heterocyclic group, a halogenated alkyl group, or a cyclopropyl group;
R3 is selected from at least one of an alkyl group, a cycloalkyl group, an alkoxy group, a hydroxy group, a halo group, a nitro group, a cyano group, an alkyne group, an alkyne coupled through a spacer, an alkyne amino group, a phosphate group, an aryl group, a heteroaryl group, or a keto group;
R4 is selected from at least one of an L-glycine, an L-alanine, an L-lysine ester, or a phosphate group; and
pharmaceutically acceptable salts thereof.

2. The composition of claim 1, wherein R1 is an aryl group and wherein the aryl group is substituted with one or more halo groups.

3. The composition of claim 2, wherein the aryl group is substituted with one or more chloro groups.

4. The composition of claim 1, wherein R2 is a halogenated alkyl group, and wherein the halogenated alkyl group is —CF3.

5. The composition of claim 1, wherein R2 is a morpholino group coupled through a spacer or an aryl group coupled through a spacer, in which the spacer is a C1-C4 alkyl group.

6. The composition of claim 1, wherein R3 is at least one of an alkyl group, a cycloalkyl group, an alkoxy group, a hydroxy group, a halo group, a nitro group, a cyano group, an alkyne group, an alkyne amino group, a phosphate group, an aryl group, a heteroaryl group, or a keto group.

7. The composition of claim 6, wherein the R3 is at least one of a hydrogen, a hydroxy group, a halo group, a nitro group, a cyano group, an alkyne, an alkyne amino group, or a phosphate group.

8. The composition of claim 7, wherein the halo group is at least one of a fluoro group, a chloro group, or a bromo group.

9. The composition of any one of claim 1, wherein R3 is an alkyne, and wherein the alkyne is coupled to the compound of Formula I or Formula II via a spacer.

10. The composition of claim 9, wherein the spacer is a C1-C4 alkyl group.

11. A composition, comprising at least one of the compounds selected from:

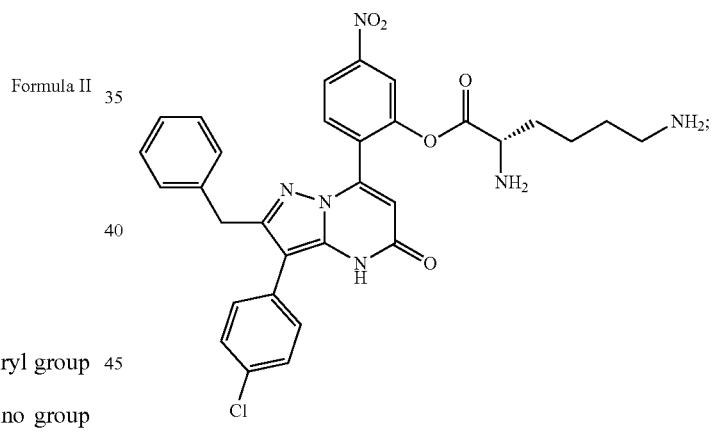

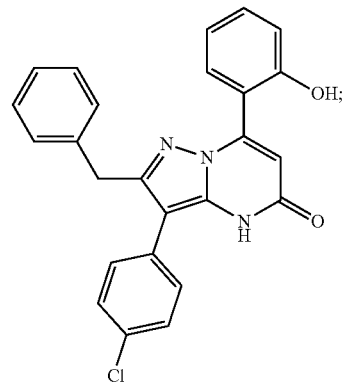

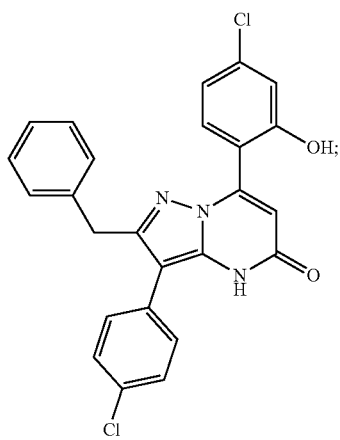
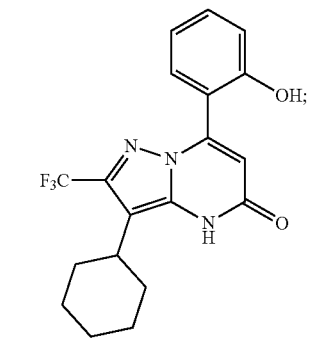
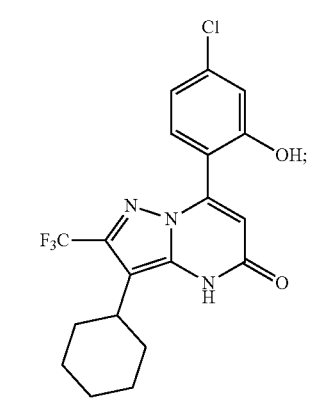
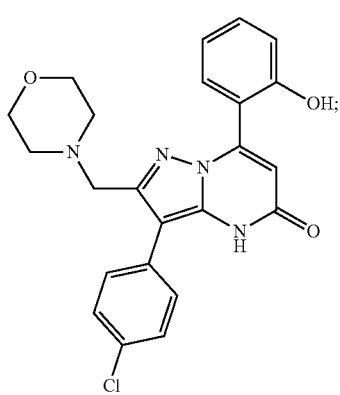
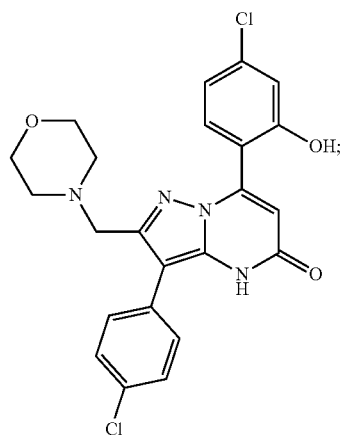
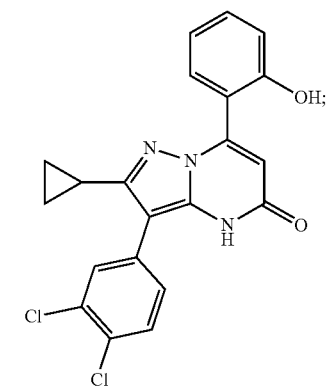
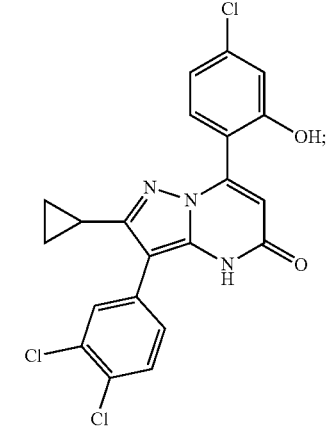
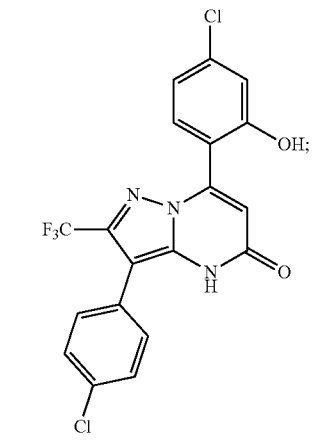

115
-continued
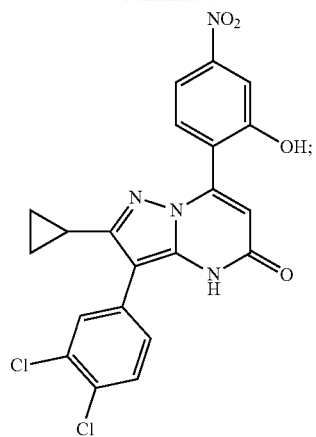
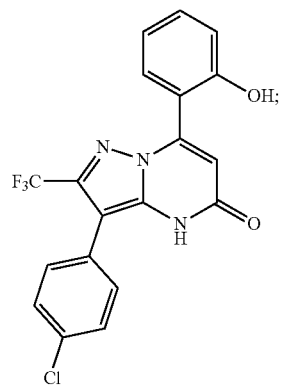
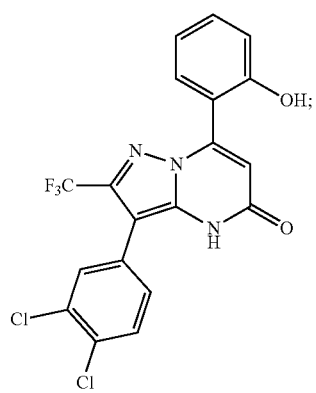
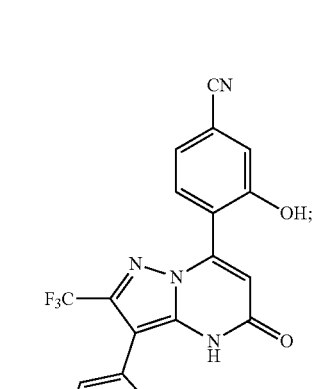
116
-continued
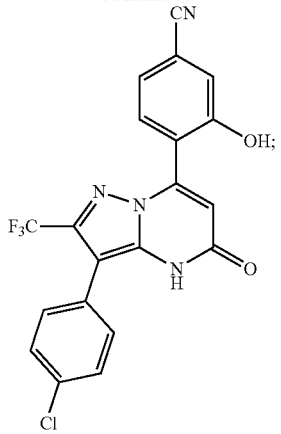
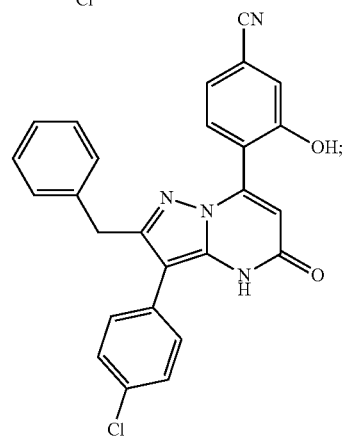
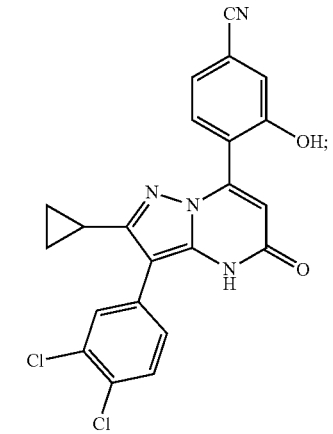
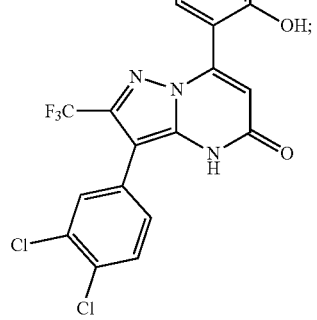

117
-continued
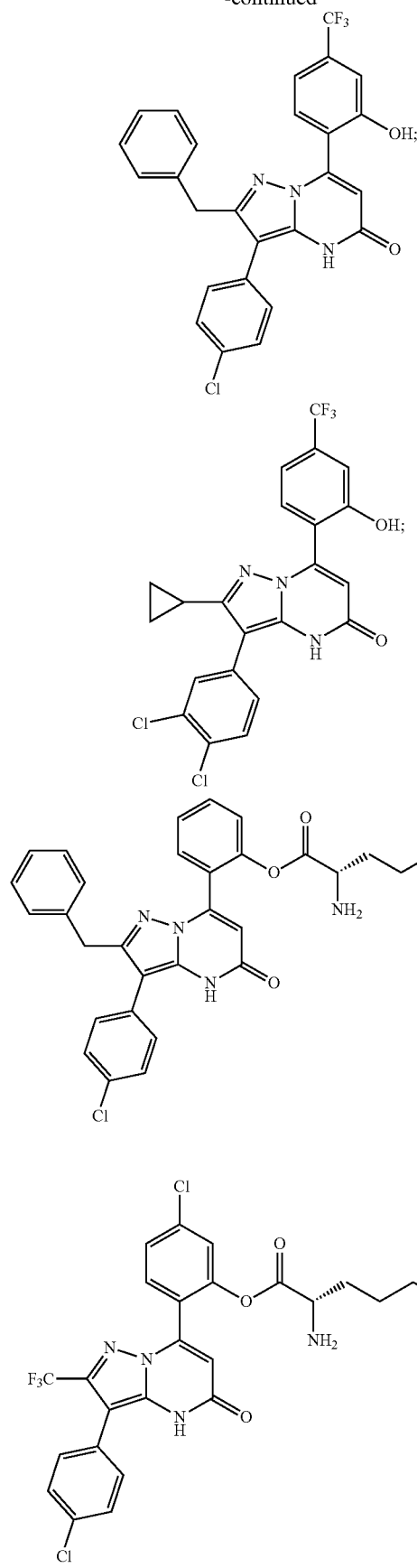
118
-continued
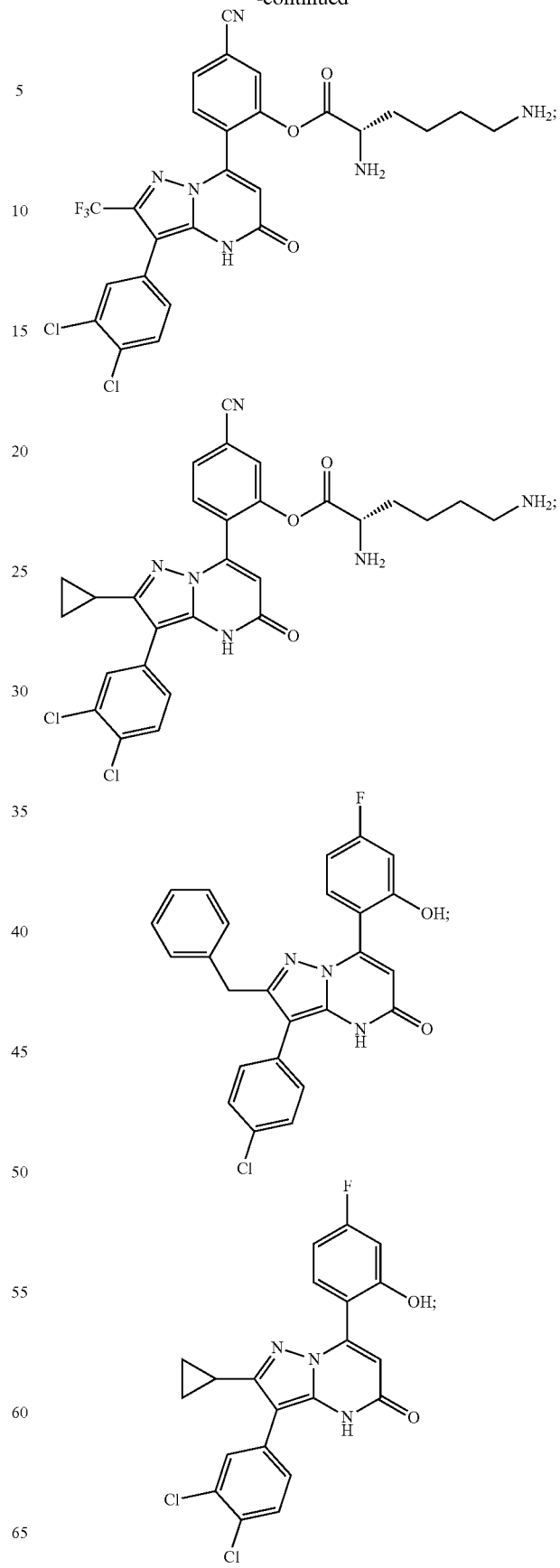

119
-continued
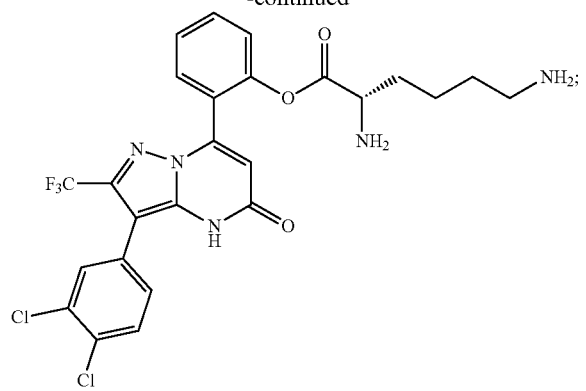
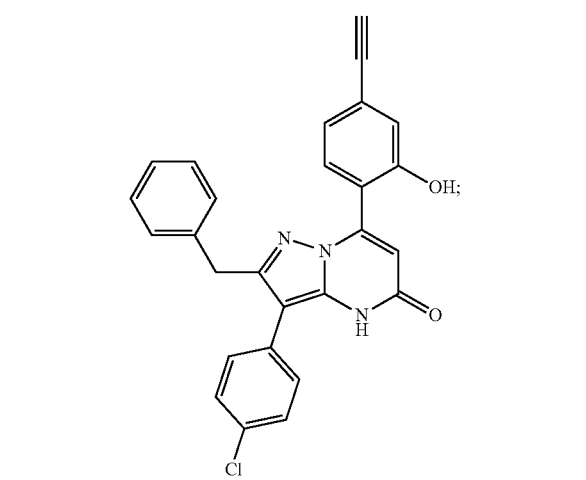
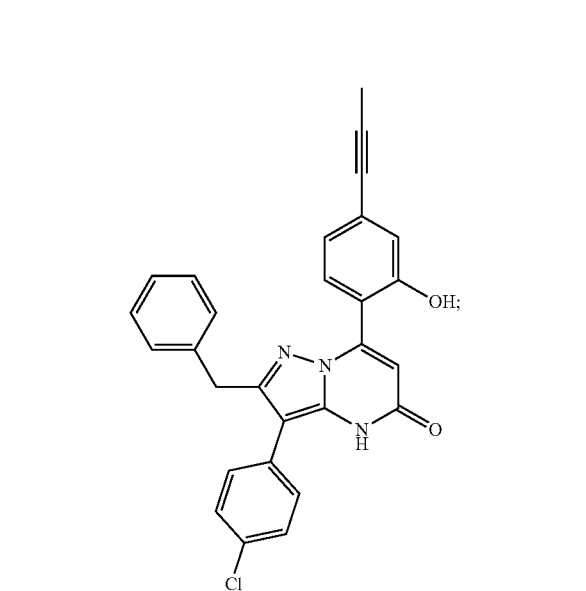
120
-continued
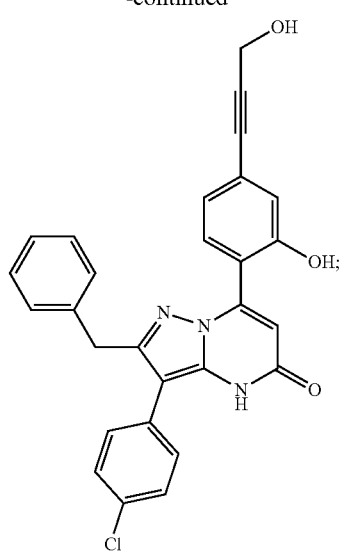
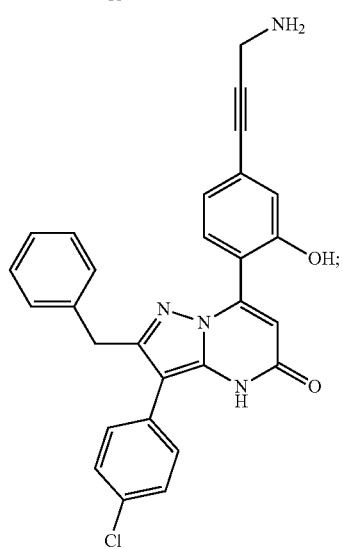
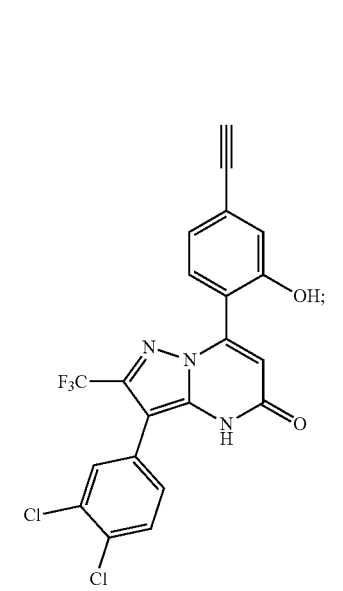

-continued
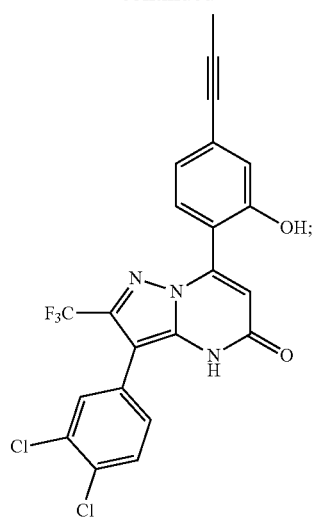
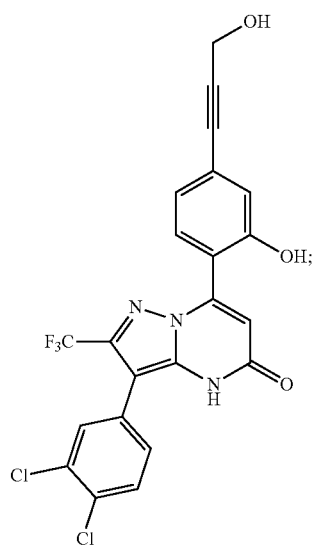
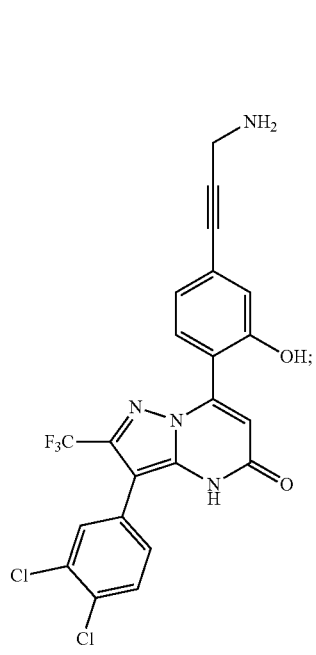
-continued
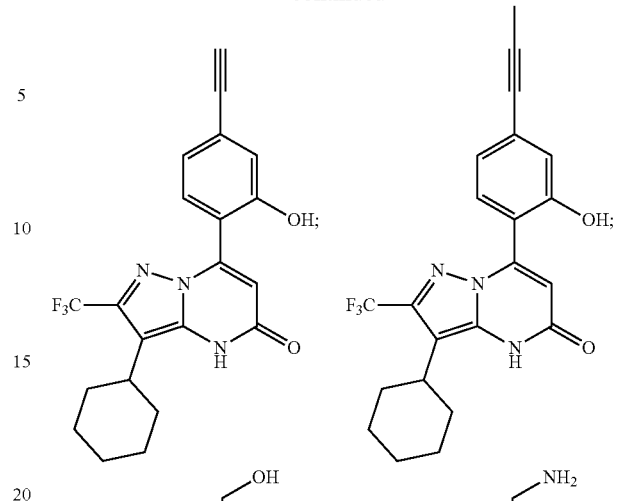
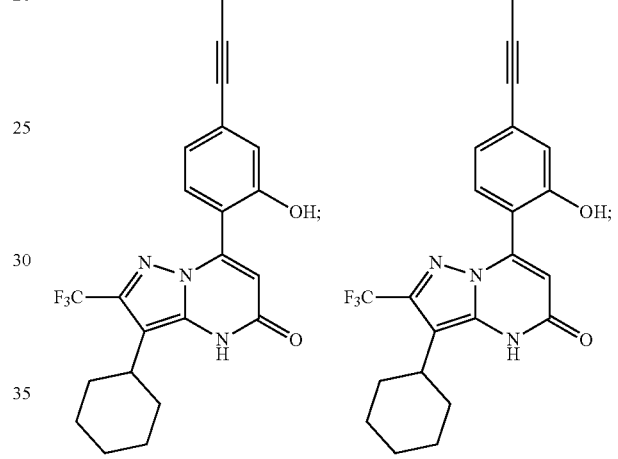
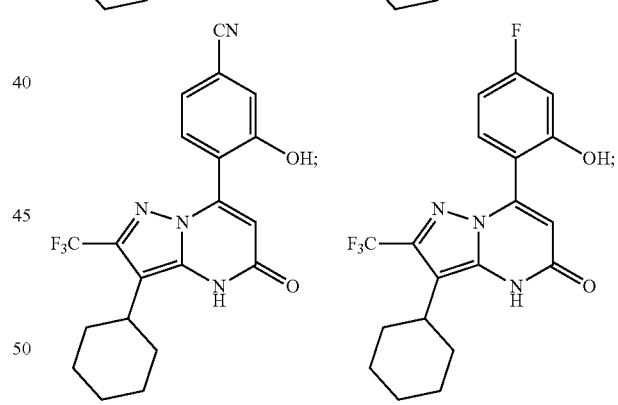
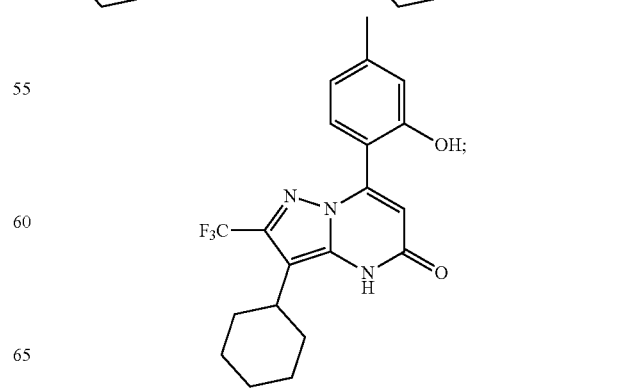

123
-continued
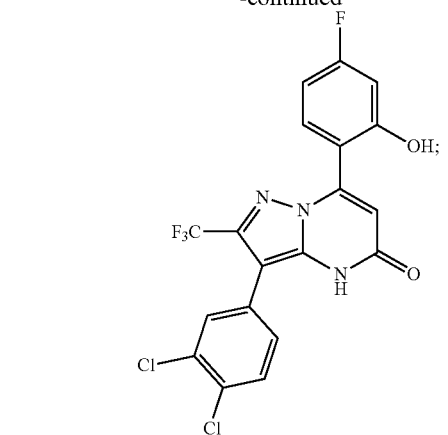
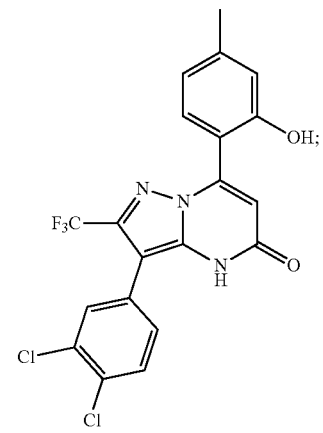
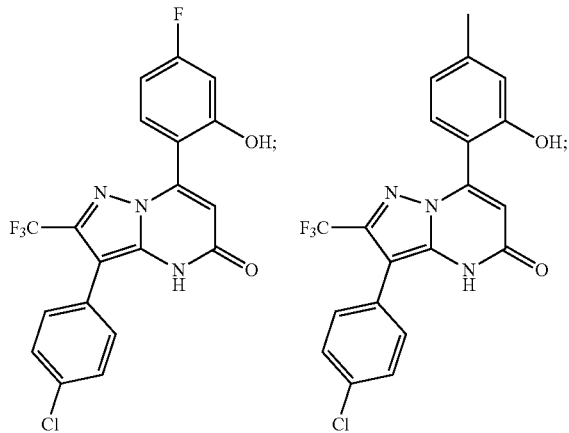
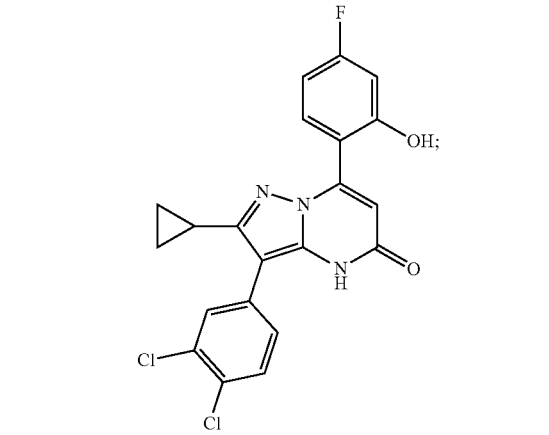
124
-continued
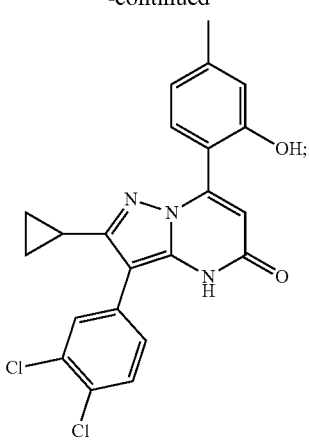
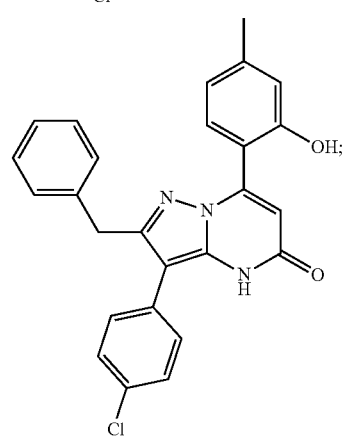
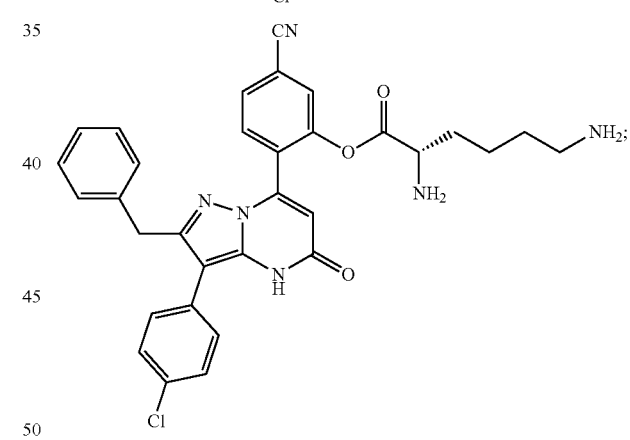
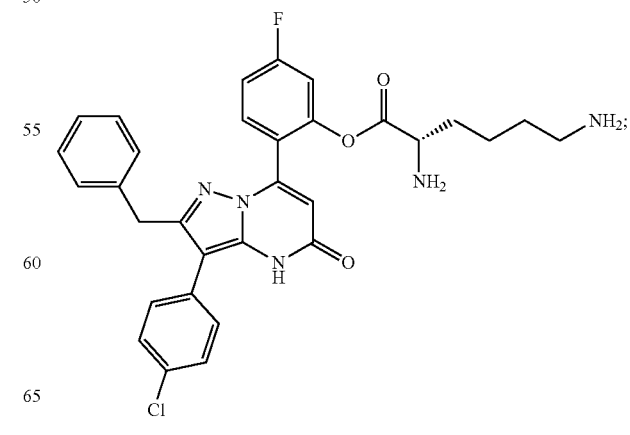

125
-continued
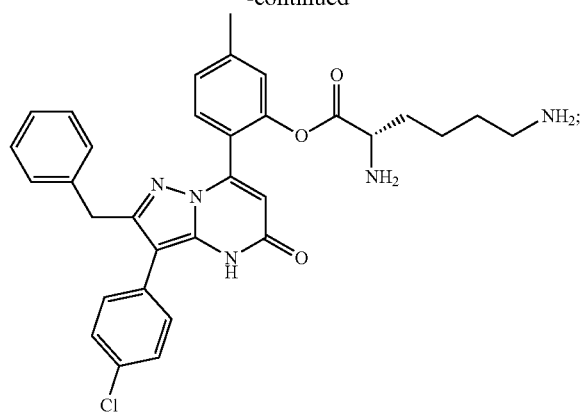
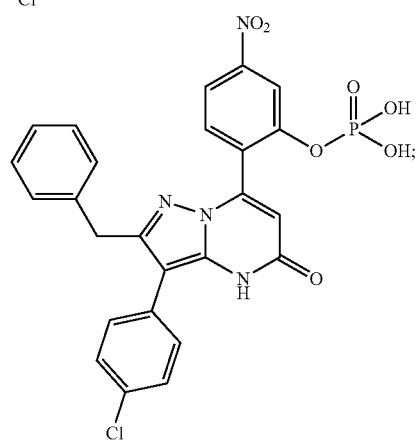
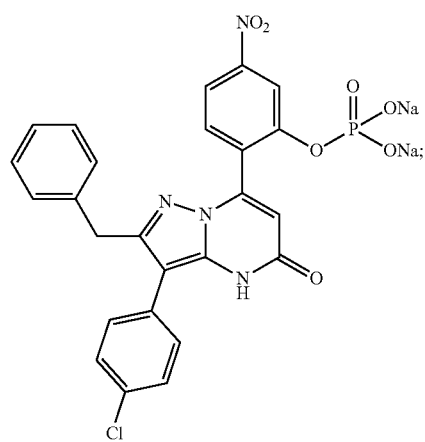
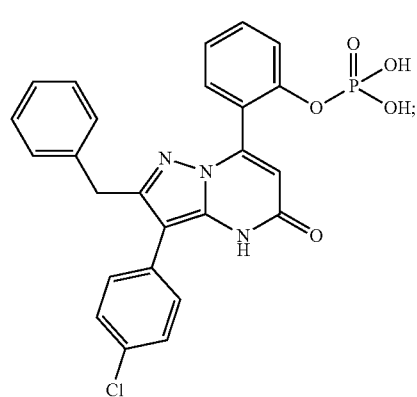
126
-continued
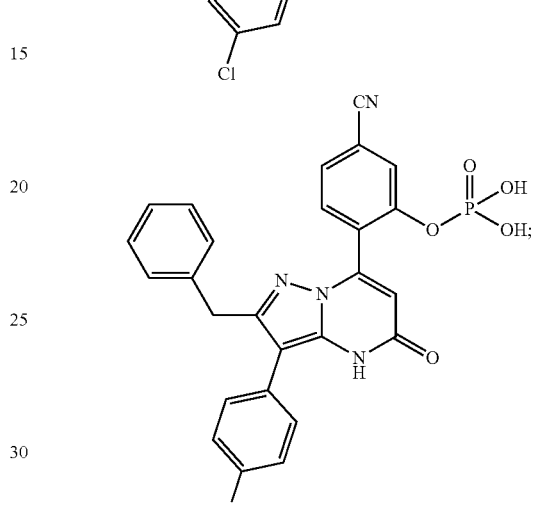
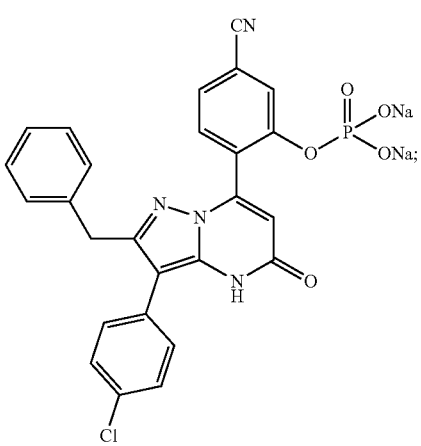
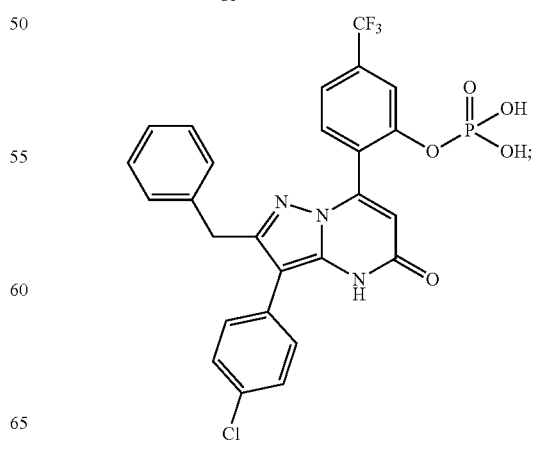

127
-continued
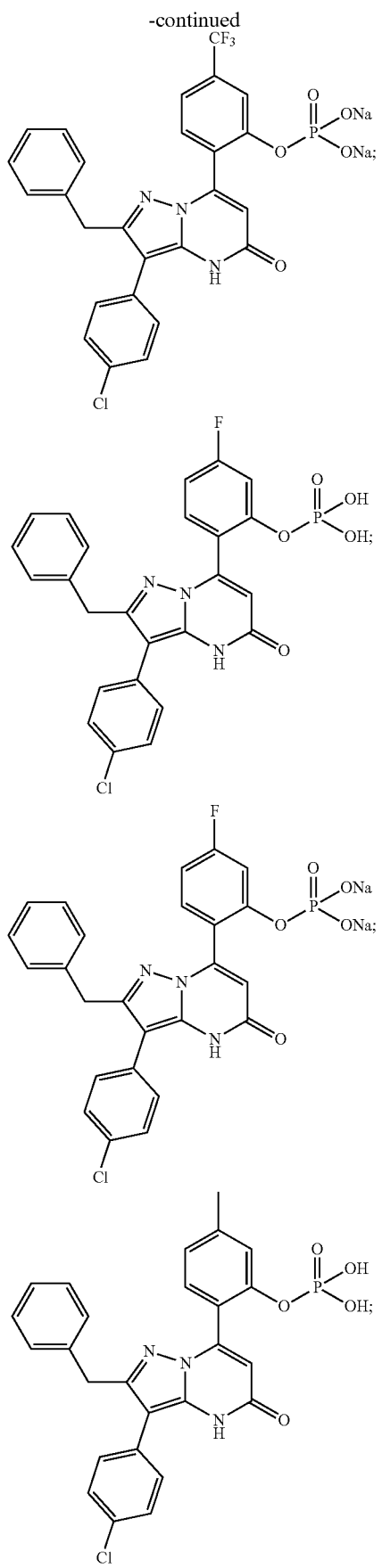
128
-continued
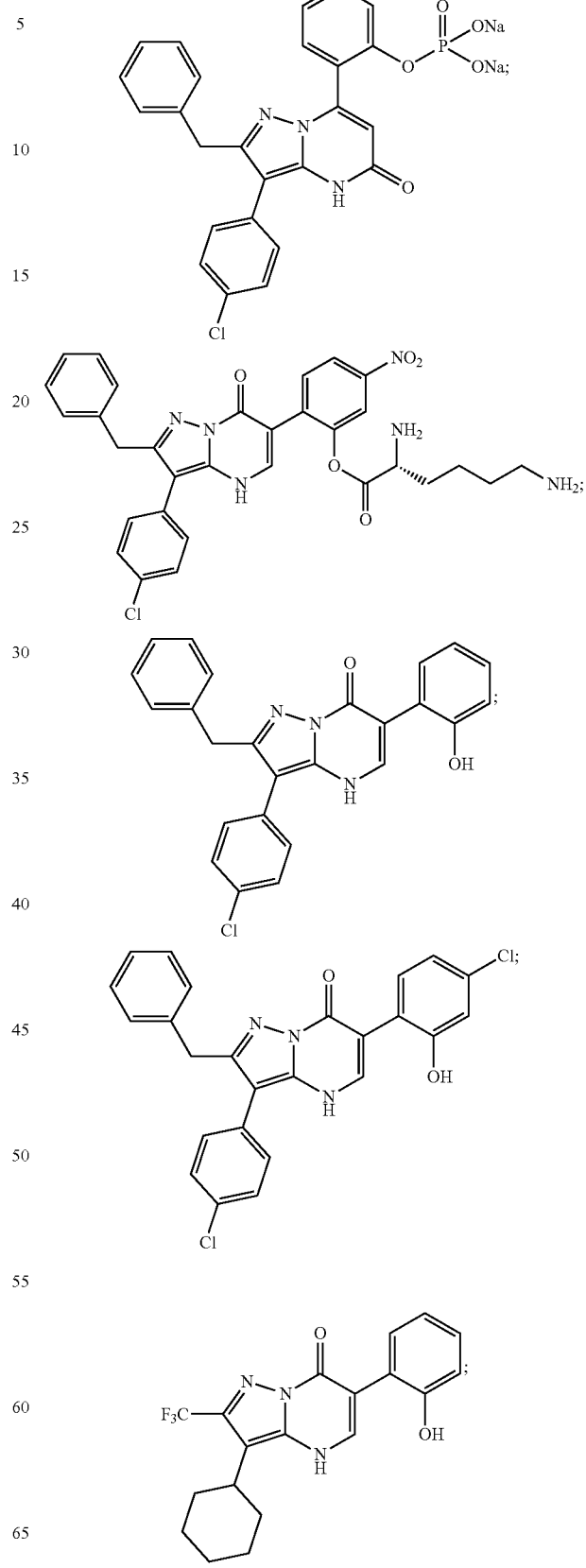

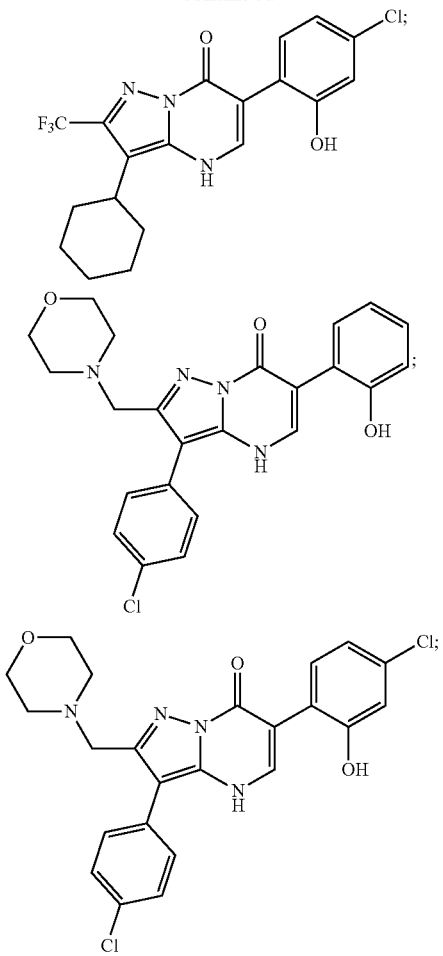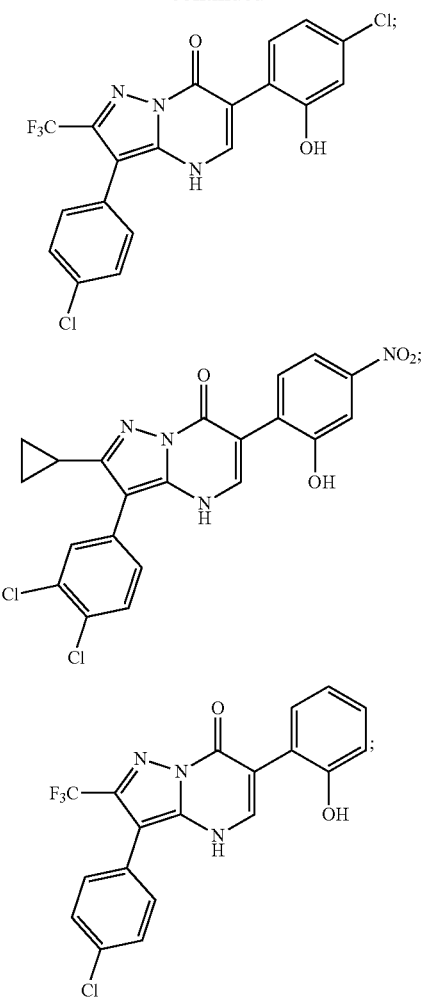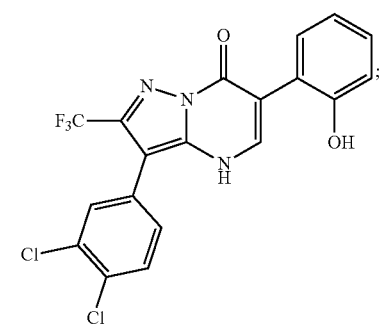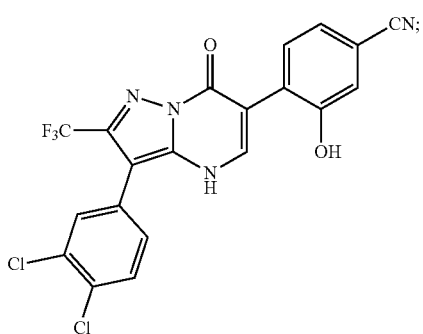

131
-continued
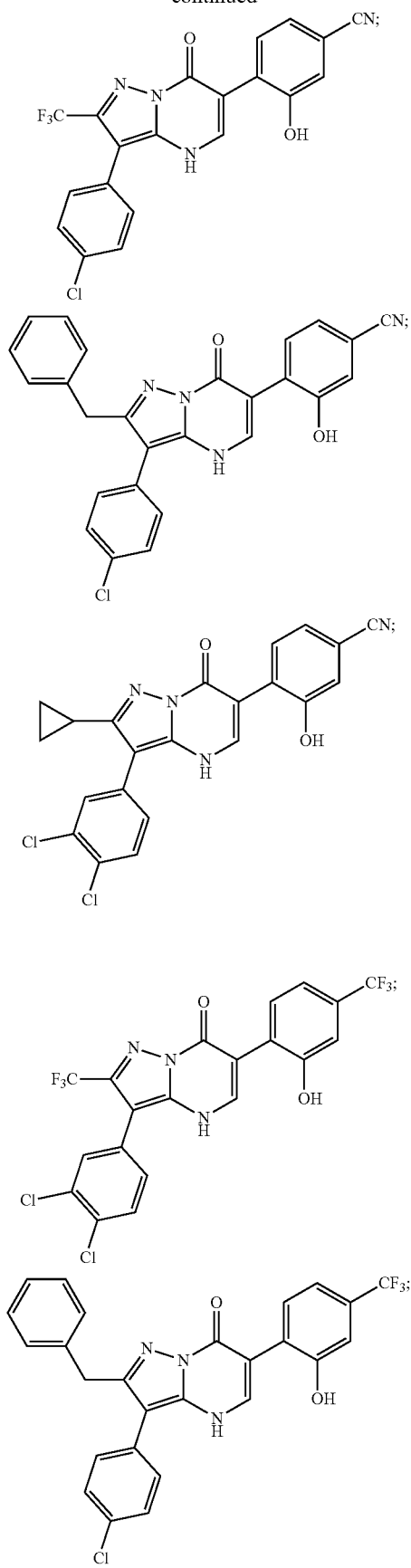
132
-continued
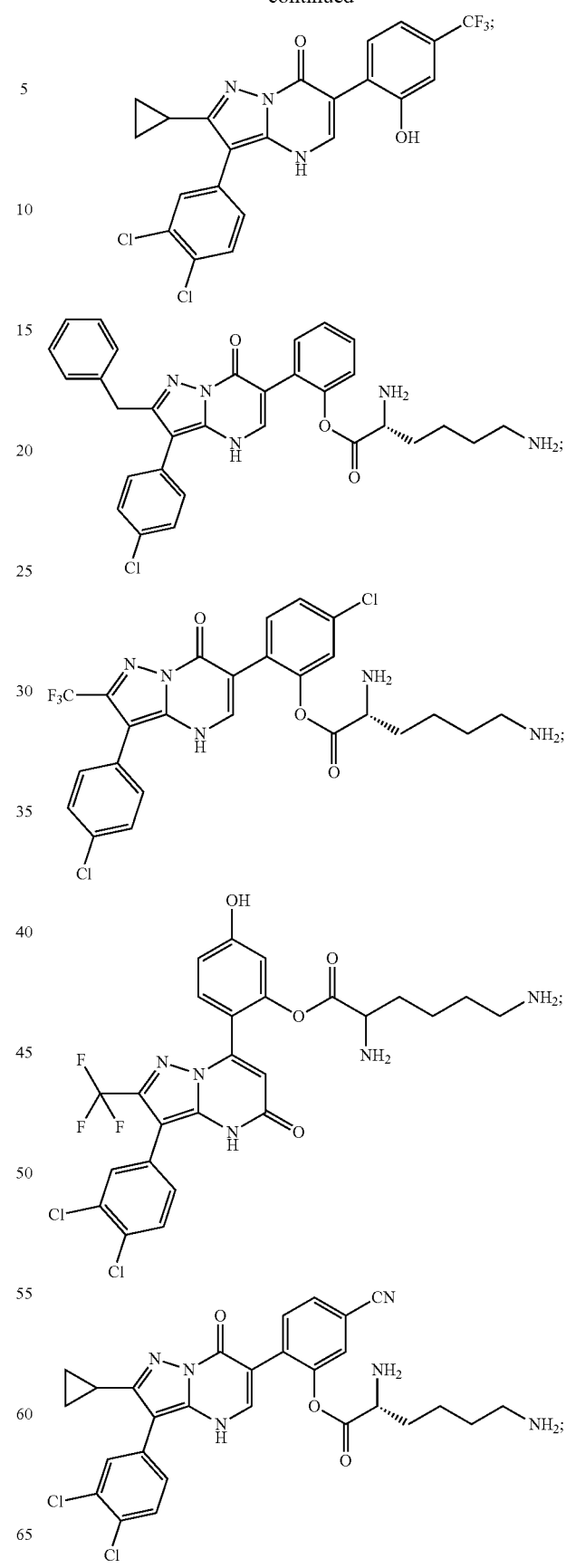

133
-continued
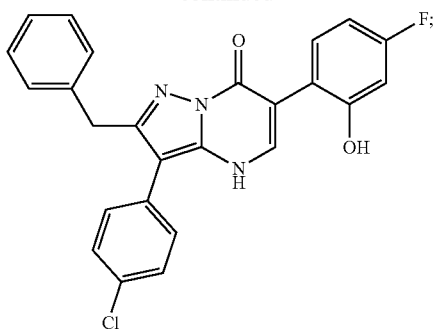
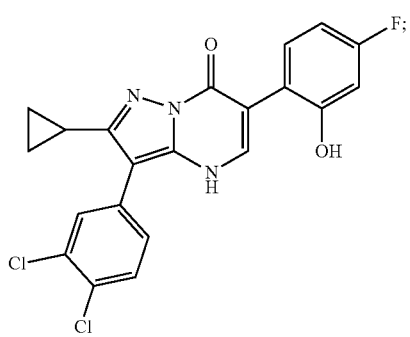
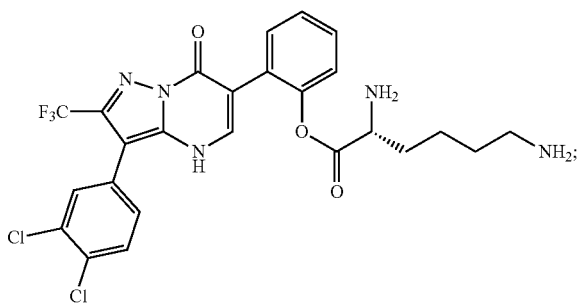
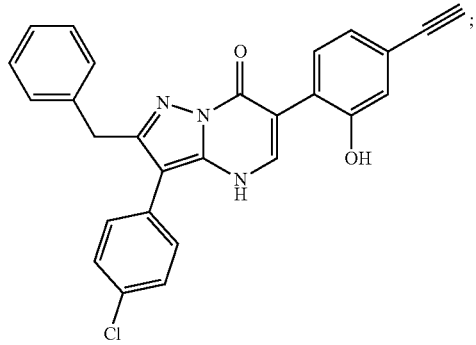
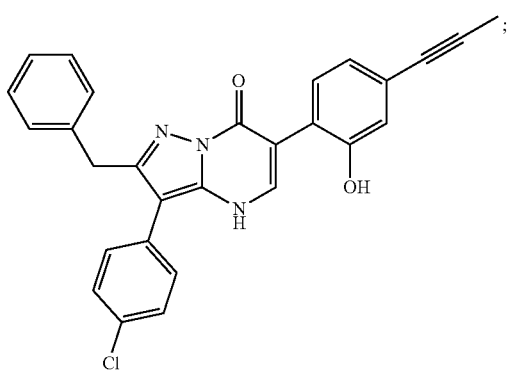
134
-continued
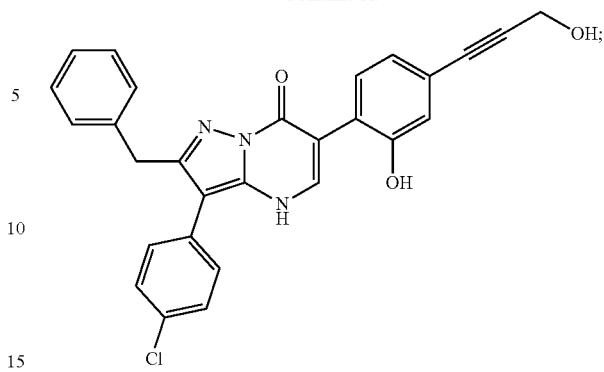
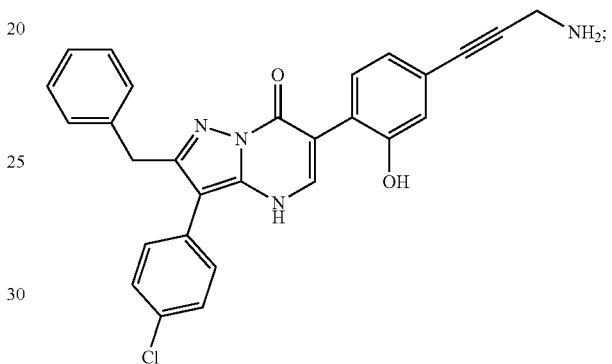
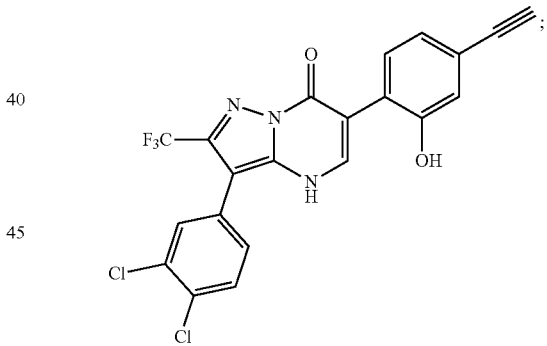
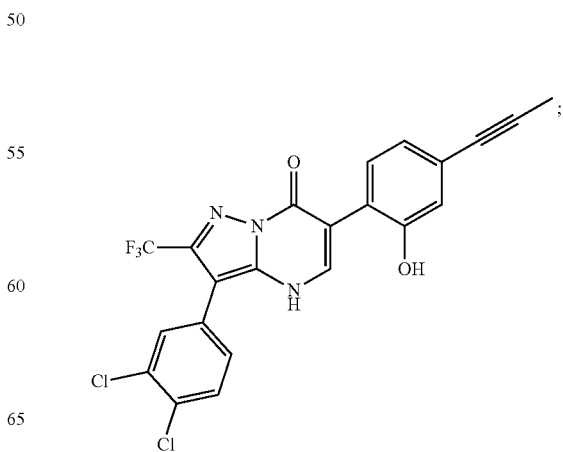

-continued
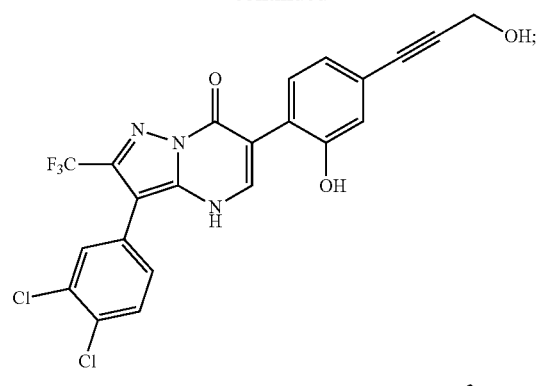
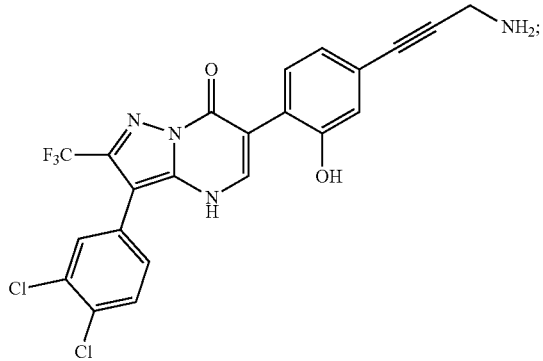
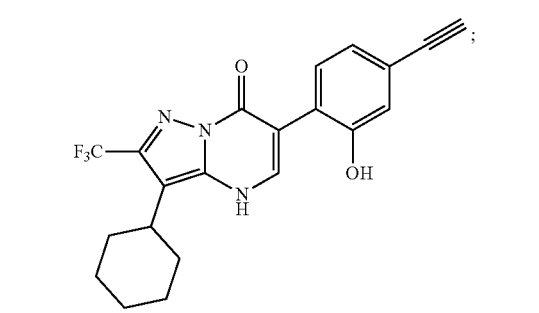
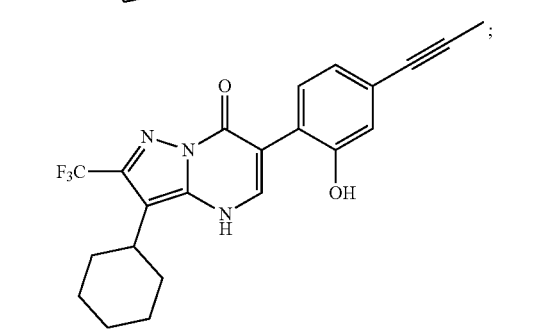
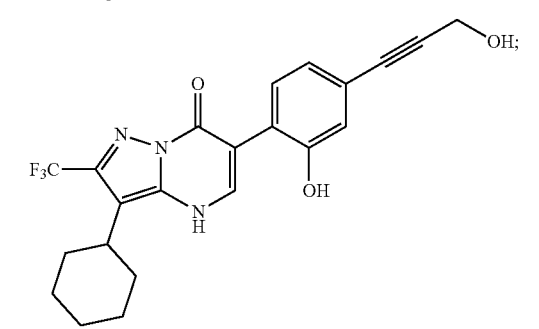
-continued
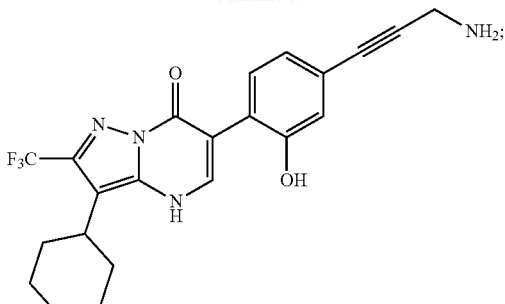
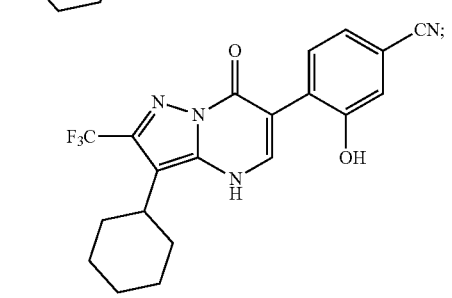
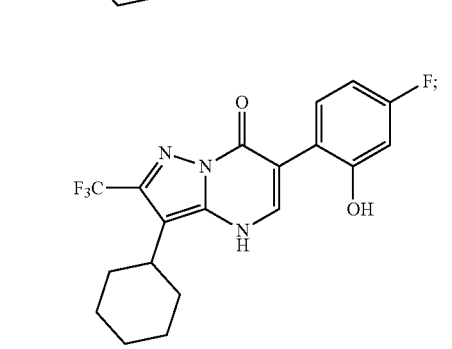
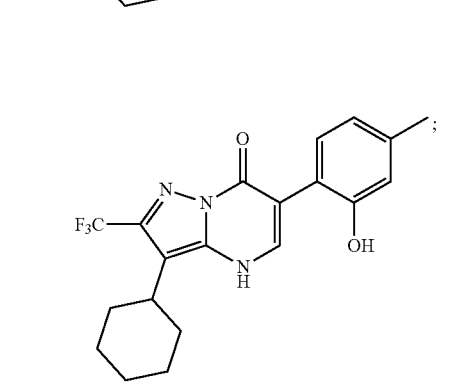
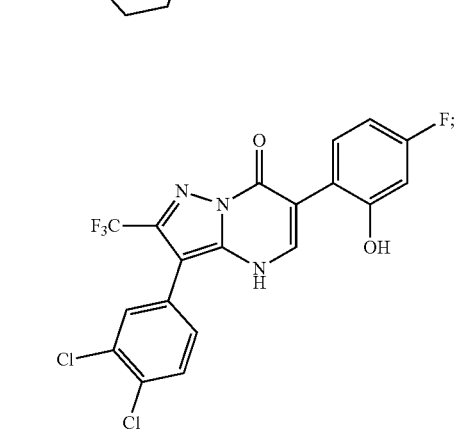

137
-continued
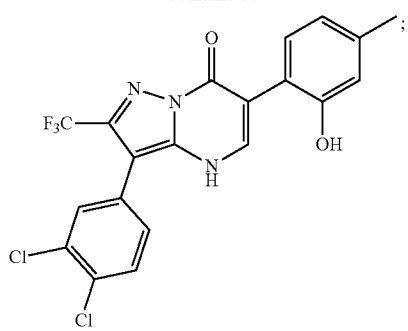
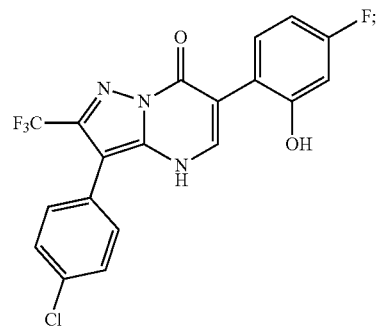
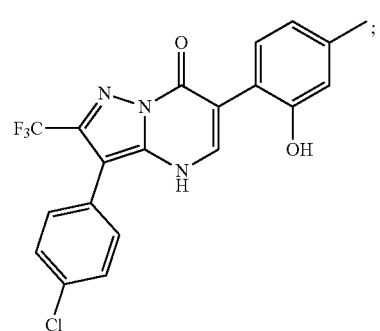
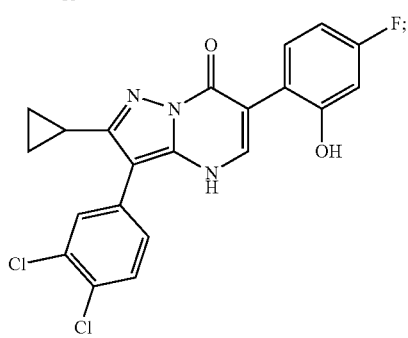
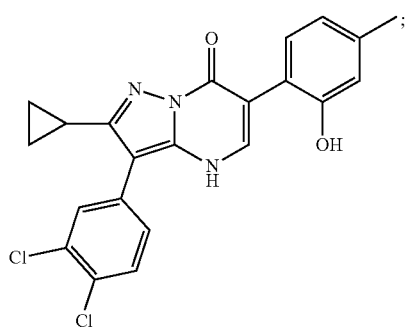
138
-continued
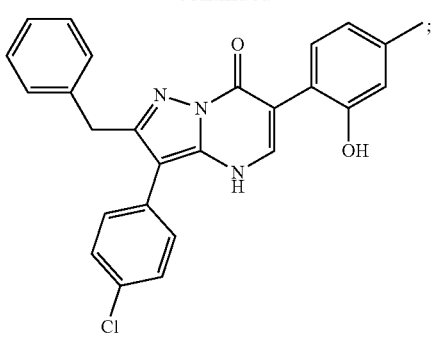
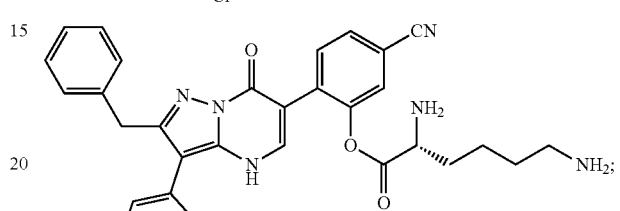
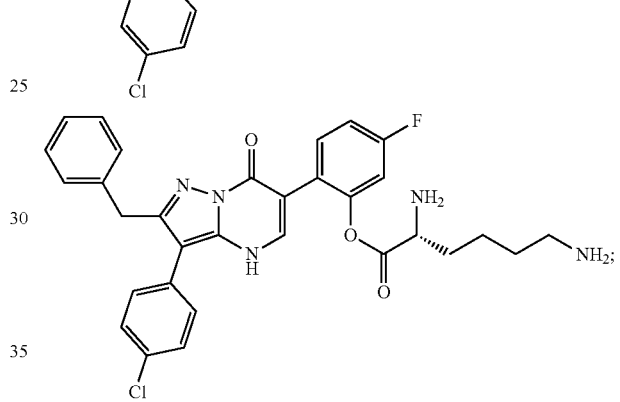
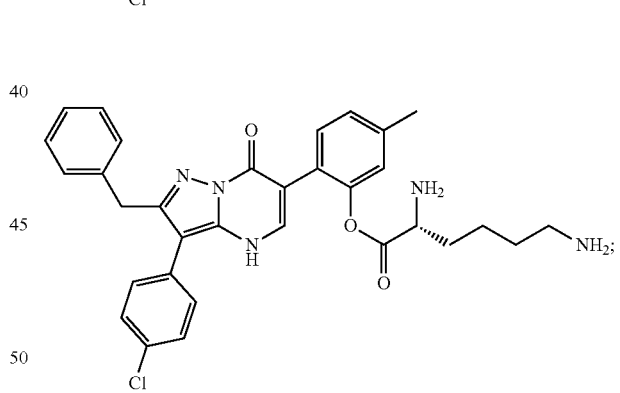
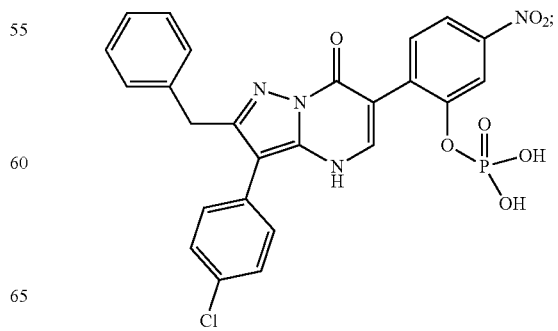

139
-continued
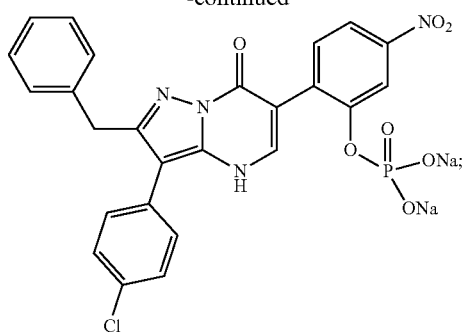
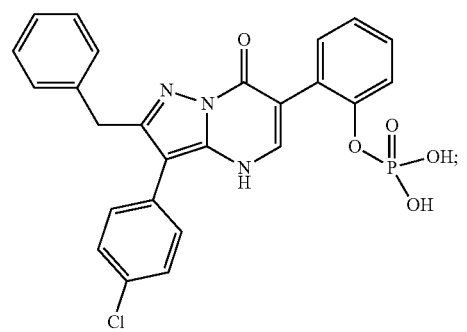
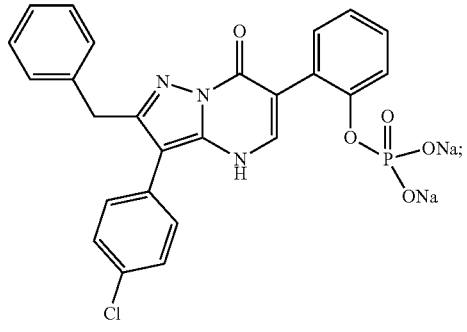
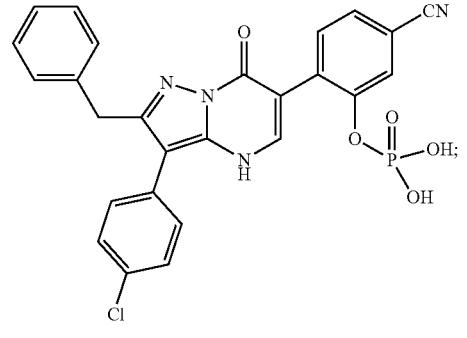
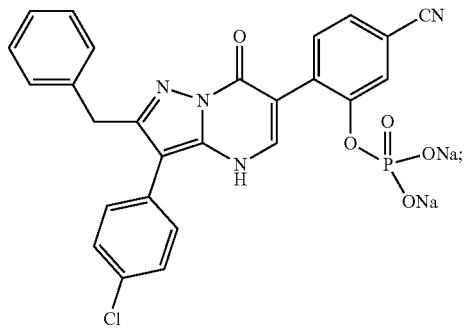
140
-continued
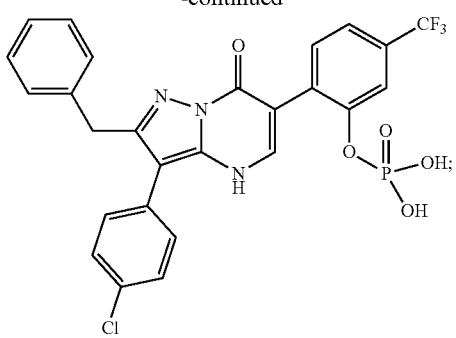
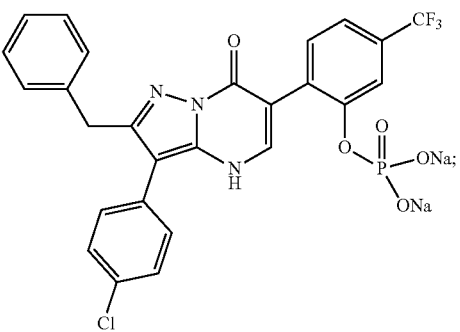
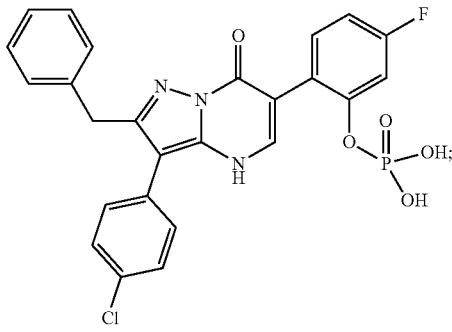
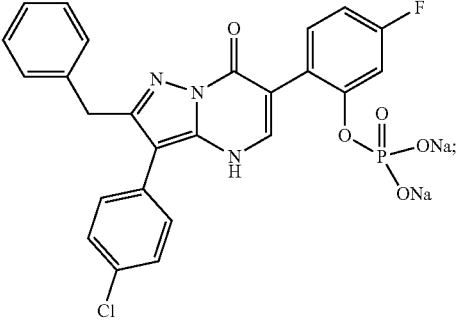
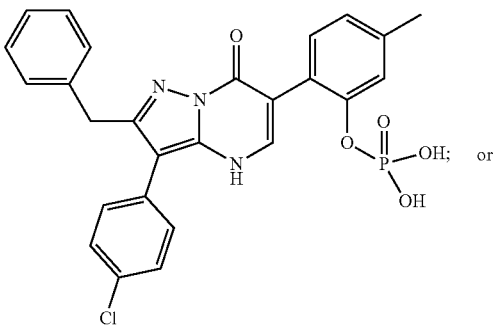

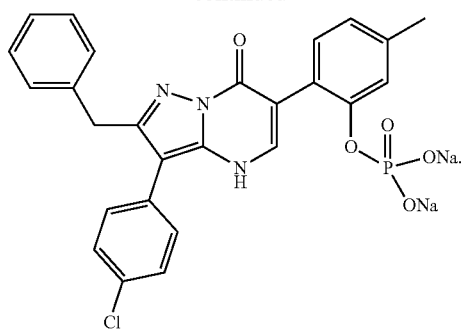

12. A pharmaceutical composition, comprising a compound of claim 1 and
a pharmaceutically acceptable carrier.

13. The pharmaceutical composition of claim 12, wherein the compound is present in an amount effective to treat a patient having, or at risk of developing, a disorder relating to vascular leak, vascular inflammation, angiogenesis, an ocular disorder, or an inflammatory disorder.

14. The composition of claim 1, wherein the compound of Formula I or Formula II is at least one of

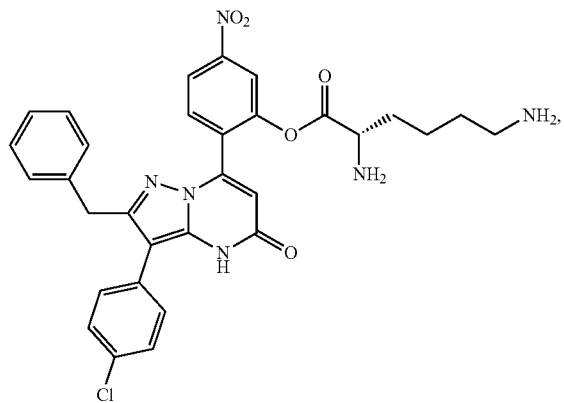

or

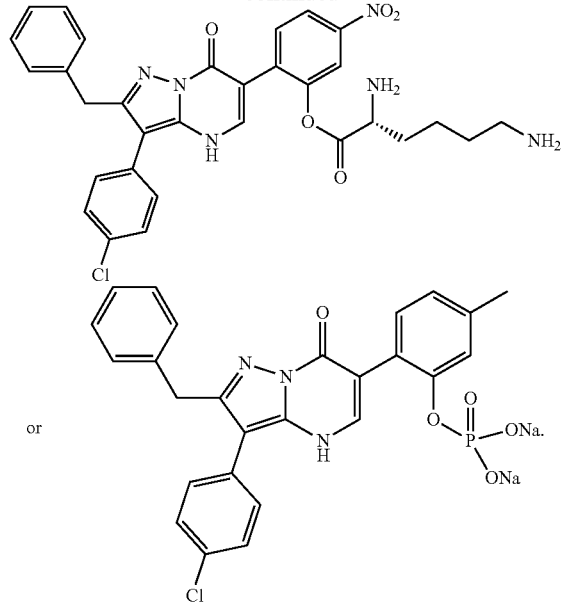

15. The composition of claim 1, wherein the compound of Formula I is

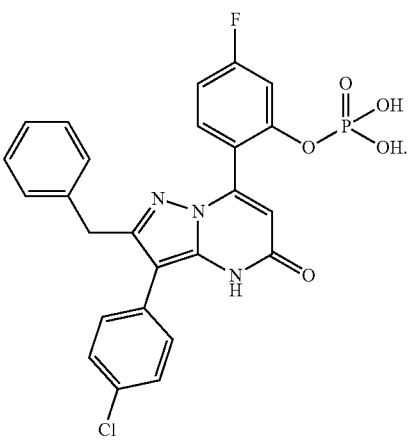 [SMILES: O=c1cc(-c2ccc(F)cc2OP(=O)(O)O)n2nc(Cc3ccccc3)c(-c3ccc(Cl)cc3)c2[nH]1]

16. The composition of claim 1, wherein the compound of Formula II is

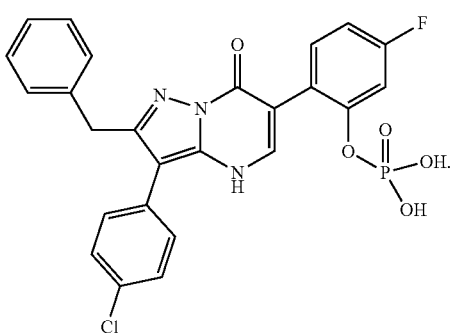 [SMILES: O=c1c(-c2ccc(F)cc2OP(=O)(O)O)c[nH]c2c(-c3ccc(Cl)cc3)c(Cc3ccccc3)nn12]

17. The composition of claim 1, wherein the compound of Formula I is

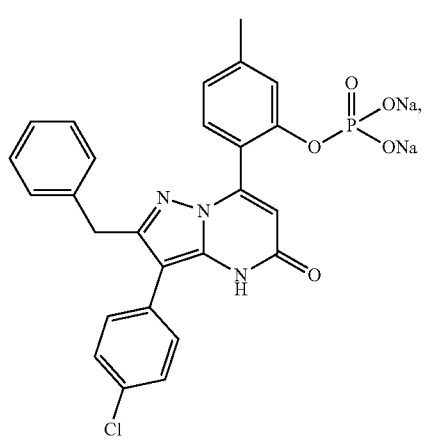

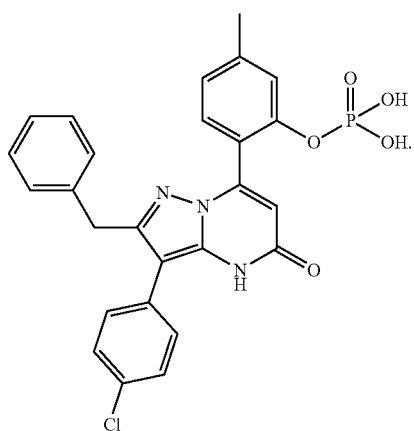 [SMILES: Cc1ccc(-c2cc(=O)[nH]c3c(-c4ccc(Cl)cc4)c(Cc4ccccc4)nn23)c(OP(=O)(O)O)c1]
18. The composition of claim 1, wherein the compound of Formula II is
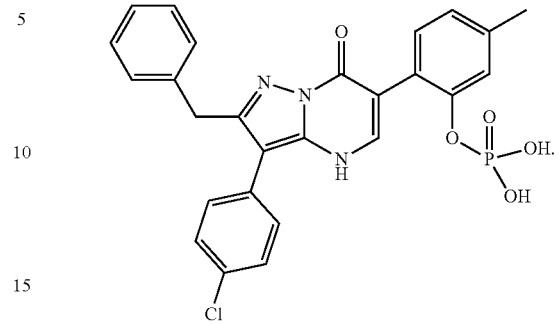
* * * * *